United States Patent
Tessmer et al.

(10) Patent No.: US 8,992,562 B2
(45) Date of Patent: Mar. 31, 2015

(54) FILTER DELIVERY SYSTEM

(75) Inventors: Alexander W. Tessmer, Phoenix, AZ (US); David G. Spilka, Phoenix, AZ (US); David W. Rauch, Sandia Park, NM (US); Andrzej J. Chanduszko, Chandler, AZ (US); Robert M. Carr, Jr., Paradise Valley, AZ (US)

(73) Assignee: C.R. Bard, Inc., Murray Hill, NJ (US)

( * ) Notice: Subject to any disclaimer, the term of this patent is extended or adjusted under 35 U.S.C. 154(b) by 1235 days.

(21) Appl. No.: 12/880,839

(22) Filed: Sep. 13, 2010

(65) Prior Publication Data

US 2011/0034952 A1 Feb. 10, 2011

Related U.S. Application Data

(63) Continuation of application No. 10/986,714, filed on Nov. 12, 2004, now Pat. No. 7,794,473.

(51) Int. Cl.
*A61M 29/00* (2006.01)
*A61F 2/01* (2006.01)

(52) U.S. Cl.
CPC .............. *A61F 2/01* (2013.01); *A61F 2002/011* (2013.01); *A61F 2002/016* (2013.01); *A61F 2230/005* (2013.01); *A61F 2230/0067* (2013.01); *A61F 2230/008* (2013.01)
USPC ........................................................ 606/200

(58) Field of Classification Search
CPC ........ A61F 2/01; A61F 2002/011; A61F 2/95
USPC .................. 606/200, 108, 113, 114, 127, 128; 623/1.11, 1.12
See application file for complete search history.

(56) References Cited

U.S. PATENT DOCUMENTS

| | | | |
|---|---|---|---|
| 3,540,431 A | 11/1970 | Mobin-Uddia | |
| 3,952,747 A | 4/1976 | Kimmell, Jr. | |

(Continued)

FOREIGN PATENT DOCUMENTS

| | | |
|---|---|---|
| EP | 1 042 996 A2 | 10/2000 |
| EP | 1042996 A2 | 10/2000 |

(Continued)

OTHER PUBLICATIONS

European Search Report, Jul. 17, 2013, Munich.

(Continued)

*Primary Examiner* — Darwin Erezo
*Assistant Examiner* — Lindsey Bachman
(74) *Attorney, Agent, or Firm* — Garvey, Smith, Nehrbass & North, L.L.C.; Charles C. Garvey, Jr.; Seth M. Nehrbass

(57) ABSTRACT

A filter delivery device for implanting a vessel filter within a blood vessel of a patient's body. The filter delivery device includes a mechanism for preventing hooks and/or legs on a vessel filter from entangling with each other while the vessel filter is loaded within the delivery device. In one variation, the filter delivery device includes a delivery catheter with grooves at the distal end lumen opening. When a vessel filter with radially expanding legs is compressed and inserted into the distal end of the delivery catheter, the hooks on the distal end of the legs are received and separated by the corresponding grooves on the delivery catheter. In another variation, a pusher rod, with a receptacle for receiving the hooks, is positioned within a delivery catheter to prevent the entanglement of the hooks and/or legs of a filter loaded within the delivery catheter.

20 Claims, 17 Drawing Sheets

(56) References Cited

U.S. PATENT DOCUMENTS

| | | | |
|---|---|---|---|
| 4,000,739 A | 1/1977 | Stevens | |
| 4,282,876 A | 8/1981 | Flynn | |
| 4,283,447 A | 8/1981 | Flynn | |
| 4,411,655 A | 10/1983 | Schreck | |
| 4,419,095 A | 12/1983 | Nebergau et al. | |
| 4,425,908 A | 1/1984 | Simon | |
| 4,494,531 A | 1/1985 | Gianturco | |
| 4,586,501 A | 5/1986 | Claracq | |
| 4,588,399 A | 5/1986 | Nebergall et al. | |
| 4,590,938 A | 5/1986 | Segura et al. | |
| 4,611,594 A | 9/1986 | Grayhack et al. | |
| 4,619,246 A | 10/1986 | Molgaard-Nielsen et al. | |
| 4,643,184 A | 2/1987 | Mobin-Uddin | |
| 4,657,024 A | 4/1987 | Coneys | |
| 4,665,918 A * | 5/1987 | Garza et al. | 606/108 |
| 4,688,553 A | 8/1987 | Metals | |
| 4,710,192 A | 12/1987 | Liotta et al. | |
| 4,722,344 A | 2/1988 | Cambron et al. | |
| 4,727,873 A | 3/1988 | Mobin-Uddin | |
| 4,781,177 A | 11/1988 | Lebigot | |
| 4,793,348 A | 12/1988 | Palmaz | |
| 4,798,591 A | 1/1989 | Okada | |
| 4,817,600 A | 4/1989 | Herms et al. | |
| 4,832,055 A | 5/1989 | Palestrant | |
| 4,838,879 A | 6/1989 | Tanabe et al. | |
| 4,857,062 A | 8/1989 | Russell | |
| 4,863,442 A | 9/1989 | DeMello et al. | |
| 4,873,978 A | 10/1989 | Ginsburg | |
| 4,886,506 A | 12/1989 | Lovgren et al. | |
| 4,898,591 A | 2/1990 | Jang et al. | |
| 4,922,905 A | 5/1990 | Strecker | |
| 4,936,823 A * | 6/1990 | Colvin et al. | 600/7 |
| 4,950,227 A | 8/1990 | Savin et al. | |
| 4,957,501 A | 9/1990 | Lahille et al. | |
| 4,969,891 A | 11/1990 | Gewertz | |
| 4,990,156 A | 2/1991 | Lefebvre | |
| 5,045,072 A | 9/1991 | Castillo et al. | |
| 5,059,205 A | 10/1991 | El-Noumou et al. | |
| 5,108,418 A | 4/1992 | Lefebvre | |
| 5,114,408 A | 5/1992 | Fleischhaker et al. | |
| 5,133,733 A | 7/1992 | Rasmussen et al. | |
| 5,147,379 A | 9/1992 | Sabbaghian et al. | |
| 5,152,777 A | 10/1992 | Goldberg et al. | |
| 5,171,232 A | 12/1992 | Castillo et al. | |
| 5,188,616 A | 2/1993 | Nadal | |
| 5,203,776 A | 4/1993 | Durfee | |
| 5,234,416 A | 8/1993 | Macaulay et al. | |
| 5,234,458 A | 8/1993 | Metais | |
| 5,242,462 A | 9/1993 | El-Nounou et al. | |
| 5,300,086 A | 4/1994 | Gory et al. | |
| 5,304,156 A | 4/1994 | Sylvanowicz et al. | |
| 5,324,304 A | 6/1994 | Rasmussen | |
| 5,329,942 A | 7/1994 | Gunther et al. | |
| 5,350,398 A | 9/1994 | Pavenik et al. | |
| 5,358,493 A | 10/1994 | Schweich, Jr. | |
| 5,370,657 A | 12/1994 | Irie | |
| 5,375,612 A | 12/1994 | Cottenceau et al. | |
| 5,383,887 A | 1/1995 | Nadal | |
| 5,413,586 A | 5/1995 | Dibie et al. | |
| 5,421,832 A | 6/1995 | Lefebvre | |
| 5,423,851 A | 6/1995 | Samuels | |
| 5,443,497 A | 8/1995 | Venbrux | |
| 5,485,667 A | 1/1996 | Kleshinski | |
| 5,520,657 A | 5/1996 | Sellers et al. | |
| 5,531,788 A | 7/1996 | Dibie et al. | |
| 5,545,151 A | 8/1996 | O'Connor | |
| 5,549,576 A | 8/1996 | Patterson et al. | |
| 5,558,652 A | 9/1996 | Henke | |
| 5,601,568 A | 2/1997 | Chevillon et al. | |
| 5,601,595 A | 2/1997 | Smith | |
| 5,624,508 A | 4/1997 | Flomenblit et al. | |
| 5,626,605 A | 5/1997 | Irie | |
| 5,634,942 A | 6/1997 | Chevillon et al. | |
| 5,641,364 A | 6/1997 | Golberg et al. | |
| 5,649,906 A | 7/1997 | Gory et al. | |
| 5,669,879 A | 9/1997 | Duer | |
| 5,669,933 A | 9/1997 | Simon et al. | |
| 5,672,153 A | 9/1997 | Lax | |
| 5,672,158 A | 9/1997 | Okada et al. | |
| 5,681,347 A | 10/1997 | Cathcart et al. | |
| 5,683,411 A | 11/1997 | Kavteladze et al. | |
| 5,695,518 A | 12/1997 | Laerum | |
| 5,695,519 A | 12/1997 | Summers et al. | |
| 5,702,370 A | 12/1997 | Sylvanowicz et al. | |
| 5,704,910 A | 1/1998 | Humes | |
| 5,704,926 A | 1/1998 | Sutton | |
| 5,709,704 A | 1/1998 | Nott et al. | |
| 5,720,764 A | 2/1998 | Naderlinger | |
| 5,725,550 A | 3/1998 | Nadal | |
| 5,746,767 A | 5/1998 | Smith | |
| 5,755,790 A | 5/1998 | Chevillon et al. | |
| 5,759,192 A | 6/1998 | Saunders | |
| 5,769,816 A | 6/1998 | Barbut | |
| 5,776,162 A | 7/1998 | Kleshinski | |
| 5,780,807 A | 7/1998 | Saunders | |
| 5,800,457 A | 9/1998 | Gelbfish | |
| 5,800,515 A | 9/1998 | Nadal et al. | |
| 5,830,222 A | 11/1998 | Makower | |
| 5,836,968 A | 11/1998 | Simon et al. | |
| 5,836,969 A | 11/1998 | Kim et al. | |
| 5,853,420 A * | 12/1998 | Chevillon et al. | 606/200 |
| 5,893,869 A | 4/1999 | Barnhart et al. | |
| 5,897,497 A | 4/1999 | Fernandez | |
| 5,911,704 A | 6/1999 | Humes | |
| 5,919,224 A | 7/1999 | Thompson et al. | |
| 5,928,261 A | 7/1999 | Ruiz | |
| 5,951,585 A | 9/1999 | Cathcart | |
| 5,954,741 A | 9/1999 | Fox | |
| 5,968,071 A | 10/1999 | Chevillon et al. | |
| 5,972,019 A | 10/1999 | Engelson et al. | |
| 5,976,172 A | 11/1999 | Homsma et al. | |
| 5,980,503 A | 11/1999 | Chin | |
| 5,984,947 A | 11/1999 | Smith | |
| 6,001,118 A | 12/1999 | Daniel et al. | |
| 6,007,558 A | 12/1999 | Ravenscroft et al. | |
| 6,013,093 A | 1/2000 | Nott et al. | |
| 6,027,518 A | 2/2000 | Gaber | |
| 6,036,723 A | 3/2000 | Anidjar et al. | |
| 6,051,015 A | 4/2000 | Maahs | |
| 6,059,814 A | 5/2000 | Ladd | |
| 6,059,825 A | 5/2000 | Hobbs et al. | |
| 6,066,158 A | 5/2000 | Engelson et al. | |
| 6,068,638 A | 5/2000 | Makower | |
| 6,071,263 A | 6/2000 | Kirkman | |
| 6,071,292 A | 6/2000 | Makower et al. | |
| 6,077,880 A | 6/2000 | Castillo et al. | |
| 6,080,178 A | 6/2000 | Meglin | |
| 6,099,549 A | 8/2000 | Bosma et al. | |
| 6,126,645 A | 10/2000 | Thompson | |
| 6,126,673 A | 10/2000 | Kim et al. | |
| 6,131,266 A | 10/2000 | Saunders | |
| 6,132,388 A | 10/2000 | Fleming | |
| 6,146,404 A | 11/2000 | Kim et al. | |
| 6,156,055 A | 12/2000 | Ravenscroft | |
| 6,159,225 A | 12/2000 | Makower | |
| 6,162,357 A | 12/2000 | Pakki et al. | |
| 6,165,179 A | 12/2000 | Cathcart | |
| 6,165,200 A | 12/2000 | Tsugita et al. | |
| 6,171,297 B1 | 1/2001 | Pedersen | |
| 6,190,353 B1 | 2/2001 | Makower et al. | |
| 6,193,739 B1 * | 2/2001 | Chevillon et al. | 606/200 |
| 6,193,748 B1 | 2/2001 | Thompson et al. | |
| 6,214,025 B1 | 4/2001 | Thistle et al. | |
| 6,217,600 B1 | 4/2001 | DiMatteo | |
| 6,228,052 B1 | 5/2001 | Pohndorf | |
| 6,231,581 B1 | 5/2001 | Shank et al. | |
| 6,231,587 B1 | 5/2001 | Makower | |
| 6,231,588 B1 | 5/2001 | Zadno-Azizi | |
| 6,231,589 B1 | 5/2001 | Wessmann et al. | |
| 6,235,045 B1 | 5/2001 | Barbut | |
| 6,241,746 B1 | 6/2001 | Bosma et al. | |
| 6,245,012 B1 | 6/2001 | Kleshinski | |
| 6,251,122 B1 | 6/2001 | Tsukernik | |
| 6,254,633 B1 | 7/2001 | Pinchuk et al. | |

(56) References Cited

U.S. PATENT DOCUMENTS

| | | |
|---|---|---|
| 6,258,026 B1 | 7/2001 | Ravenscroft et al. |
| 6,258,101 B1 | 7/2001 | Blake |
| 6,264,671 B1 | 7/2001 | Stack et al. |
| 6,267,776 B1 | 7/2001 | O'Connell |
| 6,267,777 B1 | 7/2001 | Bosma et al. |
| 6,273,900 B1 | 8/2001 | Nott et al. |
| 6,273,901 B1 | 8/2001 | Whitcher et al. |
| 6,283,983 B1 | 9/2001 | Makower et al. |
| 6,287,317 B1 | 9/2001 | Makower et al. |
| 6,290,710 B1 | 9/2001 | Cryer et al. |
| 6,302,875 B1 | 10/2001 | Makower et al. |
| 6,302,891 B1 | 10/2001 | Nadal |
| 6,322,541 B2 | 11/2001 | West et al. |
| 6,325,790 B1 | 12/2001 | Trotta |
| 6,328,755 B1 | 12/2001 | Marshall |
| 6,331,183 B1 | 12/2001 | Suon |
| 6,336,934 B1 | 1/2002 | Gilson et al. |
| 6,342,062 B1 | 1/2002 | Suon et al. |
| 6,342,063 B1 | 1/2002 | DeVries et al. |
| 6,383,193 B1 | 5/2002 | Cathcart et al. |
| 6,383,206 B1 | 5/2002 | Gillick et al. |
| 6,391,045 B1 | 5/2002 | Kim et al. |
| 6,402,771 B1 | 6/2002 | Palmer et al. |
| 6,416,530 B2 | 7/2002 | DeVries et al. |
| 6,428,559 B1 | 8/2002 | Johnson |
| 6,432,127 B1 | 8/2002 | Kim et al. |
| 6,436,121 B1 | 8/2002 | Blom |
| 6,440,077 B1 | 8/2002 | Jung et al. |
| 6,440,163 B1 | 8/2002 | Swanson et al. |
| 6,442,413 B1 | 8/2002 | Silver |
| 6,443,971 B1 | 9/2002 | Boylan et al. |
| 6,443,972 B1 | 9/2002 | Bosma et al. |
| 6,447,530 B1 | 9/2002 | Ostrovsky et al. |
| 6,458,145 B1 | 10/2002 | Ravenscroft et al. |
| 6,468,290 B1 | 10/2002 | Weldon et al. |
| 6,482,222 B1 | 11/2002 | Bruckheimer et al. |
| 6,485,500 B1 | 11/2002 | Kokish et al. |
| 6,485,502 B2 | 11/2002 | Don Michael et al. |
| 6,485,662 B1 | 11/2002 | Neubauer et al. |
| 6,488,662 B2 | 12/2002 | Sirimanne |
| 6,497,709 B1 | 12/2002 | Heath |
| 6,506,205 B2 | 1/2003 | Goldberg et al. |
| 6,511,492 B1 | 1/2003 | Rosenbluth et al. |
| 6,511,496 B1 | 1/2003 | Huter et al. |
| 6,511,503 B1 | 1/2003 | Burkart et al. |
| 6,517,559 B1 | 2/2003 | O'Connell |
| 6,517,573 B1 | 2/2003 | Pollock et al. |
| 6,537,294 B1 | 3/2003 | Boyle et al. |
| 6,537,295 B2 | 3/2003 | Petersen |
| 6,540,722 B1 | 4/2003 | Boyle et al. |
| 6,540,767 B1 | 4/2003 | Walak et al. |
| 6,540,768 B1 | 4/2003 | Diaz et al. |
| 6,544,280 B1 | 4/2003 | Daniel et al. |
| 6,551,303 B1 | 4/2003 | Van Tassel et al. |
| 6,551,340 B1 | 4/2003 | Konya et al. |
| 6,551,342 B1 | 4/2003 | Shen et al. |
| 6,558,404 B2 | 5/2003 | Tsukernik |
| 6,558,405 B1 | 5/2003 | McInnes |
| 6,558,406 B2 | 5/2003 | Okada |
| 6,563,080 B2 | 5/2003 | Shapovalov et al. |
| 6,569,183 B1 | 5/2003 | Kim et al. |
| 6,569,184 B2 | 5/2003 | Huter |
| 6,572,605 B1 | 6/2003 | Humes |
| 6,575,997 B1 | 6/2003 | Palmer et al. |
| 6,582,447 B1 | 6/2003 | Patel et al. |
| 6,585,715 B1 | 7/2003 | Teirstein |
| 6,589,266 B2 | 7/2003 | Whitcher et al. |
| 6,592,607 B1 | 7/2003 | Palmer et al. |
| 6,592,616 B1 | 7/2003 | Stack et al. |
| 6,596,011 B2 | 7/2003 | Johnson et al. |
| 6,602,273 B2 | 8/2003 | Marhall |
| 6,607,553 B1 | 8/2003 | Healy et al. |
| 6,610,077 B1 | 8/2003 | Hancock et al. |
| 6,616,680 B1 | 9/2003 | Thielen |
| 6,616,681 B2 | 9/2003 | Hanson et al. |
| 6,620,183 B2 | 9/2003 | DiMatteo |
| 6,623,450 B1 | 9/2003 | Dutta |
| 6,623,506 B2 | 9/2003 | McGuckin, Jr. et al. |
| 6,629,993 B2 | 10/2003 | Voinov |
| 6,640,077 B2 | 10/2003 | Suzuki |
| 6,641,590 B1 | 11/2003 | Palmer et al. |
| 6,645,152 B1 | 11/2003 | Jung et al. |
| 6,645,224 B2 | 11/2003 | Gilson et al. |
| 6,652,555 B1 | 11/2003 | Van Tassel et al. |
| 6,652,556 B1 | 11/2003 | Van Tassel et al. |
| 6,652,558 B2 | 11/2003 | Patel et al. |
| 6,652,692 B2 | 11/2003 | Pedersen |
| 6,656,203 B2 | 12/2003 | Roth et al. |
| 6,660,021 B1 | 12/2003 | Palmer et al. |
| 6,663,650 B2 | 12/2003 | Sepetka et al. |
| 6,669,716 B1 | 12/2003 | Gilson et al. |
| 6,679,902 B1 | 1/2004 | Boyle et al. |
| 6,679,903 B2 | 1/2004 | Kurz |
| 6,685,722 B1 | 2/2004 | Rosenbluth et al. |
| 6,685,738 B2 | 2/2004 | Chouinard et al. |
| 6,689,150 B1 | 2/2004 | Van Tassel et al. |
| 6,695,813 B1 | 2/2004 | Boyle et al. |
| 6,696,667 B1 | 2/2004 | Flanagan |
| 6,702,834 B1 | 3/2004 | Boylan et al. |
| 6,706,054 B2 | 3/2004 | Wessman et al. |
| 6,716,208 B2 | 4/2004 | Humes |
| 6,719,717 B1 | 4/2004 | Johnson et al. |
| 6,719,772 B2 | 4/2004 | Trask et al. |
| 6,726,621 B2 | 4/2004 | Suon |
| 6,730,108 B2 | 5/2004 | Van Tassel et al. |
| 6,736,842 B2 | 5/2004 | Healy et al. |
| 6,755,846 B1 | 6/2004 | Yadav |
| 6,761,732 B2 | 7/2004 | Burkett et al. |
| 6,773,448 B2 | 8/2004 | Kusleika et al. |
| 6,776,770 B1 | 8/2004 | Trerotola |
| 6,776,774 B2 | 8/2004 | Tansey, Jr. et al. |
| 6,783,538 B2 | 8/2004 | McGuckin, Jr. et al. |
| 6,792,979 B2 | 9/2004 | Konya et al. |
| 6,793,665 B2 | 9/2004 | McGuckin, Jr. et al. |
| 6,793,666 B2 | 9/2004 | Hansen et al. |
| 6,818,006 B2 | 11/2004 | Douk et al. |
| 6,840,950 B2 | 1/2005 | Stanford et al. |
| 6,843,798 B2 | 1/2005 | Kusleika et al. |
| 6,849,061 B2 | 2/2005 | Wagner |
| 6,872,217 B2 | 3/2005 | Walak et al. |
| 6,881,218 B2 | 4/2005 | Beyer et al. |
| 7,001,424 B2 | 2/2006 | Patel et al. |
| 7,033,376 B2 | 4/2006 | Tsukernik |
| 7,041,117 B2 | 5/2006 | Suon et al. |
| 7,147,649 B2 | 12/2006 | Thomas |
| 7,794,473 B2 | 9/2010 | Tessmer et al. |
| 2001/0000799 A1 | 5/2001 | Wessman et al. |
| 2001/0020175 A1 | 9/2001 | Yassour et al. |
| 2001/0023358 A1 | 9/2001 | Tsukernik |
| 2001/0039431 A1 | 11/2001 | DeVries et al. |
| 2002/0032461 A1* | 3/2002 | Marshall ............... 606/200 |
| 2002/0042626 A1 | 4/2002 | Hanson et al. |
| 2002/0045918 A1 | 4/2002 | Suon et al. |
| 2002/0055767 A1 | 5/2002 | Forde et al. |
| 2002/0116024 A1 | 8/2002 | Goldberg et al. |
| 2002/0138097 A1 | 9/2002 | Ostrovsky et al. |
| 2002/0193825 A1 | 12/2002 | McGuckin, Jr. et al. |
| 2002/0193826 A1 | 12/2002 | McGuckin, Jr. et al. |
| 2002/0193827 A1 | 12/2002 | McGuckin, Jr. et al. |
| 2002/0193828 A1 | 12/2002 | Griffin et al. |
| 2003/0004540 A1 | 1/2003 | Linder et al. |
| 2003/0004541 A1 | 1/2003 | Linder et al. |
| 2003/0028241 A1 | 2/2003 | Stinson |
| 2003/0071285 A1 | 4/2003 | Tsukernik |
| 2003/0093110 A1 | 5/2003 | Vale |
| 2003/0097145 A1 | 5/2003 | Goldberg et al. |
| 2003/0109824 A1 | 6/2003 | Anderson et al. |
| 2003/0109897 A1 | 6/2003 | Walak et al. |
| 2003/0114735 A1 | 6/2003 | Silver et al. |
| 2003/0114880 A1 | 6/2003 | Hansen et al. |
| 2003/0130680 A1 | 7/2003 | Russell |
| 2003/0139765 A1 | 7/2003 | Patel et al. |
| 2003/0153945 A1 | 8/2003 | Patel et al. |
| 2003/0163159 A1 | 8/2003 | Patel et al. |

(56) References Cited

U.S. PATENT DOCUMENTS

| | | |
|---|---|---|
| 2003/0171771 A1 | 9/2003 | Anderson et al. |
| 2003/0176884 A1 | 9/2003 | Berrada et al. |
| 2003/0176888 A1 | 9/2003 | O'Connell |
| 2003/0191516 A1 | 10/2003 | Weldon et al. |
| 2003/0195554 A1 | 10/2003 | Shen et al. |
| 2003/0195556 A1 | 10/2003 | Stack et al. |
| 2003/0199918 A1 | 10/2003 | Patel et al. |
| 2003/0208227 A1 | 11/2003 | Thomas |
| 2003/0208253 A1 | 11/2003 | Beyer et al. |
| 2004/0006364 A1 | 1/2004 | Ladd |
| 2004/0059373 A1 | 3/2004 | Shapiro et al. |
| 2004/0068288 A1 | 4/2004 | Palmer |
| 2004/0073252 A1 | 4/2004 | Goldberg et al. |
| 2004/0082966 A1* | 4/2004 | WasDyke .............. 606/200 |
| 2004/0087999 A1 | 5/2004 | Bosma et al. |
| 2004/0088000 A1 | 5/2004 | Muller |
| 2004/0088001 A1 | 5/2004 | Bosma et al. |
| 2004/0088002 A1 | 5/2004 | Boyle et al. |
| 2004/0093015 A1 | 5/2004 | Ogle |
| 2004/0116959 A1 | 6/2004 | McGuckin, Jr. et al. |
| 2004/0138693 A1 | 7/2004 | Eskuri et al. |
| 2004/0153110 A1 | 8/2004 | Kurz et al. |
| 2004/0153118 A1 | 8/2004 | Clubb et al. |
| 2004/0153119 A1 | 8/2004 | Kusleika et al. |
| 2004/0158273 A1 | 8/2004 | Weaver et al. |
| 2004/0158274 A1 | 8/2004 | WasDyke |
| 2004/0167568 A1 | 8/2004 | Boyle et al. |
| 2004/0172042 A1 | 9/2004 | Suon et al. |
| 2004/0176672 A1 | 9/2004 | Silver et al. |
| 2004/0186510 A1 | 9/2004 | Weaver |
| 2004/0186512 A1 | 9/2004 | Bruckheimer et al. |
| 2004/0193209 A1 | 9/2004 | Pavcnik et al. |
| 2004/0199240 A1 | 10/2004 | Dorn |
| 2004/0199270 A1 | 10/2004 | Wang |
| 2004/0220425 A1 | 11/2004 | Kreidler et al. |
| 2004/0220611 A1 | 11/2004 | Ogle |
| 2004/0230220 A1 | 11/2004 | Osborne |
| 2004/0243173 A1 | 12/2004 | Inoue |
| 2005/0015111 A1 | 1/2005 | McGuckin, Jr. et al. |
| 2005/0019370 A1 | 1/2005 | Humes |
| 2005/0021075 A1 | 1/2005 | Bonnette et al. |
| 2005/0021076 A1 | 1/2005 | Mazzocchi et al. |
| 2005/0021152 A1 | 1/2005 | Ogle et al. |
| 2005/0027314 A1 | 2/2005 | WasDyke |
| 2005/0055045 A1 | 3/2005 | DeVries et al. |
| 2005/0055046 A1 | 3/2005 | McGuckin, Jr. et al. |
| 2005/0080447 A1 | 4/2005 | McGuckin, Jr. et al. |
| 2005/0080449 A1 | 4/2005 | Mulder |
| 2005/0085847 A1 | 4/2005 | Galdonik et al. |
| 2005/0090858 A1 | 4/2005 | Pavlovic |
| 2005/0131451 A1 | 6/2005 | Kleshinski et al. |
| 2005/0159771 A1 | 7/2005 | Peterson |
| 2005/0182439 A1 | 8/2005 | Lowe |
| 2005/0222604 A1 | 10/2005 | Schaeffer |
| 2005/0288703 A1 | 12/2005 | Beyer et al. |
| 2005/0288704 A1 | 12/2005 | Cartier et al. |
| 2006/0004402 A1 | 1/2006 | Voeller et al. |
| 2006/0015137 A1 | 1/2006 | WasDyke et al. |
| 2006/0036279 A1 | 2/2006 | Eidenschink et al. |
| 2006/0041271 A1 | 2/2006 | Bosma et al. |
| 2006/0069405 A1 | 3/2006 | Schaeffer et al. |
| 2006/0069406 A1 | 3/2006 | Hendriksen et al. |
| 2006/0079928 A1 | 4/2006 | Cartier et al. |
| 2006/0079930 A1 | 4/2006 | McGuckin, Jr. et al. |
| 2006/0095068 A1 | 5/2006 | WasDyke et al. |
| 2006/0203769 A1 | 9/2006 | Saholt et al. |
| 2006/0206138 A1 | 9/2006 | Eidenschink |
| 2006/0259067 A1 | 11/2006 | Welch et al. |
| 2006/0259068 A1 | 11/2006 | Eidenschink |
| 2007/0005095 A1 | 1/2007 | Osborne et al. |
| 2007/0005104 A1 | 1/2007 | Kusleika et al. |
| 2007/0005105 A1 | 1/2007 | Kusleika et al. |

FOREIGN PATENT DOCUMENTS

| | | |
|---|---|---|
| EP | 1 092 401 A1 | 4/2001 |
| EP | 1 336 393 A2 | 8/2003 |
| EP | 1 475 110 A1 | 11/2004 |
| FR | 2570288 A1 | 3/1986 |
| FR | 2718950 A1 | 10/1995 |
| FR | 2 781 143 A1 | 1/2000 |
| FR | 2 791 551 A1 | 10/2000 |
| WO | WO-97/29794 A1 | 8/1997 |
| WO | WO-00/56390 A1 | 9/2000 |
| WO | WO-02/055125 A2 | 7/2002 |
| WO | WO-03/003927 A1 | 1/2003 |
| WO | WO-03/004074 A3 | 1/2003 |
| WO | WO-2004/012587 A2 | 2/2004 |
| WO | WO-2005/009214 A2 | 2/2005 |

OTHER PUBLICATIONS

Ashley, D. W. et al., "Accurate Deployment of Vena Cava Filters: Comparison of Intravascular Ultrasound and Contrast Venography", The Journal of Trauma: Injury, Infection, and Critical Care, Jun. 2001, vol. 50, No. 6, pp. 975-981.

Authors' Abstract, Journal of Vascular and Interventional Radiology, Oct. 2002, 13(10):1062-1068.

Critical Care Medicine, vol. 32, No. 12 (Suppl.), pp. A181-A188.

Doherty, C., "Special Problems of Massive Obesity", Primary Care Physician's Resource Center, file://D:§Special%20Problems%20of%20Massive%20Obesity.htm, retrieved Jul. 26, 2005.

Gosin, J. S., "Efficacy of Prophylactic Vena Cava Filters in High-Risk Trauma Patients", Annals of Vascular Surgery, 1997, 11:100-105.

Greenfield, L. J., "Does Cervical Spinal Cord Injury Induce a Higher Incidence of Complications After Prophylactic Greenfield Filter Usage?", Journal of Vascular and Interventional Radiology, Jul.-Aug. 1997, pp. 719-720.

Ha, T. G. Van et al., "Removal of Gunther Tulip Vena Cava Filter Through Femoral Vein Approach", Journal of Vascular and Interventional Radiology, 2005, 16:391-394.

Letters to the Editor, Journal of the American College of Surgeons, Mar. 1996, vol. 182, pp. 279-280.

Miller, A. C., "British Thoracic Society Guidelines for the Management of Suspected Acute Pulmonary Embolism", Thorax, Jun. 2003, 58(6): 470-483.

Millward, S., "Temporary IVC Filtration Before Patent Foramen Ovale Closure in a Patient With Paradoxic Embolism", Letter to the Editor, p. 937.

Natta, T. L. Van et al., "Elective Bedside Surgery in Critically Injured Patients is Safe and Cost-Effective", American Surgery, May 1998, 227(5):618-626.

Oppat, W. F. et al., "Intravascular Ultrasound-Guided Vena Cava Filter Placement", Journal of Endovascular Surgery, 1999, 6:285-287.

Participants in the Vena Caval Filter Consensus Conference, Recommended Reporting Standards for Vena Caval Filter Placement and Patient Follow-Up, Journal of Vascular Surgery, Sep. 1999, 30(3):573-579.

Poster: Clinical Science: Pulmonary Disease or Dysfunctional/Mechanical Ventilation/Weaning (Adult, Critical Care Medicine, vol. 32, No. 12 (Suppl.), pp. A111-A120.

Rogers, F. B. et al., "Five-Year Follow-Up of Prophylactic Vena Cava Filters in High-Risk Trauma Patients", Archives of Surgery, Apr. 1998, 133:406-411.

Rogers, F. B. et al., "Practice Management Guidelines for the Prevention of Venous Thromboembolism in Trauma Patients: The EAST Practice Management Guidelines Work Group", The Journal of Trauma; Injury, Infection, and Critical Care, Jul. 2002, 53:142-164.

Rogers, F. B. et al., "Prophylactic Vena Cava Filter Insertion in Severely Injured Trauma Patients: Indications and Preliminary Results", The Journal of Trauma, Oct. 1993, 35(4):637-642.

Rogers, F. B. et al., "Prophylactic Vena Cave Filter Insertion in Selected High-Risk Orthopaedic Trauma Patients", Journal of Orthopaedic Trauma, 1997, 11(4):267-272.

(56) References Cited

OTHER PUBLICATIONS

Rogers, F. B. et al., "Routine Prophylactic Vena Cava Filter Insertion in Severely Injured Trauma Patients Decreases the Incidence of Pulmonary Embolism", Journal of the American College of Surgeons, Jun. 1995 180(6):641-647.

Rogers, F. B., "Venous Thromboembolism in Trauma Patients: A Review", Surgery, Jul. 2001, vol. 130, No. 1, pp. 1-12.

Rohrer, M. J. et al., "Extended Indications for Placement of an Inferior Vena Cava Filter", Journal of Vascular Surgery, Jul. 1989, vol. 10. No. 1, pp. 44-50.

Rose, S. C. et al., "Placement of Inferior Vena Caval Filters in the Intensive Care Unit", Journal of Vascular and Interventional Radiology, 1997, 8:61-64.

Rose, S. C. et al., "Regarding "Bedside Vena Cava Filter Placement Guided With Intravascular Ultrasound"", Journal of Vascular Surgery, Apr. 2002, vol. 35, No. 4.

Rossi, G. et al., "Open to Critique: An Unusual Complication of Vena Cava Filter Placement", Journal of Vascular Surgery, Nov. 1996, vol. 24, No. 5.

Rubin, B. G. et al., "Care of Patients With Deep Venous Thrombosis in an Academic Medical Center: Limitations and Lessons", Journal of Vascular Surgery, 1994, 20:698-704.

Ruiz, A. J. et al., "Heparin, Deep Venous Thrombosis, and Trauma Patients", The American Journal of Surgery, Aug. 1991, 162:159-162.

Ryskamp, R. P. et al., "Utilization of Venous Thromboembolism Prophylaxis in a Medical-Surgical ICU", Chest. Jan. 1998, 113(1)162-164.

Sapala, J. A. et al., "Fatal Pulmonary Embolism After Bariatric Operations for Morbid Obesity: A 24-Year Retrospective Analysis", Obesity Surgery, 2003, 13:819-825.

Sarasin, F. P. et al., "Management and Prevention of Thromboemboli in Patients With Cancer-Related Hypercoagulable", Journal of General Internal Medicine, Sep. 1993, 8:476-485.

Schultz, D. J. et al., "Incidence of Asymptomatic Pulmonary Embolism in Moderately to Severely Injured Trauma Patients", Journal of Trauma: Injury Infection, and Critical Care, 2004, 56:727-733.

Shackford, S. R. et al., "Venous Thromboembolism in Patients With Major Trauma", The American Journal of Surgery, Apr. 1990, vol. 1 59, pp. 365-369.

Shaer, J. et al., "An Unusual Cause of Low Back Pain?: A Case Report", Spine, Jun. 15, 1998, 23(12):1349-1350.

Sharpe, R. P. et al., "Incidence and Natural History of Below-Knee Deep Venous Thrombosis in High-Risk Trauma Patients", The Journal of Trauma: Injury, Infection, and Critical Care, Dec. 2002, 53:1048-1052.

Sheikh, M. A. et al., "Images in Vascular Medicine", Vascular Medicine 2001, 6:63-64.

Sheikh, M. A. et al., "Isolated Internal Jugular Vein Thrombosis: Risk Factors and Natural History", Vascular Medicine, 2002, 7:177-179.

Siddique, R. M. et al., "Thirty-Day Case-Fatality Rates for Pulmonary Embolism in the Elderly", Archives of Internal Medicine, Nov. 11, 1996, 156:2343-2347.

Simon, M. et al., "Comparative Evaluation of Clinically Available Inferior Vena Cava Filters With an in Vitro Physiologic Simulation of the Vena Cava", Radiology, 1993, 189:769-774.

Simon, M. et al., "Paddle-Wheel CT Display of Pulmonary Arteries and Other Lung Structures: A New Imaging Approach", American Journal of Roentgenology, Jul. 2001, pp. 195-198.

Simon, M., "Vena Cava Filters: Prevalent Misconceptions", Journal of Vascular and Interventional Radiology, 1999, 10:1021-1024.

Simon,M. et al., "A Vane Cava Filter Using Thermal Shape Memory Alloy", Radiology, Oct. 1977, 125:89-94.

Sing, R. F. et al., "Bedside Carbon Dioxide ($CO_2$) Preinsertion Cavagram for Inferior Vena Cava Filter Placement: Case Report", Journal of Trauma, Dec. 1999, 47(6):1140-1142.

Sing, R. F. et al., "Bedside Carbon Dioxide Cavagrams for Inferior Vena Cava Filters: Preliminary Results", Journal of Vascular Surgery, 2000, 32:144-147.

Sing, R. F. et al., "Bedside Insertion of Inferior Vena Cava Filters in the Intensive Care Unit", Journal of Trauma, Dec. 1999, 47(6):1104-1109.

Sing, R. F. et al., "Bedside Insertion of Inferior Vena Cava Filters in the Intensive Care Unit", Journal of American College of Surgeons, May 2001, 192(5):570-575.

Sing, R. F. et al., "Bedside Insertion of the Inferior Vena Cava Filter in the Intensive Care Unit", The American Surgeon, Aug. 2003, 69:660-662.

Sing, R. F. et al., "Guidewire Incidents With Inferior Vena Cava Filters", JAOA, Apr. 2001, 101(4):231-233.

Sing, R. F. et al., "Preliminary Results of Bedside Inferior Vena Cava Filter Placement", Chest, Jul. 1998, 114(1):315.

Sing, R. F. et al., "Regarding" Bedside Vena Cava Filter Placement Guided With Intravascular Ultrasound, Journal of Vascular Surgery, May 2002, vol. 25, No. 5.

Smith, T. P. et al., "Acute Pulmonary Thromboembolism-Comparison of the Diagnostic Capabilities of Convention Film-Screen and Digital Angiography", Chest, 2002, 122:968-972.

Smith, T. P., "Pulmonary embolism: What's Wrong With This Diagnosis", American Journal of Roentgenology, Jun. 2000, 174:1489-1498.

Spain, D. A. et al., "Venous Thromboembolism in the High-Risk Trauma Patient: Do Risks Justify Aggressive Screening and Prophylaxis?", The Journal of Trauma: Injury, Infection, and Critical Care, 1997, vol. 42, No. 3, pp. 463-469.

Stavropoulos, S. W. et al.. "In Vitro Study of Guide Wire Entrapment in Currently Available inferior Vena Cava Filters", Journal of Vascular and Interventional Radiology, 2003, 14:905-910.

Stecker, M. S. et al., "Evaluation of a Spiral Nitinol Temporary Inferior Vena Caval Filter", Academic Radiology, 2001, 8:484-493.

Stein, P. D. et al., "Deep Venous Thrombosis in a General Hospital", Chest, 2002, 122:960-962.

Stein, P. D., "Opinions Regarding the Diagnosis and Management of Venous Thromboembolic Disease", Chest, Feb. 1998, vol. 113, No. 2, pp. 499-504.

Still, J. et al., "Experience With the Insertion of Vena Caval Filters in Acutely Burned Patients", The American Surgeon, Mar. 2000, vol. 66, No. 3, pp. 277-279.

Stover, M. D. et al., "Prospective Comparison of Contrast-Enhanced Computed Tomography Versus Magnetic Resonance Venography in the Detection of Occult Deep Pelvic Vein Thrombosis in Patients With Pelvic and Acetabular Fractures", Journal of Orthopaedic Trauma, 2002, 16(9):613-621.

Streib, E. W. et al., "Complications of Vascular Access Procedures in Patients With Vena Cava Filters", The Journal of Trauma: Injury Infection, and Critical Care, Sep. 2000, vol. 49, No. 3, pp. 553-558.

Sue, L. P. et al., "Iliofemoral Venous Injuries: An Indication for Prophylactic Caval Filter Placement", The Journal of Trauma: Injury, Infection, and Critical Care, 1995, vol. 39, No. 4, pp. 693-695.

Sugerman, H. J. et al., "Risks and Benefits of Gastric Bypass in Morbidity Obese Patients With Severe Venous Stasis Disease", Annals of Surgery, 2001, vol. 234, No. 1, pp. 41-46.

Sultan, S. et al., "Operative and Endovascular Management of Extracranial Vertebral Artery Aneurysm in Ehlers-Danlos Syndrome: A Clinical Dilemma", Vascular and Endovascular Surgery, 2002, 36(5):389-392.

Tai, N. R. M. et al., "Modern Management of Pulmonary Embolism", British Journal of Surgery, 1999, 86:853-868.

Thomas, J. H. et al., "Vena Caval Occlusion After Bird's Nest Filter Placement", American Journal or Surgery, Dec. 1998, vol. 176, pp. 598-600.

Thomas, L. A. et al., "Use of Greenfield Filters in Pregnant Women at Risk for Pulmonary Embolism", Southern Medical Journal, Feb. 1997, vol. 90, Issue 2.

Tillie-Leblond, I. et al., "Risk of Pulmonary Embolism After a Negative Spiral CT Angiogram in Patients With Pulmonary Disease: 1-Year Clinical Follow-Up Study", Radiology, 2002, 223:461-467.

Tips From Other Journals, American Family Physician, Feb. 1, 2003, vol. 67, No. 3, p. 593.

Tola, J. C. et al., "Bedside Placement of Inferior Vena Cava Filters in the Intensive Care Unit", The American Surgeon, Sep. 1999, vol. 65, No. 9, pp. 833-838.

(56) References Cited

OTHER PUBLICATIONS

Tovey, C. et al., "Diagnosis, Investigation, and Management of Deep Vein Thrombosis", British Medical Journal, May 31, 2003, vol. 326, i7400, p. 1180(5), 9 pages.
Trerotola, S. O. et al., "Preclinical in Vivo Testing of the Arrow-Trerotola Percutaneous Thrombolytic Device for Venous Thrombosis", Journal of Vascular and Interventional Radiology, 2001, 12:95-103.
Trujillo-Santos,J. et al., "Bed Rest or Ambulation in the Initial Treatment of Patients With Acute Deep Vein Thrombosis or Pulmonary Embolism", Chest, 2005, 127:1631-1636.
Tuna, I. C. et al., "Massive Pulmonary Embolus", Texas Heart Institute Journal, 2002, vol. 29, No, 2, pp. 144-145.
Urena, R. et al., "Bird's Nest Filter Migration to the Right Atrium", American Journal of Roentgenology, Oct. 2004, 183:1037-1039.
Valji, K., "Evolvin Strategies for Thrombolytic Therapy of Peripheral Vascular Occlusion", Journal of Vascular and Interventional Radiology, 2000, 11:411-420.
Vedantham, S. et al., "Endovascular Recanalization of the Thrombosed Filter-Bearing Inferior Vena Cava", Journal of Vascular and Interventional Radiology, 2003, 14:893-903.
Vedantham, S. et al., "Lower Extremity Venous Thrombolysis With Adjunctive Mechanical Thrombectomy", Journal of Vascular and Interventional Radiology, 2002, 13:1001-1008.
Vedantham, S. et al., "Pharmacomechanical Thrombolysis and Early Stent Placement for Iliofemoral Deep Vein Thrombosis", Journal of Vascular and Interventional Radiology, 2004, 15:565-574.
Velmahos, G. C. et al., "Inability of an Aggressive Policy of Thromboprophylaxis to Prevent Deep Venous Thrombosis (DVT) in Critically Injured Patients: Are Current Methods of DVT Prophylaxis Insufficient?", Journal of the American College of Surgeons, 1998, 187:529-533.
Velmahos, G. C. et al., "Prevention of Venous Thromboembolism After Injury: An Evidence-Based Report—Part 1: Analysis of Risk Factors and Evaluation of the Role of Vena Caval Filters", The Journal of Trauma: Injury, Infection, and Critical Care, Jul. 2000, 49:132-139.
Velmahos, G. C. et al., "Prevention of Venous Thromboembolism After Injury: An Evidence-Based Report—Part II: Analysis of Risk Factors and Evaluation of the Role of Vena Caval Filters", The Journal of Trauma: Injury, Infection, and Critical Care, Jul. 2000, 49:140-144.
Velmahos, G. C. et al., "Spiral Computed Tomography for the Diagnosis of Pulmonary Embolism in Critically Ill Surgical Patients", Archives of Surgery, May 2001, 136(5):505-511.
Venbrux, Anthony C., "Protection Against Pulmonary Embolism: Permanent and Temporary Caval Filters" Department of Radiology-CVDL, The Johns Hopkins Medical Institutions, Baltimore MD, 7 pages.
Vesely, T. M. et al., "Preliminary Investigation of the Irie Inferior Vena Gavel Filter", Journal of Vascular and Interventional Radiology, 1996, 7:529-535.
Vorwerk, D. et al., "Use of a Temporary Caval Filter to Assist Percutaneous Iliocaval Thrombectomy: Experimental Results", Journal of Vascular and Interventional Radiology, Sep.-Oct. 1995, 6(5):737-740.
Vrachliotis, T. G. et al., "Percutaneous Management of Extensive Clot Trapped in a Temporary Vena Cava Filler", Journal of Endovascular Therapy, 2003, 10:1001-1005.
Wakefield, T. W., Treatment Options for Venous Thrombosis, Journal of Vascular Surgery, Mar. 2000, 31(3):613-620.
Wallace, M. J., "Transatrial Stent Placement for Treatment of Inferior Vena Cava Obstruction Secondary to Extension of Intracardiac Tumor Thrombus From Hepatocellular Carcinoma", Journal of Vascular Interventional Radiology, 2003, 14:1339-1343.
Wang, W. Y. et al., "Use of a Nitinol Gooseneck Snare to Open an Incompletely Expanded Over-the-Wire Stainless Steel Greenfield Filter", American Journal of Roentgenology, Feb. 1999, 172:499-500.

Watanabe, N. et al., "Images in Cardiology: Large Thrombus Entrapped in a Patient Foramen Ovale of the Atrial Septum, Which Apparently "Disappeared" Without Embolic Events", Heart, Nov. 2002, 88(5):474.
Watanabe, S. et al., "Superior Vena Caval Placement of a Temporary Filter: A Case Report", Vascular Surgery, Jan./Feb. 2001, vol. 35, Issue 1.
Welch, H. J. et al., "Duplex Assessment of Venous Reflux and Chronic Venous Insufficiency: The Significance of Deep Venous Reflux", Journal of Vascular Surgery, 1996, 24:755-762.
Wellons, E. D. et al., "Bedside Intravascular Ultrasound-Guided Vena Cava Filter Placement", Journal of Vascular Surgery, 2003, 38:455-458.
Wells, J. L. et al., "Diagnosing Pulmonary Embolism; A Medical Masquerader", Clinician Reviews, 2001, 11(2):66-79.
Westling, A. et al., "Incidence of Deep Venous Thrombosis in Patients Undergoing Obesity Surgery", World Journal of Surgery, 2002, 26:470-473.
White, R. H. et al., "A Population-Based Study of the Effectiveness of Inferior Vena Cava Filter Use Among Patients With Venous Thromboembolism", Archives of Internal Medicine, Jul. 10, 2000, 160(13):2033-2041.
Whitehill, T. A., "Current Vena Cava Filter Devices and Results", Seminars in Vascular Surgery, Sep. 2000, 13(3):204-212.
Wholey, M. et al., "Technique for Retrieval of a Guidewire Lodged in a Vena Cava Filter", Vascular and Endovascular Surgery, 2002, 36(5):385-387.
Wiles, C. E., Letters to Editor, Journal of Trauma, Aug. 1999, 47(2):438.
Wilson, J. T. et al., "Prophylactic Vena Cava Filter Insertion in Patients With Traumatic Spinal Cord Injury: Preliminary Results", Neurosurgery, 1994, 35:234-239.
Winchell, R. J. et al., "Risk Factors Associated With Pulmonary Embolism Despite Routine Prophylaxis: Implications for Improved Protection", The Journal of Trauma, 1994, 37(4):600-606.
Wittenberg, G. et al., "Long-Term Results of Vena Cava Filters: Experiences With the LGM and the Titanium Greenfield Devices", Cardiovascular and Interventional Radiology, 1998, 21:225-229.
Wittich, G. R. et al., "Anchoring a Migrating Inferior Vena Cava Stent With Use of a T-Fastener", Journal of Vascular and Interventional Radiology, 2001, 12:994-996.
Wojcik, R. et al., "Long-Term Follow-Up of Trauma Patients With a Vena Caval Filter", The Journal of Trauma: Injury, Infection, and Critical Care, Nov. 2000, 49(5):639-843.
Wojtowycz, M. M. et al., "The Bird's Nest Inferior Vena Caval Filter: Review of a Single-Center Experience", Journal of Vascular and Interventional Radiology, 1997, 8:171-179.
Woodward, E. B. et al., "Delayed Retroperitoneal Arterial Hemorrhage After Inferior Vena Cava (IVC) Filter Insertion: Case Report and Literature Review of Caval Perforations by IVC Filters", Annals of Vascular Surgery, 2002, 16:193-196.
Xian, Z. Y. et al., "Multiple Emboli and Filter Function: An in Vitro Comparison of Three Vena Cava Filters", Journal of Vascular and Interventional Radiology, 1995, 6:887-893.
Xu, X. Y. et al., "Flow Studies in Canine Artery Bifurcations Using a Numerical Simulation Method", Journal of Biochemical Engineering, Nov. 1992, 114:504-511.
Yagi, A. et al., "Pulmonary Thromboembolism Evaluating the Indication and Effect of a Vena Caval Filter With Indium-111-Platelet Scintigraphy", Circulation Journal, Jun. 2004, 68:599-601.
Yonezawa, K. et al., "Effectiveness of an Inferior Vena Cava Filter as a Preventive Measure Against Pulmonary Thromboembolism After Abdominal Surgery", Surgery Today, 1999, 29:821-824.
Yucel, E. Kent, "Pulmonary MR Angiography: Is It Ready Now?", Radiology, 1999, 210:301-303.
Zamora, C. A. et al., "Prophylactic Stenting of the Inferior Vena Cava Before Transcatheter Embolization of Renal Cell Carcinomas: An Alternative to Filter Placement", Journal of Endovascular Therapy, 2004, 11:84-88.
Zanchetta, M. et al., "A New Permanent and Retrievable Vena Cava Filter: Its Removal After Five Months", Italian Heart Journal, Sep. 2001, 2(9):715-716.

(56) References Cited

OTHER PUBLICATIONS

Zeni, P. T. et al., "Use of Rheolytic Thrombectomy in Treatment of Acute Massive Pulmonary Embolism", Journal of Vascular and Interventional Radiology, 2003, 14:1511-1515.

Zinzindohoue, F. et al., "Laparoscopic Gastric Banding: A Minimally Invasive Surgical Treatment for Morbid Obesity—Prospective Study of 500 Consecutive Patients", Annals of Surgery, 2003, 237(1):1-9.

Adams, E. et al., "Retrievable Inferior Vena Cava Filter for Thrombolic Disease in Pregnancy", British Journal of Obstetrics and Gynaecology, Sep. 1998, vol. 105, pp. 1039-1042.

Authors' Abstract, "Abstracts of Current Literature", Journal of Vascular and Interventional Radiology, Mar. 2000, vol. 11, No. 3, pp. 402-407.

Consensus Conference, "Prevention of Venous Thrombosis and Pulmonary Embolism", JAMA, Aug. 8, 1986, vol. 256, No. 6, pp. 744-749.

Hirsch, D. R. et al., "Prevalence of Deep Venous Thrombosis Among Patients in Medical Intensive Care", JAMA, Jul. 28, 1995, 274(4):335337.

Hirsch, S. B. et al., Case Reports: Accidental Placement of the Greenfield Filter in the Heart: Report of Two Cases et al., Journal of Vascular Surgery, Dec. 1987, vol. 6, No. 6.

Hoff, W. S. et al., "Early Experience With Retrievable Inferior Vena Cava Filters in High-Risk Trauma Patients", Journal of the American College of Surgeons, Dec. 2004, vol. 199, No. 6, pp. 869-874.

Hyers, T. M. et al., "Antithrombotic Therapy for Venous Thromboembolic Disease", Chest, Jan. 2001, 119(1):176S-193S.

Ihnat, D. M. et al., "Treatment of Patients With Venous Thromboembolism and Malignant Disease: Should Vena Cava Filter Placement Be Routine?", Journal of Vascular Surgery, Nov. 1998, vol. 28, No. 8, pp. 800-807.

Inge, T. H. et al.. "Bariatric Surgery for Severely Overweight Adolescents: Concerns and Recommendations", Pediatrics, Jul. 2004, vol. 114, No. 1, pp. 217-223.

Izutani, H. el al., "Migration of an Inferior Vena Cava Filter to the Right Ventricle and Literature Review", Can J Cardiol, Feb. 2004, vol. 20, No. 2, pp. 233-235.

Jacobs, D. G. et al., "The Role of Vena Caval Filters in the Management of Venous Thromboembolism" The American Surgeon, Aug. 2003, vol. 69, No. 8, pp. 635-642.

Jacobs, D. G. et al., Letters to the Editor, The Journal of Trauma, Dec. 1997, vol. 43, No. 6, pp. 988-989.

Jain, V. et al., "Preoperative Vena Caval Interruption for Venous Thrombosis Associated With Ovarian Malignancy", Acta Obstetricia Et Gynecologica Scandinavica.

Jarrett B.P. et al., Inferior Vena Cava Filters in Malignant Disease, Journal of Vascular Surgery, 2002, 36:704-707.

Joels, C. S. et al., "Complications of Inferior Vena Cava Filters", The American Surgeon, Aug. 2003, vol. 69, No. 8, pp. 654-659.

Jones K. V. et al., "Tricuspid Insufficiency After Intracardiac Migration of a Greenfield Filter: Case Report and Review of the Literature", Journal of Vascular Surgery, Sep. 1996, vol. 24, No. 3, pp. 494-498.

Kellum, J. M., "Gastric Banding" Annals of Surgery, Jan. 2003, vol. 237, No. 1, pp. 17-18.

Kelly, J. et al., "Anticoagulation or Inferior Vena Cava Filter Placement for Patients With Primary Intracerebral Hemorrhage Developing Venous Thromboembolism?", Stroke, 2003, 34:2999-3005.

Kerr, A. et al., "Bidirectional Vena Cava Filter Placement"; Journal of Vascular Surgery, Oct. 1995, vol. 22, No. 4.

Khansarinia, S. et al., Prophylactic Greenfield Filter Placement in Selected High-Risk Trauma Patients, Journal of Vascular Surgery, 1995, 22:231-236.

Kim, D. et al., "Insertion of the Simon Nitinol Caval Filter: Value of the Antecubital Vein Approach", American Journal of Roentgenology, Sep. 1991, 157:521-522.

Kim, J. et al., "Preliminary Report on the Safety of Heparin for Deep Venous Thrombosis Prophylaxis After Severe Head Injury", The Journal of Trauma: Injury, Infection, and Critical Care, Jul. 2002, vol. 53, No. 1, pp. 38-43.

Kim, V. et al., "Epidemiology of Venous Thromboembolic Disease", Emergency Medicine Clinics of North America, Nov. 2001, vol. 19, No. 4, pp. 839-859.

Kimmerly, W. S. et al., "Graduate Surgical Trainee Attitudes Toward Postoperative Thromboprophylaxis", Southern Medical Journal, Aug. 1999, vol. 92, No. 9, pp. 790-794.

Kinney, T. B. et al., "Does Cervical Spinal Cord Injury Induce a Higher Incidence of Complications After Prophylactic Greenfield Inferior Vena Cava Filter Usage?", Journal of Vascular and Interventional Radiology, 1996, 7:907-915.

Kinney, T. B. et al., "Regarding "Limb Asymmetry in Titanium Greenfield Filters: Clinically Significant?"", Journal of Vascular Surgery, Jun. 1998, vol. 27, No. 6.

Kistner, R. L., Definitive Diagnosis and Definitive Treatment in Chronic Venous Disease: A Concept Whose Time Has Come:, Journal of Vascular Surgery, Nov. 1998, vol. 24, No. 5, pp. 703-710.

Knudson, M. M. et al., "Prevention of Venous Thromboembolism in Trauma Patients", The Journal of Trauma, Sep. 1994, vol. 37, No. 3, pp. 480-487.

Knudson, M. M. et al., "Thromboembolism After Trauma—An Analysis of 1602 Episodes From the American College of Surgeons National Trauma Data Bank" Annals of Surgery, Sep. 2004, vol. 240, No. 3, pp. 490-498.

Knudson, M. M. et al., Thromboembolism Following Multiple Trauma, The Journal of Trauma, Jan. 1992, vol. 32, No. 1, pp. 2-11.

Knudson, M. M. et al., "Venous Thromboembolism After Trauma", Current Opinion in Critical Care, 2004, 10:539-548.

Koga, F. et al., "Deep Vein Thrombosis During Chemotherapy in a Patient With Advanced Testicular Cancer: Successful Percutaneous Thrombectomy Under Temporary Placement of Retrievable Inferior Vena Cava Filter", International Journal of Uroloty, 2001, 8:90-93.

Konya, A. et al., "New Embolization Coil Containing a Nitinol Wire Core: Preliminary in Vitro and in Vivo Experiences", Journal of Vascular and Interventional Radiology, 2001, 12:869-877.

Kreutzer J.et al., "Healing Response to the Clamshell Device for Closure of Intracardiac Defects in Humans", Catheterization and Cardiovascular Interventions, 2001, vol. 54.

Kudsk, K. A. et al., "Silent Deep Vein Thrombosis in Immobilized Multiple Trauma Patients", The American Journal of Surgery, Dec. 1989, vol. 158, pp. 515-519.

Kyrle, P. A. et al., Deep Vein Thrombosis, The Lancet, Mar. 26-Apr. 1, 2005, 365(9465):1163-1174.

Langan III, E. M. et al., "Prophylactic Inferior Vena Cava Filters in Trauma Patients at High Risk: Follow-Up Examination and Risk/Benefit Assessment", Journal of Vascular Surgery, 1999, 30:484-490.

Leach, T. A. et al., "Surgical Prophylaxis for Pulmonary Embolism", The American Surgeon, Apr. 1994, vol. 60, No. 4, pp. 292-295.

Leoni, C. J. et al., "Classifying Complications of Interventional Procedures: A Survey of Practicing Radiologists", Journal of Vascular and Interventional Radiology, 2001, 12:55-59.

Letai, A., "Cancer, Coagulation, and Anticoagulation", The Oncologist, 1999, 4:443-449.

Lewis-Carey, M. B. et al., "Temporary IVC Filtration Before Patent Foramen Ovale Closure in a Patient With Paradoxic Embolism", Journal of Vascular and Interventional Radiology, 2002, 13:1275-1278.

Lidagoster, M. I. et al., Superior Vena Cava Occlusion After Filter Insertion, Journal of Vascular Surgery, Jul. 1994, vol. 20, No. 1.

Lin, J. et al., "Factors Associated With Recurrent Venous Thromboembolism in Patients With Malignant Disease", Journal of Vascular Surgery, 2003, 37:976-983.

Lin, P. H. et al., "The Regained Referral Ground and Clinical Practice of Vena Cava Filter Placement in Vascular Surgery", The American Surgeon, Oct. 2002, vol. 68, No. 10, pp. 865-870.

Linsenmaier U. et al, "Indications, Management, and Complications of Temporary Inferior Vena Cava Filters", Cardiovascular and Interventional Radiology, 1998, 21:464-469.

Lopez-Beret, P. et al., "Systematic Study of Occult Pulmonary Thromboembolism in Patients With Deep Venous Thrombosis", Journal of Vascular Surgery, 2001, 33:515-521.

Lorch, H. et al., "In Vitro Studies of Temporary Vena Cava Filters", Cardiovascular and Interventional Radiology, 1996, 21:146-150.

(56) References Cited

OTHER PUBLICATIONS

Lujan, J. A. et al., "Laparoscopic Versus Open Gastric Bypass in the Treatment of Morbid Obesity", Annals of Surgery, Apr. 2004, vol. 239. No. 4, pp. 433-437.

Luo, X. Y. et al., "Non-Newtonian Flow Patterns Associated With an Arterial Stenosis", Journal of Biomechanical Engineering, Nov. 1992, 114:512-514.

MacDonald, K. G. Jr., "Overview of the Epidemiology of Obesity and the Early History of Procedures to Remedy Morbid Obesity", Archives of Surgery, Apr. 2003, 138(4):357-360.

Manke, C. et al., "MR Imaging-Guided Stant Placement in Iliac Arterial Stenoses: A Feasibility Study", Radioilogy, 2001, 219:527-534.

Matthews, B. D. et al., "Inferior Vena Cava Filter Placement: Preinsertion Inferior Vena Cava Imaging", The American Surgeon, Aug. 2003, vol. 69, No. 8, pp. 649-653.

Mortele, K. J. et al., "The Swedish Laparoscopic Adjustable Gastric Banding for Morbid Obesity: Radiologic Findings in 218 Patients", American Journal of Roentgenology, 2001, 177:77-84.

Murakami, M. et al., "Deep Venous Thrombosis Prophylaxis in Trauma: Improved Compliance With a Novel Miniaturized Pneumatic Compression Device", Journal of Vascular Surgery, 2003, 38:923-927.

Nakagawa, N. et al., "A Retrievable Nitinol Vena Cava Filter: Experimental and Initial Clinical Results", Journal of Vascular and Interventional Radiology, 1994, 5:507-512.

Napolitano, L. M. et al., "Asymptomatic Deep Venous Thrombosis in the Trauma Patient: Is an Aggressive Screening Protocol Justified?", The Journal of Trauma: Injury, Infection, and Critical Care, 1997, vol. 39, No. 4, pp. 651-659.

Nazario, R. et al., "Treatment of Venous Thromboembolism", Cardiology in Review, 2002, 10(4):249-259.

Neeman, Z. et al., "Metastatic Involvement of a Retrieved inferior Vane Cava Filter", (Clinical Center) and National Cancer Institute, National Institutes of Health, Bethesda, MD), p. 1585.

Neill, A. M. et al., "Retrievable Inferior Vena Caval Filter for Thromboembolic Disease in Pregnancy", British Journal of Obstetrics and Gynaecology, Dec. 1997, vol. 104, pp. 1416-1418.

Neri, E. et al., "Protected Iliofemoral Venous Thrombectomy in a Pregnant Woman With Pulmonary Embolism and Ischemic Venous Thrombosis", Texas Heart Institute Journal, 2002, vol. 29, No. 2, pp. 130-132.

Nguyen, N. T. et al., "A Comparison Study of Laparoscopic Versus Open Gastric Bypass for Morbid Obesity", Journal of the American College of Surgeons, Aug. 2000, vol. 191, No. 2, pp. 149-155.

Nguyen, N. T. et al., "Comparison of Pulmonary Function and Postoperative Pain After Laparoscopic Versus Open Gastric Bypass: A Randomized Trial", Journal of Americal College of Surgeons, 2001, 192:469-477.

Norwood, S. H. et al., "A Potentially Expanded Role for Enoxaparin in Preventing Venous Thromboembolism in High Risk Blunt Trauma Patients", Journal of the American College Of Surgeons, 2001, 192:161-167.

Nunn, C. R. et al., "Cost-Effective Method for Bedside Insertion of Vena Caval Filters in Trauma Patients," The Journal of Trauma, Nov. 1997, vol. 43, No. 5, pp. 752-758.

O'Brien, P. E. et al., "Laparoscopic Adjustable Gastric Banding in the Treatment of Morbid Obesity", Archives of Surgery, Apr. 2003, 138(4):376-382.

O'Malley, K. P. et al., "Prevention of Pulmonary Embolism After Pelvic Fracture: Rational Use of Inferior Vena Caval Filters", (Cooper Hospital/University Medical Center), Jan. 1996, vol. 40.

O'Sullivan, G. J. et al., "Endovascular Management of Iliac Vein Compression (May-Thurner) Syndrome", Journal of Vascular and Interventional Radiology, 2000, 11:823-836.

Offner, P. J. et al., "The Role of Temporary Inferior Vena Cava Filters in Critically Ill Surgical Patients", Archives of Surgery, Jun. 2003, vol. 138, pp. 591-595.

Olearchyk, A. S., "Insertion of the Inferior Vane Cava Filter Followed by Iliofemoral Venous Thrombectomy for Ischemic Venous Thrombosis", Journal of Vascular Surgery, Apr. 1987, vol. 5, No. 4, pp. 645-647.

Olin, J. W., "Pulmonary Embolism", Reviews in Cardiovascular Medicine, 2002, 3(2):S68-S75.

Ornstein, D. L. et al., "Cancer, Thrombosis, and Anticoagulants", Current Opinion in Pulmonary Medicine, 2000, 6:301-308.

Ortega, M. et al., "Efficacy of Anticoagulation Post-Inferior Vena Caval Filter Placement", American Surgeon, May 1998, vol. 64, Issue 5, pp. 419-423.

Ortiz-Saracho, J. et al., "An Unusual Cause of Pulmonary Artery Thrombosis", Chest, 1998, 114:309-310.

Owings, J. T. et al., "Timing of the Occurrence of Pulmonary Embolism in Trauma Patients", Archives of Surgery, Aug. 1997, 132(8):862-867.

Padberg, F. T. et al, "Hemodynamic and Clinical Improvement After Superficial Vein Ablation in Primary Combined Venous Insufficiency With Ulceration", Journal of Vascular Surgery, 1996, 24:711-718.

Pais, S. O. et al., "Percutaneous Insertion of the Greenfield Inferior Vena Cava Filter: Experience With Ninety-Six Patients", Journal of Vascular Surgery, Oct. 1988, vol. 8, No. 4.

Papers of the Western Surgical Association, "Directed Parathyroidectomy—Feasibility and Performance in 100 Consecutive Patients With Primary Hyperparathyroidism", Archives of Surgery, Jun. 2003, vol. 138, p. 637.

Participants in the Vena Caval Fitter Consensus Conference, "Recommended Reporting Standards for Vena Caval Filter Placement and Patient Follow-Up", Journal of Vascular Surgery, 1999, 30:573-579.

Partsch, H. et al., "Frequency of Pulmonary Embolism in Patients Who Have Iliofemoral Deep Vein Thrombosis and Are Treated With Once- or Twice-Daily Low-Molecular Weight Heparin", Journal of Vascular Surgery, 1996, 24:774-782.

Passman, M. A. et al., "Pulmonary Embolism is Associated With the Combination of Isolated Calf Vein Thrombosis and Respiratory Symptoms", Journal of Vascular Surgery, 1997, 25:39-45.

Patton, J. H. Jr., et al., "Prophylactic Greenfield Filters: Acute Complications and Long-Term Follow-Up", The Journal of Trauma: Injury, Infection, and Critical Care, 1996, vol. 41, No. 2, pp. 231-237.

Peck, K. E. et al., "Postlaparoscopic Traumatic Inferior Vena Caval Thrombosis", Heart & Lung, Jul./Aug. 1998, vol. 27, No. 4, pp. 279-281.

Peterson, D. A. et al., "Computed Tomographic Venography is Specific But Not Sensitive for Diagnosis of Acute Lower-Extremity Deep Venous Thrombosis in Patients With Suspected Pulmona Embolus", Journal of Vascular Surgery, 2001, 34:798-804.

Padnos, Y. D. et al., "Complications After Laparoscopic Gastric Bypass", Archives of Surgery, Sep. 2003, 138:957-961.

Porter, J. M. et al., "Reporting Standards in Venous Disease: An Update", Journal of Vascular Surgery, 1995, 21:635-645.

Prince, M. R. et al., "The Diameter of the Inferior Vena Cava and Its Implications for the Use of Vena Caval Filters", Radiology, 1983, 149:687-689.

Proctor, M. C. et al., "Assessment of Apparent Vena Caval Penetration by the Greenfield Filter", Journal of Endovascualr Surgery, 1998, 5:251-258.

Proctor, M. C., "Indications for Filter Placement", Seminars in Vascular Surgery, Sep. 2000, vol. 13, No. 3, pp. 194-198.

Qanadli, S. D. et al., "Pulmonary Embolism Detection: Prospective Evaluation of Dual-Section Helical CT Versus Selective Pulmonary Arteriography in 157 Patients", Radiology, 2000, 217:447-455.

Quirke, T. E. et al., "Inferior Vena Caval Filter Use in U.S. Trauma Centers" A Practitioner Survey, The Journal of Trauma: Injury, Infection, and Critical Care, 1997, vol. 43, No. 2, pp. 333-337.

Rabkin, D. J. et al., "Nitinol Properties Affecting Uses in Interventional Radiology", Journal of Vascular and Interventional Radiology, 2000, 11:343-350.

Radke, P. W. et al., "Thrombosis in Behcet's Disease: Report of a Case Followed by a Systematic Review Using the Methodology of Evidence-Based Medicine", Journal of Thrombosis and Thrombolysis, Apr. 2001, 11(2):137-141.

(56) References Cited

OTHER PUBLICATIONS

Raju, N. L. et al., "Case 37: Juxtacaval Fat Collection-Mimic of Lipoma in the Subdiaphragmatic Inferior Vena Cava", Radiology, 2001, 220:471-474.
Rascona, D. A. et al., "Pulmonary Embolism-Treatment vs Nontreatment", Chest, Jun. 1999, vol. 115, No, 6, p. 1755.
Razavi, M. K. et al., "Chronically Occluded Inferior Venae Cavae: Endovascular Treatment", Radiology, 2000, 214:133-138.
Reddy, K. et al., "Insertion of an Inferior Venocaval Filter in a Pregnant Woman at Risk for Pulmonary Embolism—A Challenging Management", Departments of Obstetrics and Gynaecology and Radiology, Wexham Park Hospital, Slough, UK, 2003, p. 198.
Reekers, J. A. et al., "Evaluation of the Retrievability of the OptEase IVC Filter in an Animal Model", Journal of Vascular and Interventional Radiology, 2004, 15:261-267.
Ricotta, J. J., "Regarding" Recurrent Thromboembolism in Patients With Vena Caval Filters, Journal of Vascular Surgery, 2001, vol. 33, p. 657.
Riedel, M., "Acute Pulmonary Embolism 2: Treatment", Heart, Mar. 2001. 85(3):351-360.
Robrer, M. J. et al., "Extended Indications for Placement of an Inferior Vena Cava Filter", Journal of Vascular Surgery, Jul. 1990, vol. 12, No. 1.
Rodrigues, H. L. et al., "Update of the Management of Venous Thromboembolism [16]", Rev Port Cardiol, 2002, 21(2):183-199.
Rodriguez, J. L. et al., "Early Placement of Prophylactic Vena Caval Filters in Injured Patients at High Risk for Pulmonary Embolism", The Journal of Trauma, Injury, Infection, and Critical Care, 1996, vol. 40, No. 5, pp. 797-804.
AbuRahma, A.F. et al., "Management of Deep Vein Thrombosis of the Lower Extremity in Pregnancy: A Challenging Dilemma", The American Surgeon, Feb. 1999, vol. 65, No. 2, pp. 164-167A.
AbuRahma, F. et al., "Etiology of Peripheral Arterial Thromboembolism in Young Patients", The American Journal of Surgery, vol. 176, Aug. 1998, pp. 156-161.
Ahearn, G.S. et al., "Massive Pulmonary Embolism During Pregnancy Successfully Treated With Recombinant Tissue Plasminogen Activator", Archives of Interal Medicine, Jun. 10, 2002, 162(11):1221-1227.
American Gastroenterological Association Clinical Practice Committee, Americal Gastroenterological Associattion, Sep. 2002 123:883-932.
Anderson, J.T. et al., "Bedside Noninvasive Detection of Acute Pulmonary Embolism in Critically Ill Surgical Patients", Archives of Surgery, Aug. 1999, 134(8):869-875.
Anthone, G.J. et al., The Duodenal Switch Operation for the Treatment of Morbid Obesity, Annals of Surgery, Oct. 2003, 238(4):618-628.
Arcelus, J.I. et al, "The Management and Outcome of Acute Venous Thromboembolism: A Prospective Registry Including 4011 Patients", Journal of Vascular Surgery, 2003, 38:916-922.
Authors' Abstract, "Abstracts of Current Literature", Journal of Vascular and Interventional Radiology, Oct. 2003, vol. 14, No. 10, pp. 1351-1357.
Authors' Abstracts, "Abstract of Current Literature", Journal of Vascular and Interventional Radiology, Apr. 2004, pp. 408-415.
Bass, B.L., "What's New in General Surgery: Gastrointestinal Conditions", The Journal of American College Surgeons, Dec. 2002, vol. 195, No. 6, pp. 835-854.
Bendick, P.J. et al., Serial Duplex Ultrasound Examination for Deep Vein Thrombosis in Patients With Suspected Pulmonary Embolism, Journal of Fascular Surgery, Nov. 1996, vol. 24, No. 5, pp. 732-737.
Bessoud, B. et al., Experience at a Single Institution With Endovascular Treatment of Mechanical Complications Caused by Implanted Central Venous Access Devices in Pediatric and Adult Patients, American Journal of Roentgenology, Feb. 2003, 180:527-532.
Bevoni, L., "Management of Adult Obesity", Clinician Reviews, May 2003, 13(5):56-62.
Biertho, L. et al., "Laparoscopic Gastric Bypass Versus Laparoscopic Adjustable Gastric Banding: A Comparative Study of 1,200 Cases", Journal of the American Colloge of Surgeons, Oct. 2003, vol. 197, No. 4, pp. 536-545.
Blachar A. et al., "Gastrointestinal Complications of Laparoscopic Roux-en-Y Gastric Bypass Surgery in Patients Who Are Morbidly Obese: Findings on Radiography and CT", American Journal of Roentgenology, Dec. 2002, 179:1437-1442.
Blachar, A. et al., "Gastrointestinal Complications of Laparoscopic Roux-en-Y Gastric Bypass Surgery: Clinical and Imaging Findings", Radiology, 2002, 223:625-632.
Blaszyk, H. et al., "Factor V Leiden and Morbid Obesity in Fatal Postoperative Pulmonary Embolism", Archives of Surgery, Dec. 2000, 135(12):1410-1413.
Bovyn, G. et al., "The Tempofilter®: A Multicenter Study of a New Temporary Caval Filter Implantable for up to Six Weeks", Annals of Vascular Surgery, 1997, 11:520-528.
Bridges, G.G. et al., "Expedited Discharge in Trauma Patients Requiring Anticoagulation for Deep Venous Thrombosis Prophylaxis: The LEAP Program" The Journal of Trauma: Injury, Infection and Critical Care, Feb. 2003, vol. 54, No. 2, pp. 232-235.
Brolin, R.E., "Laparoscopic Verses Open Gastric Bypass to Treat Morbid Obesity", Annals of Surgery, Apr. 2004, vol. 239 No. 4, 438-440.
Capella, J.F. et al., An Assessment of Vertical Banded Gastroplasty-Roux-en-Y Gastric Bypass for the Treatment of Morbid Obesity.
Carter, Y. et al., "Deep Venous Thrombosis and ABO Blood Group Are Unrelated in Trauma Patients", The Journal of Trauma: Injury, Infection, and Critical Care, 2002, 52:112-116.
Castaneda, F. et al., "Catheter-Directed Thrombolysis in Deep Venous Thrombosis With Use of Reteplase: Immediate Results and Complications From a Pilot Study", Journal of Vascular and Interventional Radiology, 2002, 13:577-580.
Ceelen, W. et al., "Surgical Treatment of Severe Obesity With a Low-Pressure Adjustable Gastric Band, Experimental Data and Clinical Results in 625 Patients", Annals of Surgery, 2003, 237(1):10-16.
Chanduszko, A., "Determination of Nitinol Transition Temperatures Using a Dynamical Mechanical Analyzer", The International Conference on Shape Memory and Superelastic Technology, 2000 Conference Proceedings, 2001, pp. 375-381.
Chengelis, D.L. et al., "Progression of Superficial Venous Thrombosis to Deep Vein Thrombosis", Journal of Vascular Surgery, 1996, 24:745-749.
Choban, P.S. et al., "The Impact of Obesity on Surgical Outcomes: A Review," Journal of The American College of Surgeons, Dec. 1997, vol. 185, pp. 593-603.
Chung, J.W. et al., "Acute Iliofemoral Deep Vein Thrombosis: Evaluation of Underlying Anatomic Abnormalities by Spiral CT Venography", Journal of Vascular and Interventional Radiology, 2004, 15:249-256.
Clarke, C.S. et al., "Puerperal Ovarian Vein Thrombosis With Extension Into the Inferior Vena Cava", The American Surgeon, Feb. 1999, vol. 65, No. 2, pp. 147-150.
Cooper, S.G. et al. "Distal Retraction and Inversion of the Simon Nitinol Filter During Surgical Venous Procedures: Report of Two Cases", Journal of Vascular and Interventional Radiology, 1997, 8:433-435.
Cottam, D.R. et al., "Laparoscopic Era of Operations for Morbid Obesity", Archives of Surgery, Apr. 2003, 138(4):367-375.
Gregg, A. et al., "A New Percutaneous Vena Cava Filter", American Journal of Roentgenology, Sep. 1983, 141:601-604.
Dabbagh, A. et al., "Late Complication of a Greenfield Filter Associating Caudal Migration and Perforation of the Abdominal Aorta by a Ruptured Strut", Journal of Vascular Surgery, Aug. 1995, vol. 22, No. 2, pp. 182-187.
Dake, M.D. et al., "Thrombolytic Therapy in Venous Occlusive Disease", Journal of Vascular and Interventional Radiology, 1995, 6:73S-77S.
Dalman, R. et al., "Cerebrovascular Accident After Greenfield Filter Placement for Paradoxical Embolism", Journal of Vascular Surgery, Mar. 1989, vol. 9, No. 3, pp. 452-454.

(56) References Cited

OTHER PUBLICATIONS

Davidson, B.L., "DVT Treatment in 2000: State of the Art", Orthopedics, Jun. 2000, 23(6):pp. S651-S654.
De Gregorio, M.A. et al., "Animal Experience in the Gunther Tulip Retrievable Inferior Vena Cava Filter", Cardiovascular and Interventional Radiology, Nov. 2001, 24:413-417.
De Gregorio, M.A. et al., "Mechanical and Enzymatic Thrombolysis for Massive Pulmonary Embolism", Journal of Vascular and Interventional Radiology, 2002, 13:163-169.
Debing, E. et al., "Popliteal Venous Aneurysm With Pulmonary Embolism", Journal of Cardiovascular Surgery, Oct. 1998, vol. 39, No. 5, pp. 569-572.
Decousus, H. et al., "A Clinical Trial of Vena Caval Filters in the Prevention of Pulmonary Embolism in Patients With Proximal Deep-Vein Thrombosis", The New England Journal of Medicine, Feb. 12, 1998, vol. 338, No. 7, pp. 409-415.
DeMaria, E.J. et al., "Results of 281 Consecutive Total Laparoscopic Roux-en-Y Gastric Bypasses to Treat Morbid Obesity", Annals of Surgery, 2002, vol. 235, No. 5 pp. 640-647.
Dennis, J.W. et al., "Efficacy of Deep Venous Thrombosis Prophylaxis in Trauma Patients and Identification of High-Risk Groups", The Journal of Trauma, 1993, vol. 35, No. 1, pp. 132-137.
Denny, D.F. Jr., "Errant Percutaneous Greenfield Filter Placement Into the Retroperitoneum" Journal of Vascular Surgery Jun. 1991, vol. 13, No. 6.
Dewald, C.L. et al., Vena Cavography With $CO_2$ Versus With Iodinated Contrast Material for Inferior Vena Cava Filter Placement: A Prospective Evaluation, Radiology, 2000, 215:752-757.
Dibie, A. et al., "In Vivo Evaluation of a Retrievable Vena Cava Filter-The Dibie-Musset Filter: Experimental Results", Cardiovascular and Interventional Radiology, 1998, 21:151-157.
Duperier, T. et al., "Acute Complications Associated With Greenfield Filter Insertion i High-Risk Trauma Patients", The Journal of Trauma: Injury, Infection, and Critical Care, Mar. 2003, vol. 54, No. 3, pp. 545-549.
Edlow, J.A., "Emergency Department Management of Pulmonary Embolism", Emergency Medicine Clinics of North America, Nov. 2001, vol. 19, No. 4, pp. 995-1011.
Egermayer, P., "Follow-Up for Death or Recurrence Is Not a Reliable Way of Assessing the Accuracy of Diagnostic Tests for Thromboembolic Disease", Chest 1997, 111:1410-1413.
Ekim, N. et al., "Pulmonary Thromboembolism With Massive Vaginal Bleeding Due to Thrombolytic Therapy", Respirology, 2003, 8:246-248.
Engmann, E. et al., "Clinical Experience With the Antecubital Simon Nitinol IVC Filter", Journal of Vascular and Interventional Radiology, 1998, 9:774-778.
Fava, M. et al., "Massive Pulmonary Embolism: Percutaneous Mechanical Thrombectomy During Cardiopulmonary Resuscitation", Journal of Vascular and Intervention Radiology, 2006, 16:119-123.
Fava, M. et al., "Massive Pulmonary Embolism: Treatment With the Hydrolyser Thrombectomy Catheter", Journal of Vascular and Intervention Radiology, 2000, 11:1159-1164.
Feezor, R.J. et al., "Duodenal Perforation With an Inferior Vena Cava Filter: An Unusual Cause of Abdominal Pain", Journal of Vascular Surgery, 2002, pp. 1-3.
Fernandez, A.Z. Jr. et al., "Multivariate Analysis of Risk Factors for Death Following Gastric Bypass for Treatment of Morbid Obesity", Annals of Surgery, May 2004, vol. 239, No. 5, pp. 698-703.
Ferrel, H., "Regarding "Lessons Learned From a 6-Year Clinical Experience With Superior Vena Cava Greenfield Filters"", Journal of Vascular Surgery, Apr. 2001. vol. 33, No. 4.
Ferris, E.J. et al., "Percutaneous Inferior Vena Caval Filters: Follow-Up of Seven Designs in 320 Patients", Radiology 1993, 188:851-856.
Fink, S. et al., "Pulmonary Embolism and Malpractice Claims", Southern Medical Journal, Dec. 1998, vol. 91, No. 12, pp. 1149-1152.

Foley, M. et al., "Pulmonary Embolism After Hip or Knee Replacement: Postoperative Changes on Pulmonary Scintigrams in Asymptomatic Patients", Radiology, 1989, 172:481-485.
Fraser, J.D. et al., "Deep Venous Thrombosis: Recent Advances and Optimal Investigation With US", Radiology, 1999, 211:9-24.
Frezza, E.E. et al., "Entrapment of a Swan Ganz Catheter in an IVC Filter Requiring Caval Exploration", Journal of Cardiovascular Surgery, 1999, 40:905-908.
Friedell, M.L. et al., "Case Report: Migration of a Greenfield Filter to the Pulmonary Artery: Case Report", Journal of Vascular Surgery, Jun. 1986, vol. 3, No. 6, pp. 929-931.
Friedland, M. et al., "Vena Cava Duplex Imaging Before Caval Interruption", Journal of Vascular Surgery, Oct. 1995, vol. 24, No. 4, pp. 608-613.
Gamblin, T.C. et al., "A Prospective Evaluation of a Bedside Technique for Placement of Inferior Vena Cava Filters: Accuracy and Limitations of Intravascular Ultrasound", The American Surgeon, May 2003, vol. 69, pp. 382-386.
Garcia, N.D., "Is Bilateral Ultrasound Scanning of the Legs Necessary for Patients With Unilateral Symptoms of Deep Vein Thrombosis", Journal of Vascular Surgery, 2001, 34:792-797.
Gayer, G. et al., "Congenital Anomalies of the Inferior Vena Cava Revealed on CT in Patients With Deep Vein Thrombosis", American Journal of Roentgenology, Mar. 2003, vol. 180, 729-732.
Geerts, W.H., "A Prospective Study of Venous Thromboembolism After Major Trauma", Dec. 15, 1994, vol. 331, No. 24, pp. 1601-1606.
Gelfand, E.V. et al., "Venous Thromboembolism Guidebook, Fourth Edition", Critical Pathways in Cardiology, Dec. 2003, vol. 2, No. 4, pp. 247-265.
Ginsberg, M.S. et al., "Clinical Usefulness of Imaging Performed After CT Angiography That Was Negative for Pulmonary Embolus in a High-Risk Oncologic Population", American Journal of Roentgenology, Nov. 2002, 179:1205-1208.
Girard, P. et al., "Medical Literature and Vena Cava Filters", Chest, 2002, 122:963-967.
Goldberg, M.E., "Entrapment of en Exchange Wire by an Inferior Vena Caval Filter: A Technique for Removal", Anesth Analg., Apr. 2003, 96:4, 1235-1236.
Greenfield, L.J. et al., "Filter Complications and Their Management", Seminars in Vascular Surgery, vol. 13, No. 3, Sep. 2000, pp. 213-216.
Hak, D.J., "Prevention of Venous Thromboembolism in Trauma and Long Bone Fractures", Current Opinion in Pulmonary Medicine, 2001, 7:338-343.
Hammond, F.M. et al., "Venous Thromboembolism in the Patient With Acute Traumatic Brain Injury: Screening, Diagnosis, Prophylaxis, and Treatment Issues", Journal of Head Trauma Rehabilitation, Feb. 1998, vol. 13, No. 1, pp. 36-48.
Hardhammar, P.A. et al., "Reduction in Thrombotic Events With Heparin-Coated Palmaz-Schatz Stents in Normal Porcine Coronary Arteries", Circulation, Feb. 1, 1996, vol. 93, No, 3, pp. 423-430.
Harris, E.J. Jr. et al., "Phlegmasia Complicating Prophylactic Percutaneous Inferior Vena Caval Interruption: A Word of Caution", Journal of Vascular Surgery, 1995, vol. 22, No. 5, pp. 606-611.
Hawkins, S.P. et al., "The Simon Nitinol Inferior Vane Cava Filter: Preliminary Experience in the UK", Clinical Radiology, 1992, 46:378-380.
Headrick, J.R. et al., "The Role of Ultrasonography and Inferior Vena Cava Filter Placement in High-Risk Trauma Patients", American Surgeon, Jan. 1997, vol. 63, Issue 1.
Helfet, D., Magnetic Resonance Venography to Evaluate Deep Venous Thrombosis in Patients With Pelvic and Acetabular Trauma, The Journal of Trauma: Injury, Infection, and Critical Care, Jul. 2001, p. 178.
Heng, J.T. et al., "Occlusion of Persistent Left Superior Vena Cava to Unroofed Coronary Sinus Using Vena Cava Filter and Coils", Hears, Jun. 1997, vol. 77, No. 6, pp. 579-580.
Henkle, G. et al., "Patterns of Referral for Inferior Vena Caval Filtration: Delays and Their Impact", American Journal of Roentgenology, Oct. 2004, 183:1021-1024.

(56) References Cited

OTHER PUBLICATIONS

Hicks, M.E. et al., "Prospective Anatomic Study of the Inferior Vena Cava and Renal Veins: Comparison of Selective Renal Venography With Cavography and Relevance in Filter Placement", Journal of Vascular and Interventional Radiology, 1995, 6:721-729.
Higa, K.D. et al., "Laparoscopic Roux-en-Y Gastric Bypass for Morbid Obesity", Archives of Surgery, Sep. 2000, vol. 135, No. 9, pp. 1029-1034.
Johnson, M.S., "Current Strategies for the Diagnosis of Pulmonary Embolus", Journal of Vascular and Interventional Radiology, 2002, 13:13-23.
Kaplan, S. et al., "Surgical Management of Renal Cell Carcinoma With Inferior Vena Cava Tumor Thrombus", The American Journal of Surgery, 2002, 183:292-299.
Karmy-Jones, R. et al., "Surgical Management of Cardiac Arrest Caused by Massive Pulmonary Embolism in Trauma Patients", The Journal of Trauma: Injury, Infection, and Critical Care, 2000, vol. 48, No. 3, pp. 519-520.
Kazmers, A. et al., "Duplex Examination of the Inferior Vena Cava", The American Surgeon, Oct. 2000, vol. 66, pp. 986-989.
Kazmers, A. et al., "Intraoperative Insertion of Greenfield Filters: Lessons Learned in a Personal Series of 152 Cases", The American Surgeon, Oct. 2002, vol. 68, pp. 877-882.
Kazmers, A. et al., "Pulmona Embolism in Veterans Affairs Medical Centers: Is Vena Cava Interruption Underutilized?", The American Surgeon, Dec. 1999, vol. 65, No. 12, pp. 1171-1175.
Kearon, C. et al., "Management of Anticoagulation Before and After Elective Surgery", The New England Journal of Medicine, May 22, 1997, vol. 336, No. 21, pp. 1506-1511.
Kelly, J. et al., "Anticoagulation or Inferior Vena Cava Filter Placemente for Patients With Primary Intracerebral Hemorrhage Developing Venous Thromboembolism?" Stroke, 2003, 34:2999-3005.
Marret, H. et al., "Re: Metastatic Involvement of a Retrieved Inferior Vena Cava Filler", Journal of Vascular and Interventional Radiology, Jul. 2004, vol. 15, No. 7, pp. 775-776.
Matteson, B. et al., "Role of Venous Duplex Scanning in Patients With Suspected Pulmonary Embolism", The Journal of Vascular Surgery, 1996, 24:768-773.
Mattos, M.A. et al., "Prevalence and Distribution of Calf Vein Thrombosis in Patients With Symptomatic Deep Venous Thrombosis: A Color-Flow Duplex Study", Journal of Vascular Surgery, 1996, 24:738-744.
Maxwell, R.A. et al., "Routine Prophylactic Vena Cava Filtration is Not Indicated After Acute Spinal Cord Injury", The Journal of Trauma: Injury, Infection, and Critical Care, 2002, 52:902-906.
McMurtry, A.L. et al., "Increased Use of Prophylactic Vena Cava Filters in Trauma Patients Failed to Decrease Overall Incidence of Pulmonary Embolism", Journal of the American College of Surgeons, 1999, 189:314-320.
Meissner, M.H. et al., Venous Thromoernbolism in Trauma: A Local Manifestation of Systemic Hypercoagulability?, The Journal of Trauma: Injury, Infection, and Critical Care, Feb. 2003, vol. 54, No. 2, pp. 224-231.
Participants in the Vena Caval Filter Consensus Conference, "Recommended Reporting Standards for Vena Caval Filter Placement and Patient Follow-Up", Journal of Vascular and Interventional Radiology, 2003, 14:S427-S432.
Pelage, J. et al., "Re: Leiomyoma Recurrence After Uterine Artery Embolization", Journal of Vascular and Interventional Radiology, Jul. 2004, vol. 15, No. 7, pp. 773-776.
Quality Improvement Guidelines for Percutaneous Inferior Vena Cava Filter Placement for the Prevention of Pulmonary Embolism (European Standards adopted and Modified by CIRSE in Cooperation With SCVIR Standards of Practice Committee), http:www.cirse.org/vena_cava_filter_crise.htm, retrieved May 17, 2002, 11 pages.
RD Heparin Arthroplasty Group, "RD Heparin Compared With Warfarin for Prevention of Venous Thromboembolic Disease Following Total Hip or Knee Arthroplasty", The Journal of Bone and Joint Surgery, Incorporation, Aug. 1994, vol. 76-A, No. 8, pp. 1174-1185.

AbuRahma, A.F et al., "Endovascular Caval Interruption in Pregnant Patients With Deep Vein Thrombosis of the Lower Extremity", Journal of Vascular Surgery, 2001, 33:375-378.
Allen, T.L. et al., "Retrievable Vena Cava Filters in Trauma Patients for High-Risk Prophylaxis and Prevention of Pulmonary Embolism", The American Journal of Surgery, 2005, 189:656-661.
Arcasoy, S.M. et al., "Thrombolytic Therapy of Pulmonary Embolism", Chest, 1999, 115:1695-1707.
Arnold, D.M. et al., "Missed Opportunities for Prevention of Venous Thromboembolism", Chest, 2001, 120:1964-1971.
Brasel, K.J. et al., "Cost-Effective Prevention of Pulmonary Embolus in High-Risk Trauma Patients", The Journal of Trauma: Injury, Infection, and Critical Care, Mar. 1997, vol. 42, No. 3, pp. 456-462.
Buerger, P.M. et al., "Risk of Pulmonary Emboli in Patients With Pelvic Fractures", The American Surgeon, Aug. 1993, vol. 59, pp. 505-508.
Darcy, M.D. et al., "Short-Term Prophylaxis of Pulmonary Embolism by Using a Retrievable Vena Cava Filter", American Journal of Roentgenology, 1986, 147:836-838.
David, W. et al., "Pulmonary Embolus After Vena Cava Filter Placement", The American Surgeon, Apr. 1999, vol. 65, pp. 341-346.
Ferraro, F. et al., "Thromboembolism in Pregnancy: A New Temporary Caval Filter", Miverva Anestesiologica, 2001, vol. 67, No. 5, pp. 381-385.
Georgopoulos, S.E. et al., "Paradoxical Embolism", Journal of Cardiovascular Surgery, 2001, 42:675-677.
Goldhaber, S.Z. et al., "Acute Pulmonary Embolism: Part II Risk Stratification, Treatment, and Prevention", Circulation, 2003, 108:2834-2838.
Goldhaber, S.Z., "A Free-Floating Approach to Filters", Archives of Internal Medicine, Feb. 10, 1997, vol. 157, No. 3, pp. 264-265.
Goldhaber, S.Z., "Venous Thromboembolism in the Intensive Care Unit: The Last Frontier for Pro . . . ", Chest, Jan. 1998, 113(1):5-7.
Goldman, H.B. et al., "Ureteral Injury Secondary to an Inferior Vena Caval Filter", The Journal of Urology, Nov. 1996, vol. 156, No. 6, p. 1763.
Golueke, P.J. et al., "Interruption of the Vena Cava by Means of the Greenfield Filter: Expanding the Indications", Surgery, Jan. 1988, vol. 103, No. 1, pp. 111-117.
Gonze, M.D. et al., "Orally Administered Heparin for Preventing Deep Venous Thrombosis", American Journal of Surgery, Aug. 1998, vol. 176, pp. 176-178.
Goodman, L.R. et al., "Subsequent Pulmonary Embolism: Risk After a Negative Helical CT Pulmonary Angiogram-Prospective Comparison With Scintigraphy", Radiology, 2000, 215:535-542.
Gottlieb, R.H., "Randomized Prospective Study Comparing Routine Versus Selective Use of Sonography of the Complete Calf in Patients With Suspected Deep Venous Thrombosis", American Journal of Roentgenology, Jan. 2003, 180:241-245.
Grandas, O.H. et al., "Deep Venous Thrombosis in the Pediatric Trauma Population: An Unusual Event: Report of Three Cases", The American Surgeon, Mar. 2000, vol. 66, pp. 273-276.
Grassi, C.L. et al., "Quality Improvement Guidelines for Percutaneous Permanent Inferior Vena Cava Filter Placement for the Prevention of Pulmonary Embolism", Journal of Vascular and Interventional Radiology, Sep. 2003, 14:S271-S275.
Grassi, C.L. et al., "Vena Caval Occlusion After Simon Nitinol Filter Placement: Identification With MR Imaging in Patients With Malignancy", Journal of Vascular and Interventional Radiology, 1992, 3(3):535-539.
Greene, F.L. et al., Letters to the Editor, The Journal of Trauma: Injury, Infection, and Critical Care, May 2005, vol. 5 8, No. 5, pp. 1091-1092.
Greenfield, L.J. et al., "Free-Floating Thrombus and Pulmonary Embolism/Reply", Archives of Internal Medicine, Dec. 8-Dec. 22, 1997, pp. 2661-2662.
Greenfield, L.J. et al., "Limb Asymmetry in Titanium Greenfield Filters: Clinically Significant?", Journal of Vascular Surgery, 1997, 26:770-775.
Greenfield, L.J. et al., "Prophylactic Vena Caval Fitters in Trauma: The Rest of the Story", Journal of Vascular Surgery, 2000, 32:490-497.

(56) References Cited

OTHER PUBLICATIONS

Greenfield, L.J. et al., "Recommended Reporting Standards for Vena Caval Filter Placement and Patient Follow-Up", Journal of Vascular and Interventional Radiology, 1999, 10:1013-1019.
Greenfield, L.J. et al., "Results of a Multicenter Study of the Modified Hood-Titanium Greenfield Filter", Journal of Vascular Surgery, 1991, 14:253-257.
Greenfield, L.J. et al., "The Percutaneous Greenfield Filter: Outcomes and Practice Patterns", Journal of Vascular Surgery, 2000, 32:888-893.
Greenfield, L.J. et al., "Twenty-Year Clinical Experience With the Greenfield Filter", Cardiovascular Surgery, Apr. 1995, vol. 3, No. 2, pp. 199-205.
Greenfield, L.J., "Cost vs Value in Vena Caval Filters", Chest, Jul. 1998, vol. 114, No. 1, pp. 9-10.
Greenfield. L.J., "Current Indications for and Results of Greenfield Filter Placement", Journal Vascular Surgery, May 1984, vol. 1, No. 3, pp. 502-504.
Greenfield, L.J., "Does Cervical Spinal Cord Injury Induce Higher Incidence of Complications After Prophylactic Greenfield Filter Usage?", Journal of Vascular and Interventional Radiology, Jul.-Aug. 1997, pp. 719-720.
Greenfield, L.J., "Recurrent Thromboembolism in Patients With Vena Cava Filters", Journal of Vascular Surgery, 2001, 33:510-514.
Greenfield, L.J., "Results of a Multi-Center Study of the Modified Hook-Titanium Greenfield Filter", Journal of Vascular Surgery, Sep. 1991.
Greenfield, L.J., "Staging of Fixation and Retrievability of Greenfield Filter", Journal of Vascular Surgery, Nov. 1994, vol. 20, No. 5, pp. 744-750.
Hagspiel, K.D. et al., "Inferior Vena Cava Filters: An Update", Applied Radiology, Nov. 1998, pp. 20-34.
Hagspiel, K.L. et al., "Difficult Retrieval of a Recovery IVC Filter", Journal of Vascular and Interventional Radiology (Letters to the Editor), Jun. 2004, vol. 15, No. 6, pp. 645-650.
Hainaux, B. et al., "Intragastric Band Erosion After Laparoscopic Adjustable Gastric Banding for Morbid Obesity: Imaging Characteristics of an Underreported Complication", American Journal of Roentgenology, Jan. 2005, 184:109-112.
Harold, K.L. et al., "Laparoscopic Approach to Open Gastric Bypass", The American Journal of Surgery, 2002, 184:61-62.
Harries, S.R., "Long-Term Follow-Up of the Antheor Inferior Vena Cava Filter", Clinical Radiology, 1998, 53:350-352.
Hastings, G.S. et al., "Repositioning the 12-F Over-the-Wire Greenfield Filter", Journal of Vascular and Interventional Radiology, 2000, 11:1207-1210.
Hill, S.L. et al., "Deep Venous Thrombosis in the Trauma Patient", The American Surgeon, Jun. 1994, vol. 60, pp. 405-408.
Hingorani, A. et al., "Upper Extremity Deep Venous Thrombosis and Its Impact on Morbidity and Mortality Rates in a Hospital-Based Population", Journal of Vascular Surgery, Nov. 1997, 26:853-860.
Holtzman, R.B. et al., "Comparison of Carbon Dioxide and Iodinated Contrast for Cavography Prior to Inferior Vena Cava Filter Placement", The American Journal of Surgery, 2003, 185:364-368.
Hosaka, J. et al., "Placement of a Spring Filter During Interventional Treatment of Deep Venous Thrombosis to Reduce the Risk of Pulmonary Embolism", Acta Radiologica, 1999, 40:545-551.
Hughes, G.C. et al., "The Use of a Temporary Vena Caval Interruption Device in High-Risk Trauma Patients Unable to Receive Standard Venous Thromboembolism Prophylaxis", Investigative Radiology, Feb. 1999, vol. 46, No. 2, pp. 246-249.
Hunter, D.W. et al., "Retrieving the Amplatz Retrievable Vena Cava Filter", Cardiovascular and Interventional Radiology, 1987, 10:32-36.
Jackson Sleepy, A.L. et al., "Delayed Transcaval Renal Penetration of a Greenfield Filter Presenting as Symptomatic Hydronephrosis", The Journal of Urology, Apr. 2002, vol. 167, pp. 1778-1779.

Jaeger, H.J. et al., "A Physiologic in Vitro Model of the Inferior Vena Cava With a Computer-Controlled Flow System for Testing of Inferior Vena Cava Filters", Investigative Radiology, Sep. 1997, vol. 32, No. 9, pp. 511-522.
Johnson, S.P. et al., "Single Institution Prospective Evaluation of the Over-The-Wire Greenfield Vena Caval Filter", Journal of Vascular and Interventional Radiology, 1998, 9:766-773.
Jones, A.L. et al., "Case Report: Use of an IVC Filter in the Management of IVC Thrombosis Occurring as a Complication of Acute Pancreatitis", Clinical Radiology, 1998, 53:462-464.
Joshi, A. et al., "Filter-Related, Thrombotic Occlusion of the Inferior Vena Cava Treated With a Gianturco Stent", Journal of Vascular and Interventional Radiology, 2003, 14:381-385.
Kasirajan, K. et al., "Percutaneous AngioJet Thrombectomy in the Management of Extensive Deep Venous Thrombosis", Journal of Vascular and Interventional Radiology, 2001, 12:179-185.
Katsamouris, A.A. et al., "Inferior Vena Cava Filters: In Vitro Comparison of Clot Trapping and Flow Dynamics", Radiology, 1988, 166:361-366.
Kaufman, J.A. et al., "Guide-Wire Entrapment by Inferior Vena Caval Filters: In Vitro Evaluation", Radiology, 1996, 198:71-76.
Kaufman, J.A. et al., "Operator Errors During Percutaneous Placement of Vena Cava Filters", American Journal of Roentgenology, Nov. 1995, 165:1281-1287.
Kaw, L.L., Jr. et al., "Use of Vela Cava Filters", Techniques in Orthopaedics, 2004, 19(4):327-336.
Kercher, K. et al., "Overview of Current Inferior Vena Cava Filters", The American Surgeon, Aug. 2003, vol. 69, pp. 643-648.
Kerlan, R.K., Jr. et al., "Residual Thrombus Within a Retrievable IVC Filter", Journal of Vascular and Interventional Radiology, 16:555-557.
King, J.N. et al., "Vena Cava Filters", The Western Journal of Medicine, Mar. 1992, vol. 156, No. 3, pp. 296-296.
Kinney, T.B. et al., "Does Cervical Spinal Cord Injury Induce a Higher Incidence of Complications After Prophylactic Greenfield Inferior Vena Cava Filter Usage?", Journal of Vascular and Interventional Radiology, 1996, 7:907-915.
Kinney, T.B. et al., "Fatal Paradoxic Embolism Occurring During IVC Filter Insertion in a Patient With Chronic Pulmonary Thromboembolic Disease", Journal of Vascular and Interventional Radiology, 2001, 12:770-772.
Kinney, T.B., "Translumbar High Inferior Vena Cava Access Placement in Patients With Thrombosed Inferior Vena Cava Filters", Journal of Vascular and Interventional Radiology, 2003, 14:1563-1567.
Kinney, T.B., "Update on Inferior Vena Cava Filters", Journal of Vascular and Interventional Radiology, 2003, 14:425-440.
Kozak, T.K.W. et al., "Massive Pulmonary Thromboembolism After Manipulation of an Unstable Pelvic Fracture: A Case Report and Review of the Literature", The Journal of Trauma: Injury, Infection, and Critical Care, 1995, vol. 38, pp. 366-367.
Kraimps, J. et al., "Optical Central Trapping (Opcetra) Vena Caval Filter: Results of Experimental Studies", Journal of Vascular and Interventional Radiolory, 1992, 3:697-701.
Kupferschmid, J.P. et al., "Case Report: Small-Bowel Obstruction From an Extruded Greenfield Filter Strut: an Unusual Late Complication", Journal of Vascular Surgery, Jul. 1992, vol. 16, No. 1, pp. 113-115.
Kurgan, A. et al., "Case Reports: Penetration of the Wall of an Abdominal Aortic Aneurysm by a Greenfield Filter Prong: a Late Complication", Journal of Vascular Surgery, Aug. 1993, vol. 18, No. 2, pp. 303-306.
Kuszysk, B. et al., "Subcutaneously Tethered Temporary Filter: Pathologic Effects in Swine", Journal of Vascular and Interventional Radiology, Nov.-Dec. 1995, vol. 6, No. 6, pp. 895-902.
Leask, R.L. et al., "Hemodynamic Effects of Clot Entrapment in the TrapEase Inferior Vena Cava Filter", Journal of Vascular and Interventional Radiology, 2004, 15:485-490.
Leask, R.L. et al., "In Vitro Hemodynamic Evaluation of a Simon Nitinol Vena Cava Filter: Possible Explanation of IVC Occlusion", Journal of Vascular and Interventional Radiology, 2001, 12:613-618.
Lemmon, G.W. et al., "Incomplete Caval Protection Following Suprarenal Caval Filter Placement", Angiology the Journal of Vascular Diseases, Feb. 2000, vol. 51, No. 2, pp. 155-159.

(56) References Cited

OTHER PUBLICATIONS

Lin, M. et al., "Successful Retrieval of Infected Gunther Tulip IVC Filter", Journal of Vascular and Interventional Radiology, 2000, 11:1341-1343.

Lipman, J.C., "Removal of Vena Caval Filler at 224 Days", Southern Medical Journal, May 2005, vol. 98, No. 5, pp. 556-558.

Loehr, S.P. et al., "Retrieval of Entrapped Guide Wire in an IVC Filter Facilitated With Use of a Myocardial Biopsy Forceps and Snare Device", Journal of Vascular and Interventional Radiology (Letter to Editor), Sep. 2001, vol. 12, No. 9, pp. 1116-1118.

Lorch, H. et al., "Current Practice of Temporary Vena Cava Filter Insertion: A Multicenter Registry", Journal of Vascular and Interventional Radiology, 2001, 11:83-88.

Lorch, H. et al., "Temporary Vena Cava Filters and Ultrahigh Streptokinase Thrombolysis Therapy: A Clinical Study", Cardiovascular Interventional Radiology, 2000, 23:273-278.

Lund, G. et al., "A New Vena Caval Filter for Percutaneous Placement and Retrieval Experimental Study", Radiology, 1984, 152:369-372.

Lund, G. et al., "Retrievable Vena Caval Filter Percutaneously Introduced", Radiology, 1985, vol. 155, p. 831.

Machado, L.G. et al., "Medical Applications of Shape Memory Alloys", Brazilian Journal of Medical and Biological Research, 2003, 36:683-691.

Magnant, J.G. et al., "Current Use of Inferior Vena Cava Filter", Journal of Vascular Surgery, Nov. 1992, vol. 16, No. 5, pp. 701-706.

Marston, W.A. et al., "Re: Comparison of the AngioJet Rheolytic Catheter to Surgical Thrombectomy for the Treatment of Thrombosed Hemodialysis Grafts", Journal of Vascular and Interventional Radiology (Letters to the Editor), Sep. 2000, vol. 11, No. 8, pp. 1095-1099.

McCowan, T.C. et al., "Complications of the Nitinol Vena Caval Filter", Journal of Vascular and Interventional Radiology, 1992, 3:401-408.

Melinek, J. et al., "Autopsy Findings Following Gastric Bypass Surgery for Morbid Obesity", Arch Path Lab Med, 2002 126:1091-1095.

Mihara, H. et al., "Use of Temporary Vena Cava Filters After Catheter-Directed Fragmentation and Thrombolysis in Patients With Acute Pulmonary Thromboembolism", Japanese Circulartion Journal, Jun. 1998, vol. 62, pp. 462-464.

Millward, S.F et a l., "Preliminary Clinical Experience with the Gunther Temporary Inferior Vena Cava Filter", Journal of Vascular and Interventional Radiology, 1994, 5:863-868.

Millward, S.F. et al., "Gunther Tulip Filter" Preliminary Clinical Experience With Retrieval, Journal of Vascular and Interventional Radiology, 2000, 11:75-82.

Millward, S.F et al., "Gunther Tulip Retrievable Vena Cava Filter: Results From the Registry of the Canadian Interventional Radiology Association", Journal of Vascular and Interventional Radiology, 2001, 12:1053-1058.

Millward, S.F. et al., "LGM (Vena Tech), Vena Caval Filter: Clinical Experience in 64 Patients", Journal of Vascular and Interventional Radiology, Nov. 1991, 2:429-433.

Millward, S.F. et al., "LGM (Vena Tech), Vena Caval Filter: Experience at a Single Institution", Journal of Vascular and Interventional Radiology, Mar.-Apr. 1994, 5:351-356.

Millward, S.F. et al., "Reporting Standards for Inferior Venal Caval Filter Placement and Patient Follow-Up: Supplement for Temporary and Retrievable/Optional Filters", Journal of Vascular and Interventional Radiology, Apr. 2005, 16:441-443.

Millward, S.F., "Gunther Tulip Retrievable Filter" Why, When and How?, JACR, Jun. 2001, vol. 52, No. 3, pp. 188-192.

Millward, S.F., "Temporary and Retrievable Inferior Vena Cava Filters" Current Status, Journal of Vascular and Interventional Radiology, May-Jun. 1998, vol. 9, No. 3, pp. 381-387.

Mobin-Uddin, K. et al., "Evolution of a New Device for the Prevention of Pulmonary Embolism", The American Journal of Surgery, vol. 168, Oct. 1994, pp. 330-334.

Mohan, C.R. et al., "Comparative Efficacy and Complications of Vena Caval Filters", Journal of Vascular Surgery, 1995, 21:236-236.

Montessuit, M. et al., "Screening for Patent Foramen Ovale and Prevention of Paradoxical Embolus", Ann Fasg Surg, 1997, 11:168-172.

Montgomery, K.D. et al., The Detection and Management of Proximal Deep Venous Thrombosis in Patients With Acute Acetabular Fractures: A Follow-up Report:, Journal of Orthopedic Trauma, Jul. 1997, 1(5):330-336.

Munir, M.A. et al., "An in Situ Technique to Retrieve an Entrapped J-Tip Guidewire From an Inferior Vena Cava Filter", Anesth Analo, 2002, 95:308-309.

Stosslein, F. et al., "A Rare Complication With an Antheor Vena Cava Filter", Cardiovascular and Interventional Radiology, 1998, 21:165-167.

Wholey, M. et al., "Technique or Retrieval of a Guidewire Lodged in a Vena Cava Filter", Vascular and Endovascular Surgery, 2002, vol. 36, No. 5, pp. 385-387.

Adye, B. A., "Case Report: Errant Percutaneous Greenfield Filter Placement Into the Retroperitoneum", Journal of Vascular Surgery, Jul. 1990, vol. 12, No. 1.

Aklog, L. et al., "Acute Pulmonary Embolectomy", Circulation, 2002, 105:1416-1419.

Alexander, J. J. et al., "Is the Increasing Use of Prophylactic Percutaneous IVC Filters Justified?", The American Journal of Surgery, Aug. 1994, vol. 168, pp. 102-106.

Andrews, R. T. et al., "Entrapment of J-Tip Guidewires by Venatech and Stainless-Steel Greenfield Vena Cava Filters During Central Venous Catheter Placement: Percutaneous Management in Four Patients", Correspondence to R.T. Andrews, M.D., The Dotter Interventional Institute, Oregon Heal Sciences University, Portland, OR, pp. 424-427.

Arjomand, H. et al., "Right Ventricular Foreign Body: Percutaneous Transvenous Retrieval of a Greenfield Filter From the Right Ventricle", Angiology, 2003, vol. 54, No. 1, pp. 109-113.

Ascer, E. et al. "Superior Vans Caval Greenfield Filters: Indications, Techniques, and Results", Journal of Vascular Surgery, Mar. 1996, vol. 23, No. 3.

Asch, M. R., "Initial Experience in Humans With a New Retrievable Inferior Vena Cava Filter", Radiology, 2002, 225:835-844.

Ascher, E. et al., "Lessons Learned From a 6-Year Clinical Experience With Superior Vena Cava Greenfield Filters", Journal of Vascular Surgery, Nov. 2000, 32:881-887.

Ashley, D.W. et al., "Accurate Deployment of Vena Cava Filters: Comparison of Intravascular Ultrasound and Contrast Venography", The Journal of Trauma Injury, Infection, and Critical Care, Jun. 2001, vol. 50, No. 6, pp. 975-981.

Aswad, M. A. et al., "Early Duplex Scan Evaluation of Four Venal Interruption Devices", Journal of Vascular Surgery, 1996, 24:809-818.

Athanasoulis, C.A. et al., "Inferior Venal Caval Filters: Review of a 26-Year Single-Center Clinical Experience", Radiology, 2000, 216:54-66.

Avery, M. et al., "Reverse Engineering of Nitinol Vena Cava Filters", Material Science 102 Semester Project, Nov. 21, 2000.

Baker, R. J., "Treatment Considerations for Inherited Thrombophilia and Pulmonary Embolus", Archives of Surgery, Feb. 2001, 136,2:237.

Balshi, J. D. et al., "Original Articles" Complications of Caval Interruption by Greenfield Filter in Quadriplegics, Journal of Vascular Surgery, Apr. 1989, vol. 9, No. 4.

Barraco, R. D. et al., "Dislodgment of Inferior Vena Cava Filters During Central Line Placement: Case Report", The Journal of Trauma, Injury, Infection and Critical Care, 2000, vol. 48, No. 1, pp. 140-142.

Barreras, J. R. et al., "Recurrent pulrny Embolism Despite the Use of a Greenfield Filter", Clinical Nuclear, Dec. 2001, vol. 26, No. 12, pp. 1040-1041.

Barton, A. L. et al., "Caval Filter Placement for Pulmonary Embolism in a Patient With a Deep Vein Thrombosis and Primary Intracerebral Haemorrhage", Age and Ageing, Mar. 2002, 31,2:144-146.

Becker, D. M. et al., "Inferior Vena Cava Filters", Archives of Internal Medicine, Oct. 1992, vol. 152, pp. 1945-1994.

(56) References Cited

OTHER PUBLICATIONS

Benjamin, M. E. et al., Duplex Ultrasound Insertion of Inferior Vena Cava Filters in Multitrauma Patients:, American Journal of Surgery, Aug. 1999, vol. 178, pp. 92-97.
Binkert, C. A. et al., "Inferior Vena Cava Filter Removal After 317-Day Implantation", Journal of Vascular Radiology, Mar. 2005, 16:393-398.
Bjarnason, H. et al., "In Vitro Metal Fatigue Testing of Inferior Vena Cava Filters", Investigative Radiology, 1994, vol. 29, No. 9, pp. 817-821.
Blebea J. et al., "Deep Venous Thrombosis After Percutaneous Insertion of Vena Caval Filters", Journal of Vascular Surgery, Nov. 1999, 30:821:829.
Bochenek, K. M. et al., "Right Atrial Migration and Percutaneous Retrieval of a Gunther Tulip Inferior Vena Cava Filter", Journal of Vascular Interventional Radiology, Sep. 2003, 14:1207-1209.
Bochicchio, G. V. et al., "Acute Caval Perforation by an Inferior Vena Cava Filter in a Multitrauma Patient: Hemostatic Control With a New Surgical Hemostat", The Journal of Trauma Injury, Infection and Critical Care, 2001, 51:991-993.
Bracale, G. et al., "Spontaneous Rupture of the Iliac Vein", The Journal of Cardiovascular Surgery, 1999, 40:871-875.
Bravo, S. M. et al., "Percutaneous Venous Interventions", Vascular Medicine, 1998, 3:61-66.
Brountzos, E. N. et al., "A New Optional Vena Cava Filter: Retrieval at 12 Weeks in an Animal Model", Journal of Vascular and Interventional Radiology, Jun. 2003, 14:763-772.
Brown, D. R. et al., "Gadolinium, Carbon Dioxide, and Iodinated Contrast Material for Planning Inferior Vena Cava Filter Placement: a Prospective Trial", Journal of Vascular and Interventional Radiology, Aug. 2003, 14:1017-1022.
Browne, R. J. et al., "Guidewire Entrapment During Greenfield Filter Deployment", Journal of Vascular Surgery, Jan. 1998, 27:174-176.
Bruckheimer, E. et al., "In Vitro Evaluation of a Retrievable Low-Profile Nitinal Vena Cava Filter", Journal of Vascular and Interventional Radiology, Apr. 2003, 14:469-474.
Bucker, A. et al., "Real-Time MR Guidance for Inferior Vena Cava Filter Placement in an Animal Model", Journal of Vascular and Interventional Radiology, Jun. 2001, 12:753-756.
Burbridge, B. E. et al., "Incorporation of the Gunther Temporary Inferior Vena Cava Filter Into the Caval Wall", Journal of Vascular and Interventional Radiology, Mar.-Apr. 1996, 7:289-290.
Cahn, M. D. et al., "Long Term Follow-up of Greenfield Inferior Vena Cava Filter Placement in Children", Journal of Vascular Surgery, Nov. 2001, 34:820-825.
Cain Jr., J.E. et al., "The Morbidity of Heparin Therapy After Development of Pulmonary Embolus in Patients Undergoing Thoracolumbar or Lumbar Spinal Fusion", Spine, vol. 20, No. 14, 1995, 1600-1603.
Campbell, J. J. et al., "Aortic Pseudoaneurysm From Aortic Penetration With a Bird's Nest Vena Cava Filter", Journal of Vascular Surgery, Sep. 2003, 38:596-599.
Carabasi III, R. A. et al., "Complications Encountered With the Use of the Greenfield Filter", The American Journal of Surgery, Aug. 1987, Vo. 154, pp. 163-168.
Carlin, A. M. et al., "Prophylactic and Therapeutic Inferior Vena Cava Filters to Prevent Pulmonary Emboli in Trauma Patients", Archives of Surgery, May 2002, vol. 137, p. 521.
Chaturvedi, R. R. et al., "Intraoperative Apical Ventricular Septal Defect Closure Using a Modified Rashkind Double Umbrella", Heart, Oct. 1996, vol. 75, No. 4, pp. 367-369.
Cherian, J. et al., "Recurrent Pulmonary Embolism Despite Inferior Vena Cava Filter Placement in Patients With the Antiphospholipid Syndrome", Journal of Clinical Rheumatology, Feb. 2005, vol. 11, No. 1, pp. 56-58.
Cho, K. J. et al., "Evaluation of a New Percutaneous Stainless Steel Greenfield Filter", Journal of Vascular and Interventional Radiology, Mar.-Apr. 1997, 8:181-187.
Conners III, M. S et al., "Duplex Scan-Directed Placement of Inferior Vena Cava Filters: A Five-year Institutional Experience", Journal of Vascular Surgery, Feb. 2002, vol. 35, No. 2, pp. 286-291.
Couch, G. G. et al., "An in Vitro Comparison of the Hemodynamics of Two Inferior Vane Cava Filters", Journal of Vascular Surgery, Mar. 2000, 31:539-549.
Couch, G. G. et al., "In Vitro Assessment of the Hemodynamic Effects of a Partial Occlusion in a Vena Cava Filter", Journal of Vascular Surgery, Apr. 1997, vol. 25, No. 4, pp. 663-672.
Crochet, D. et al., "Evaluation of the LGM Vena-Tech Infrarenal Vena Cava Filter in an Ovine Venous Thromboembolism Model" Journal of Vascular Interventional Radiology, Jun. 2001, 12:739-745.
Crochet, D. P. et al., "Long-Term Follow-Up of Vena Tech-LGM Filter Predictors and Frequency of Caval Occlusion", Journal of Vascular Interventional Radiology, Feb. 1999, 10:137-142.
Crochet, D. P. et al., "Vena Tech-LGM Filter: Long-Term Results of a Prospective Study", Radiology, 1993, 188:857-860.
Cvoro,V. et al., "Inferior Vena Caval Filters or Anticoagulation for Patients With Haemorrhagic Stroke Complicated by Venouse Thromboembolism?", Age and Ageing, Mar. 2002, vol. 32, No. 2, Research Library, pp. 85-86.
Danetz, J. S. et al., "Selective Venography Versus Nonselective Venography Before Vena Cava Filter Placement: Evidence for More, Not Less", Journal of Vascular Surgery, Nov. 2003, Vo. 38, No. 5, pp. 928-934.
Dick, A. et al., "Declotting of Embolized Temporary Vena Cava Filter by Ultrasound and the Angiojet: Comparative Experimental in Vitro Studies", Investigative Radiology, 1998, vol. 33(2), pp. 91-97.
Gabelmann, A. et al., "Percutaneous Retrieval of Lost of Misplaced Intravascular Objects", American Journal of Radiology, Jun. 2001, 176:1509-1513.
Gelbfish, G. A. et al., "Intracardiac and Intrapulmonary Greenfield Filters: A Long-Term Follow-Up", Journal of Vascular Surgery, Nov. 1991, Vo. 14, No. 5, pp. 614-617.
Girard, T. D. et al., "Prophylactic Vena Cava Filters for Trauma Patients: A Systematic Review of the Literature", Thrombosis Research, 2003, 112:261-267.
Greenfield, L. J. et al., "Experimental Embolic Capture by Asymmetric Greenfield Filters", Journal of Vascular Surgery, Sep. 1992, vol. 16, No. 3, pp. 436-444.
Kronemyer, B., Temporary Filter Traps Pulmonary Emboly, Orthopedics Today, p. 34.
Kuszyk, B. et al., "Subcutaneously Tethered Temporary Filter: Pathologic Effects in Swine", Journal of Vascular and Interventional Radiology, Nov.-Dec. 1995, Vo. 6, No. 6, pp. 895-902.
Mobin-Uddin, K. et al., "Evolution of a New Device for the Prevention of Pulmonary Embolism", The American Journal of Surgery, Oct. 1994, vol. 168, pp. 330-334.
Patterson, R. B. et al., "Case Reports: Repositioning of Partially Dislodged Greenfield Filters From the Right Atrium by Use of a Tip Deflection Wire", Journal of Vascular Surgery, Jul. 1990, vol. 12, No. 1, pp. 70-72.
Rogers, F. B. et al., "Immediate Pulmonary Embolism After Trauma: Case Report", Journal of Trauma: Injury, Infection, and Critical Care, vol. 48, No. 1, pp. 146-148.
Salamipour, H. et al., "Percutaneous Transfemoral Retrieval of a Partially Deployed Simon-Nitinol Filter Misplaced Into the Ascending Lumbar Vein", Journal of Vascular and Interventional Radiology, 1996, 7:917-919.
Savin, M. A. et al., "Greenfield Filter Fixation in Large Vena Cavae", Journal of Vascular and Interventional Radiology, 1998, 9:75-80.
Schanzer, H. et al., "Guidewire Entrapment During Deployment of the Over-the-Guidewire Stainless Steel Greenfield Filter: A Device Design-Related Complication", Journal of Vascular Surgery, 2000, 31:607-610.
Sharafuddin, M. J. et al., "Endovascular Management of Venous Thrombotic and Occlusive Diseases of the Lower Extremities", Journal of Vascular and Interventional Radiology, Apr. 2003, 14:405-423.
Shellock, F. G. et al., "MR Procedures: Biologic Effects, Safety, and Patient Care", Radiology, 2004, 232:635-652.
"Staff Development Special, Get the Edge on Deep Vein Thrombosis", Nursing Management, Jan. 2004, pp. 21-29.

(56) References Cited

OTHER PUBLICATIONS

Taheri, S. A. et al., "Case Report: A Complication of the Greenfield Filter: Fracture and Distal Migration of Two Struts—A Case Report", Journal of Vascular Surgery, Jul. 1992, vol. 16, No. 1, pp. 96-99.
Tardy, B. et al, "Older People Included in a Venous Thrombo-Embolism Clinical Trial: A Patients' Viewpoint", Age and Ageing, 2003, 32:149-153.
Teitelbaum, G. P. et al., Low-Artifact Intravascular Devices: MR Imaging Evaluation, Radiology, Sep. 1988, 168:713-719.
Trerotola, S. O. et al., "Mechanical Thrombolysis of Venous Thrombosis in an Animal Model With Use of Temporary Caval Filtration", Journal of Vascular and Interventional Radiology, Sep. 2001, 12:1075-1085.
Uflacker, R., "Interventional Therapy for Pulmonary Embolism", Journal of Vascular Interventional Radiology, Feb. 2001, 12:147-164.
Weeks, S. M. et al., "Primary Gianturco Stent Placement for Inferior Vena Cava Abnormalities Following Liver Transplantation", Journal of Vascular and Interventional Radiology, Feb. 2000, 11:177-187.
Osamu Nakajima, et al., "Massive Deep Vein Thrombosis After Cesarean Section Treated With a Temporary Inferior Vena Cava Filter: A Case Report", J Cardiol 2000; 36(5): pp. 337-342.
J. Neuerburg et al., "New Retrievable Percutaneous Vena Cava Filter: Experimental in Vitro and in Vitro Evaluation", Cardiovasc Intervent Radiol, 1993, 16:224-229.
J.M. Neuerburg, et al., "Percutaneous Retrieval of the Tulip Vena Cava Filter: Feasibility, Short-and Long-Term Changes—An Experimental Study in Dogs", Cardiovascular and Interventional Radiology, 2001, 24:418-423.
O. A. Terhaar, et al., "Extended Interval for Retrieval of Gunther Tulip Filters", J Vasc Interv Radiol, Nov. 2004, 15:1257-1262.
J. Neuerburg, et al., "Developments in Inferior Vena Cava Filters", Seminars in Interventional Radiology, vol. II, No. 4, Dec. 1994, pp. 349-357.
A. M. Palestrant, et al., "Comparative in Vitro Evaluation of the Nitinol Inferior Vena Cava Filter", Radiology, Nov. 1982, 145:351-355.
P.A. Poletti, et al., "Long-Term Results of the Simon Nitinol Inferior Vena Cava Filter", Eur. Radiol, 1998, vol. 8, pp. 289-294.
D. Putterman, et al., "Aortic Pseudoaneurysm After Penetration by a Dion Nitinol Inferior Vena Cava Filter", J Vasc Interv Radiol, 2005, 16:535-538.
Z. Qian et al., "In Vitro and in Vivo Experimental Evaluation of a New Vena Cava Filter", Journal of Vascular and Interventional Radiology, May-Jun. 1994, pp. 513-518.
C.E. Ray Jr., et al., "Complications of Inferior Vena Cava Filters", Abdominal Imaging, 1996, 21:368-374.
S. Raghavan et al., "Migration of Inferior Vena Cava Filter Into Renal Hilum", Nephron, Jun. 2002; 91, 2; Health & Medical Complete; p. 333.
J.O.F Roehm Jr., "The Bird's Nest Filter: A New Percutaneous Transcatheter Inferior Vena Cava Filter", Journal of Vascular Surgery, Oct. 1984, vol. 1, No. 3.
J,O.F. Roehm Jr., et al., "The Bird's Nest Inferior Vena Cava Filter: Progress Report", Radiology, Sep. 1988, 168:745-749.
M. A. Savin et al., "Placement of Vena Cava Filters: Factors Affecting Technical Success and Immediate Complications", AJR, Sep. 2002, Vo. 179, pp. 597-602.
F. B. Rogers et al., "Five-Year Follow-Up of Prophylactic Vena Cava Filters in High-Risk Trauma Patients", Archives of Surgery, Apr. 1998, vol. 133, 4:Health & Medical Complete, p. 406.
J.-M. Schleich, et al., "Long-Term Follow-up of Percutaneous Vena Cava Filters: A Prospective Study in 100 Consecutive Patients", Eur J Vasc Endovasc Surg, 2001, vol. 21, pp. 450-457.
M. Shahmanesh et al., "Inferior Vena Cava Filters for HIV Infected Patients With Pulmonary Embolism and Contraindications to Anticoagulation", Sex Transm INF, 2000, 76:395-397.
H. Rousseau, et al., "The 6-F Nitinol TrapEase Inferior Vena Cava Filter: Results of a Prospective Multicenter Trial", J Vasc Interv Radiol, 2001, 12:299-304.

G. W. Stoneham et al., "Temporary Inferior Vena Cava Filters: In Vitro Comparison With Permanent IVC Filters", Journal of Vascular and Interventional Radiology, Sep.-Oct. 1995, vol. 6, pp. 731-736.
R.F. Sing, "Safety and Accuracy of Bedside Carbon Dioxide Cavography for Insertion of Inferior Vena Cava Filters in the Intensive Care Unit" American College of Surgeons, Feb. 2, 2001, vol. 192, pp. 168-171.
M. Simon et al., "Simon Nitinol Inferior Vena Cava Filter: Initial Clinical Experience", Radiology, vol. 172, No. 1, pp. 99-103, Jul. 1989.
L.D. Spence et al., "Acute Upper Extremity Deep Venous Thrombosis, Safety and Effectiveness of Superior Vena Caval Filters", Radiology, Jan. 1999, vol. 210, pp. 53-58.
R.L. Leask et al., "In Vito Hemodynamic Evaluation of a Simon Nitinol Vena Cava Filter: Possible Explanation of IVC Occlusion", J Vas Interv Radiol, May 2001, 12:613-618.
F. Stosslein et al., "A Rare Complication With an Antheor Vena Cava Filter", Cardiovascular and Interventional Radiology, , 1998, 21:165-167.
M.B. Streiff, "Vena Caval Fillers: A Comprehensive Review", Blood, Jun. 15, 2000, vol. 95, No. 12, pp. 3669-3677.
K. Tay et al, "Repeated Gunther Tulip Inferior Vena Cava Filter Repositioning to Prolong Implantation Time", J Vasc Interv Radiol, May 2002, 13:509-512.
F. C. Taylor et al., "Vena Tech Vena Cava Filter: Experience and Early Follow-up", Journal of Vascular Interventional Radiology, Nov. 1991, 2:435-440.
C. Thery et al., "Use of a New Removable Vena Cava Filter in Order to Prevent Pulmonary Embolism in Patients Submitted to Thrombolysis", European Heart Journal, 1990, vol. 11, 334-341.
M. Porcellini et al., "Intracardiac Migration of Nitinol TrapEase Vena Cava Filter and Paradoxical Embolism", European Journal of Cardio-Thoracic Surgery , vol. 22, 2002, pp. 460-461.
L. D. Vos et al., "The Gunther Temporary Inferior Vena Cava Filter for Short-Term Protection Against Pulmonary Embolism", Cardiovascular and Interventional Radiology, 1997, 20:91-97.
S. Watanabe et al., "Clinical Experience With Temporary Vena Cava Filters", Vascular Surgery, vol. 35, No. 4, 2001, pp. 285-291.
M. Zwaan et al., "Clinical Experience With Temporary Vena Caval Filters", JVIR, Jul.-Aug. 1998, vol. 9, No. 4. pp. 594-601.
A. Dardik et al., "Vena Cava Filter Ensnarement and Delayed Migration: An Unusual Series of Cases", Journal of Vascular Surgery, Nov. 1997, vol. 26, No. 5.
J. M. Pereira de Godoy et al., "In-Vitro Evaluation of a New Inferior Vena Cava Filter—The Stent-Filter", Vascular and Endovascular Surgery, Nov. 3, 2004, vol. 38, pp. 225-228.
B. D. Davison et al., "TrapEase Inferior Vena Cava Filter Placed Via the Basilic Arm Vein: A New Antecubital Access", J Vasc Interv Radiol, Jan. 2002, 13:107-109.
M. A. De Gregorio et al, "Retrievability of Uncoated Versus Paclitaxel-Coated Gunther-Tulip IVC Filters in an Animal Model", J Vasc Interv Radiol, Jul. 2004, 15:719-726.
M.A. de Gregorio, "Inferior Vena Cava Filter Update", Arch Bronconeumol, 2004, vol. 40, No. 5, pp. 193-195.
M.A. de Gregorio et al., "The Gunther Tulip Retrievable Filter: Prolonged Temporary Filtration by Repositioning Within the Inferior Vena Cava", J Vasc Interv Radiol, Oct. 2003, 14:1259-1265.
J.L. Ebaugh et al., "Bedside Vena Cava Filter Placement Guided With Intravascular Ultrasound", Journal of Vascular Surgery, Jul. 2001, 34:21-26.
L. J. Greenfield et al., "A New Intracaval Filter Permitting Continued Flow and Resolution of Emboli", Surgery, Apr. 1973, vol. 73, No. 4, pp. 599-606.
R. W. Gunther et al., "Vena Caval Filter to Prevent Pulmonary Embolism: Experimental Study", Radiology, Aug. 1985, 156:315-320.
A. C. Veribrux, "Protection Against Pulmonary Embolism: Permanent end Temporary Caval Filters", Associate Professor of Radiology and Surgery, Department of Radiology—CVDL, The Johns Hopkins Medical Institutions, Baltimore, MD.
J.S. Gosin et al., "Efficacy of Prophylactic Vena Cava Filters in High-Risk Trauma Patients", Ann Vasc Surg, 1997, 11:100-105.

(56) References Cited

OTHER PUBLICATIONS

P. Haage et al., "Prototype Percutaneous Thrombolytic Device: Preclinical Testing in Subacute Inferior Vena Caval Thrombosis in a Pig Model", Radiology, Jul. 2001, 220:135-141.
W. F. Oppat et al., "Intravascular Ultrasound-Guided Vena Cava Filter Placement" J Endovasc Surg, 1999, 6:285-287.
F.D. Hammer et al., "In Vitro Evaluation of Vena Cava Filters", Journal of Vascular and Interventional Radiology, Nov.-Dec. 1994, 5:869-876.
S.J. Savader, Inferior Vena Cava Filters, Chapter 28, pp. 367-399.
S.C. Rose et al., "Placement of Inferior Vena Caval Filters in the Intensive Care Unit", Journal of Vascular Interventional Radiology, Jan.-Feb. 1997, 8:61-64.
D. H. Epstein et al., "Experience With the Amplatz Retrievable Vena Cava Filter", Radiology, 1989, 172:105-110.
C.A. Athanasoulis et al., "Inferior Vena Caval Filters: Review of a 26-Year Single-Center Clinical Experience", Radiology, 2000, 216:54-66.
F. Fobbe et al., "Gunther Vena Caval Filter: Results of Long-Term Follow-Up", AJR, Nov. 1988, 151:1031-1034.
L.J. Greenfield et al ., "Extended Evaluation of the Titanium Greenfield Vena Caval Filter", Journal of Vascular Surgery, Nov. 1994, vol. 20, No. 3, pp. 458-465.
L. J. Greenfield et al., "Vena Caval Filter Use in Patients With Sepsis", Archives of Surgery, Nov. 2003, vol. 138, No. 11, Health & Medical Complete, p. 1245.
L.J. Greenfield et al., "Suprarental Filter Placement", Journal of Vascular Surgery, Sep. 1998, 28:432-438.
L.J. Greenfield et al., "Clinical Experience With the Kim-Ray Greenfield Vena Caval Filter", Ann Surg, Jun. 1977, vol. 185, No. 6, pp. 692-698.
C. Nutting et al., "Use of a TrapEase Device as a Temporary Caval Filter", Journal of Vascular Interventional Radiology, Aug. 2001, 12:991-993.
D. Pavcnik et al., "Retrievable IVC Square Stent Filter: Experimental Study", Cardiovascular Interventional Radiology, 1999, 22:239-245.
M. Ponchon et al., "Temporary Vena Caval Filtration Preliminary Clinical Experience With Removable Vena Caval Filters", Acta Clinica Belgica, 1999, vol. 54, pp. 223-228.
J.A. Reekers, "Re Current Practice of Temporary Vena Cava Filter Insertion: A Multicenter Registry", Journal of Vascular Interventional Radiology, Nov.-Dec. 2000, p. 1363.
J.A. Reekers et al., "Evaluation of the Retrievability of the OptEase IVC Filter in an Animal Model", Journal of Vascular Interventional Radiology, Mar. 2003, 15:261-267.
R.A. Reed, "The Use of Inferior Vena Cava Filters in Pediatric Patients for Pulmonary Embolus Prophylaxis", Cardiovascular and Interventional Radiology, 1996, 19:401-405.
J. B. Ricco et al., "Percutaneous Transvenous Caval Interruption with the LGM Filter", Ann Vasc Surg, 1988, 3:242-247.
J.D. Robinson et al., "In Vitro Evaluation of Caval Filters", Cardiovascular a nd Interventional Radiology, 1988, 11:346-351.
M.J. Wallace et al., "Inferior Vena Caval Stent Filter", AJR, Dec. 1986, 147:1247-1250.
K. Yavuz et al., "Retrievable of a Malpositioned Vena Cava Filter With Embolic Protection With Use of a Second Filter", Journal of Vascular Interventional Radiology, 2005, 16:531-534.
D. Danikas et al., "Use of a Fogarty Catheter to Open an Incompletely Expanded Vena Tech-LGM Vena Cava Filter", Angiology, Apr. 2001, vol. 52, No. 4, p. 283.

\* cited by examiner

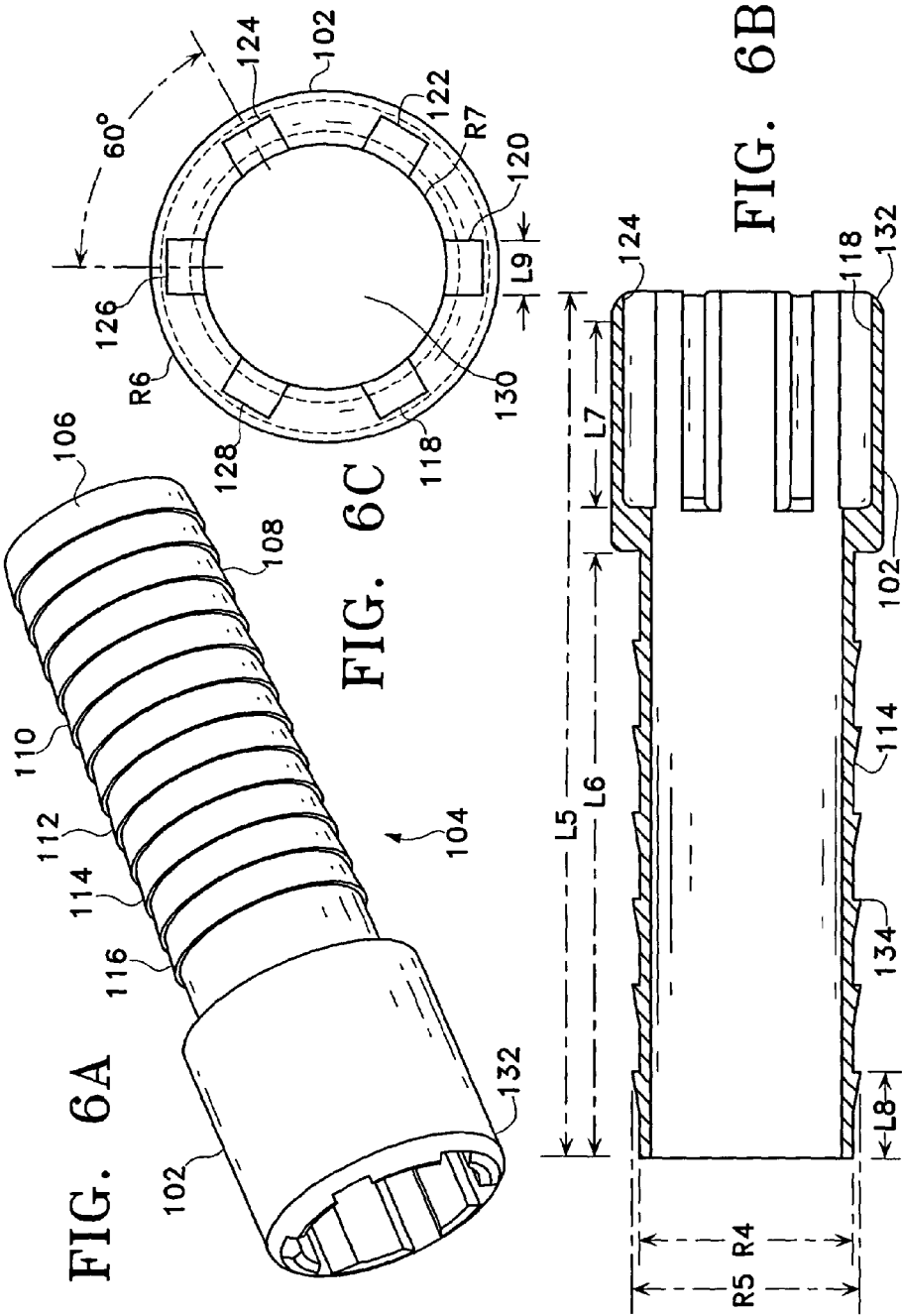

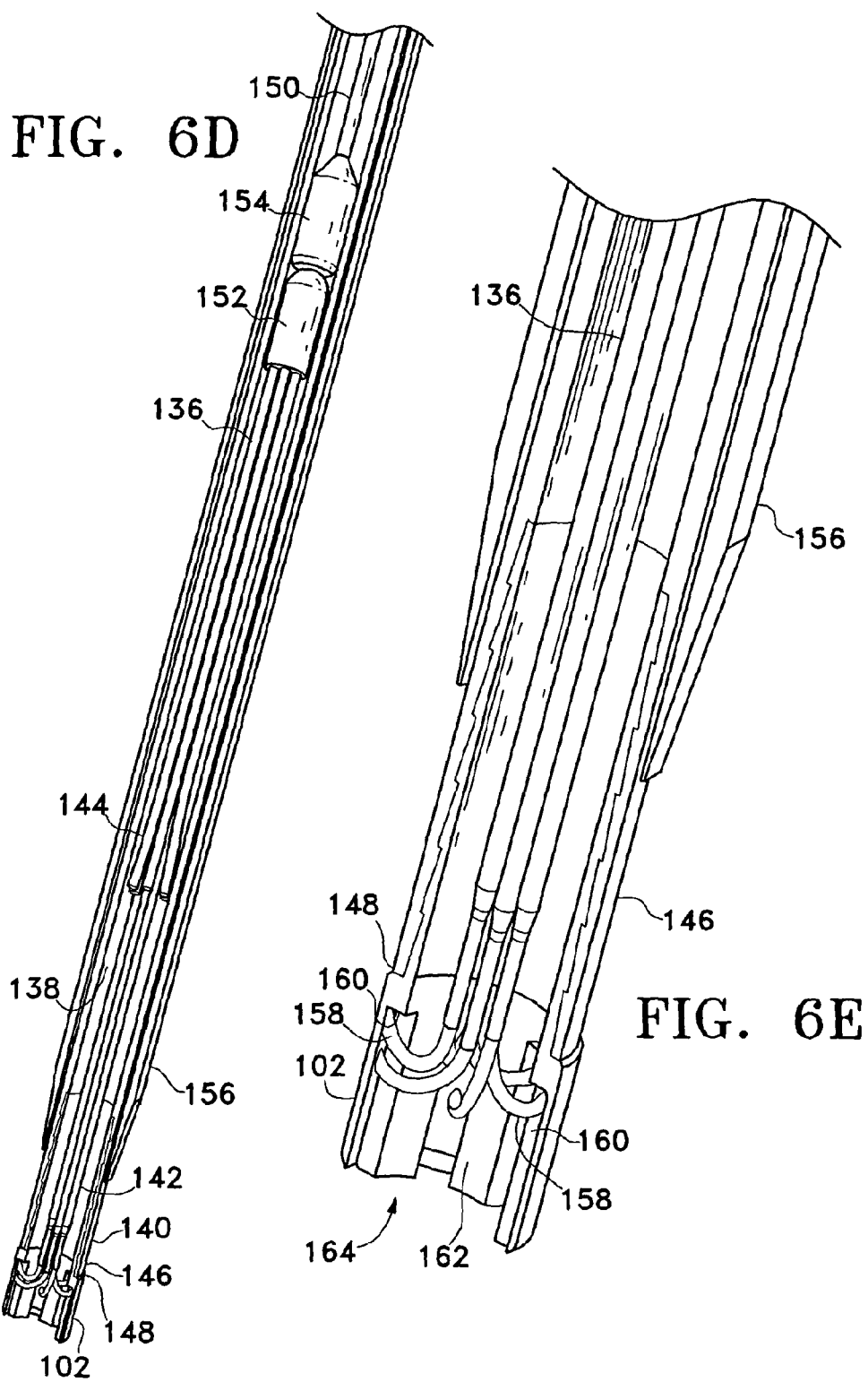

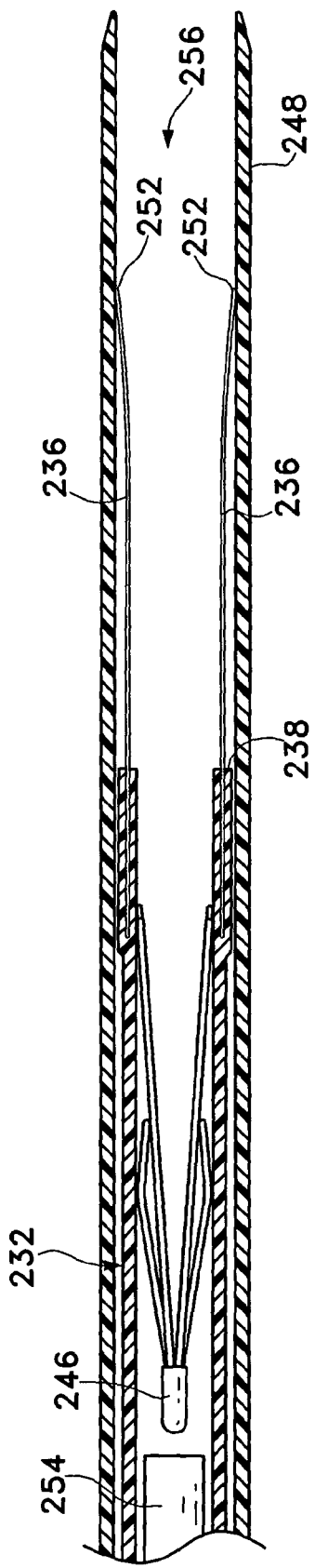
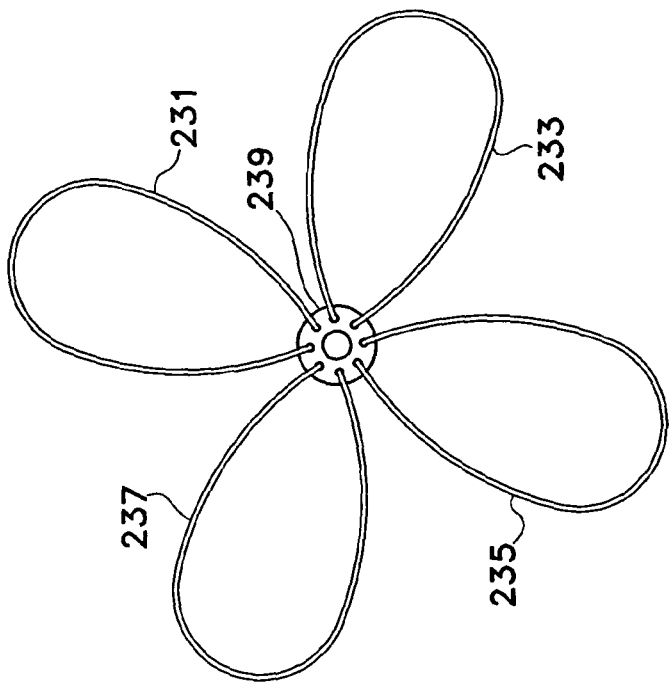
FIG. 7C
FIG. 7D

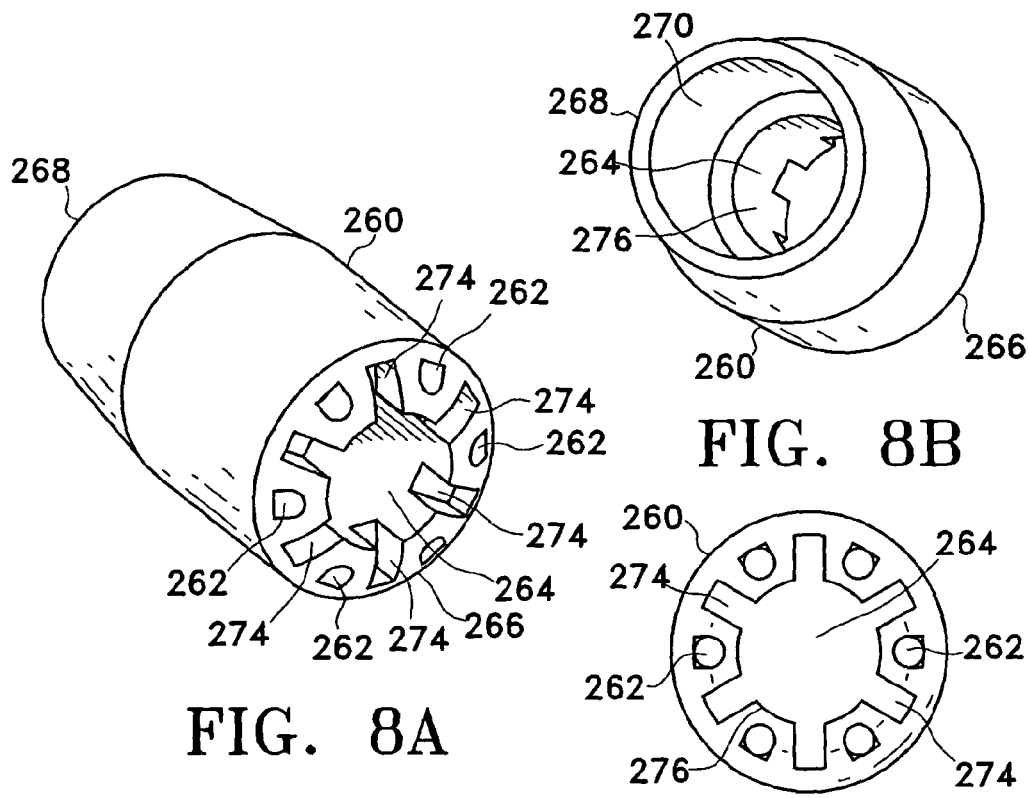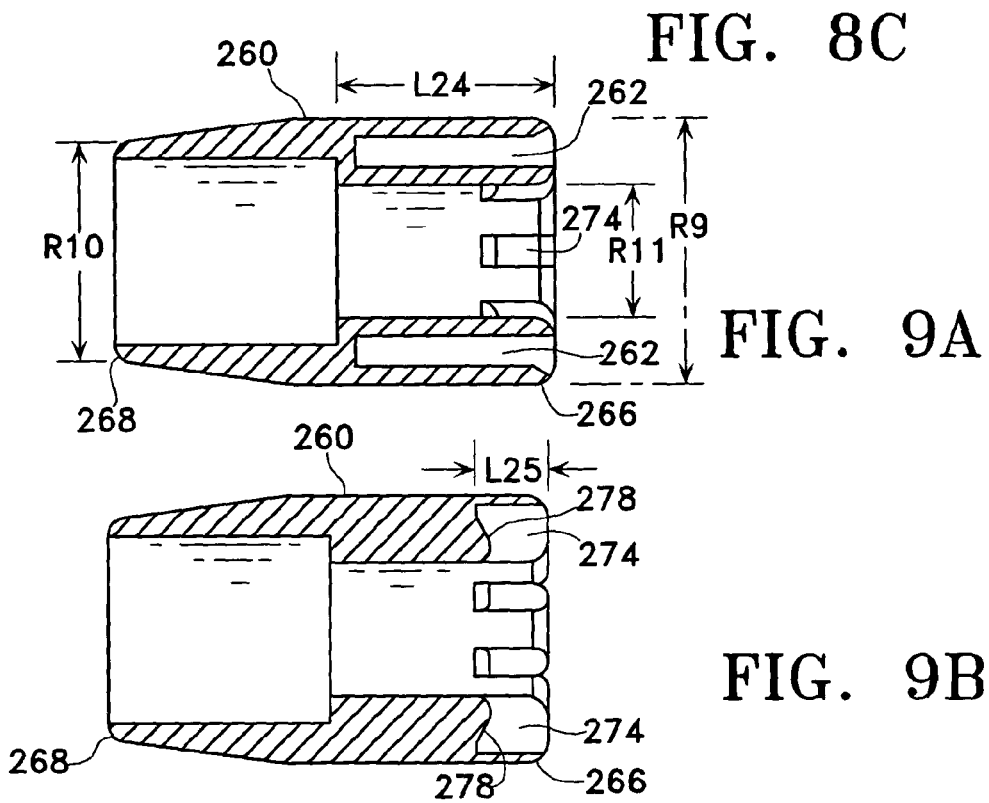

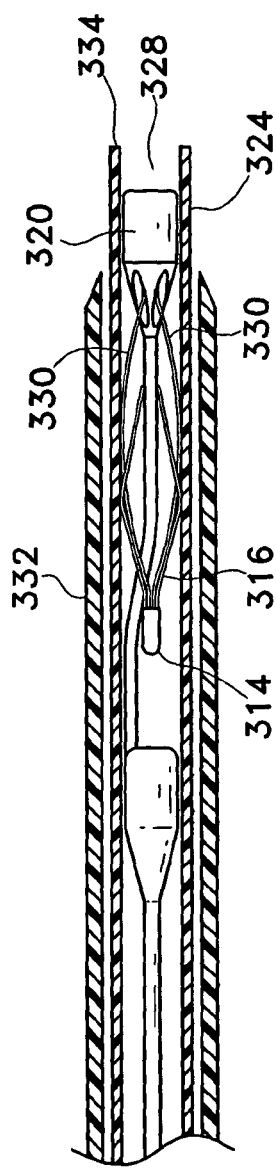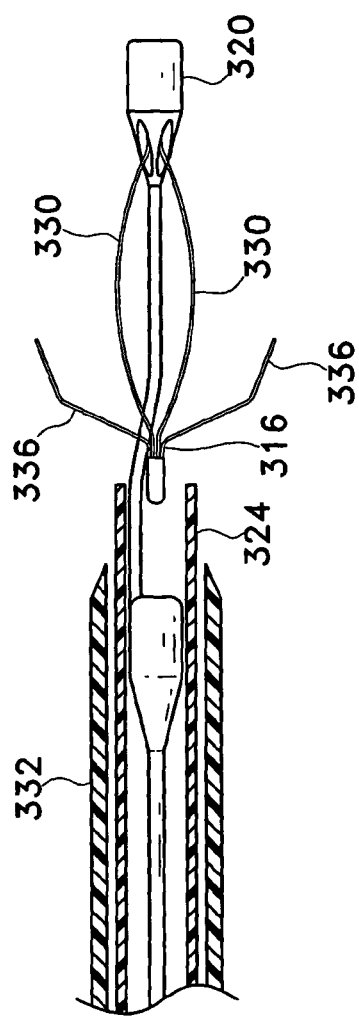
FIG. 14A
FIG. 14B

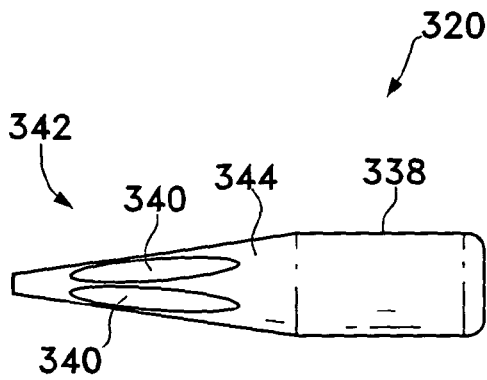
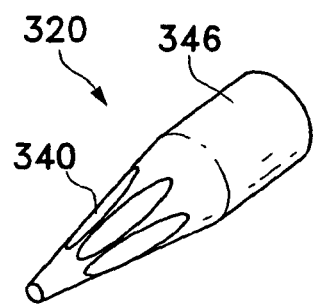
FIG. 15A
FIG. 15B
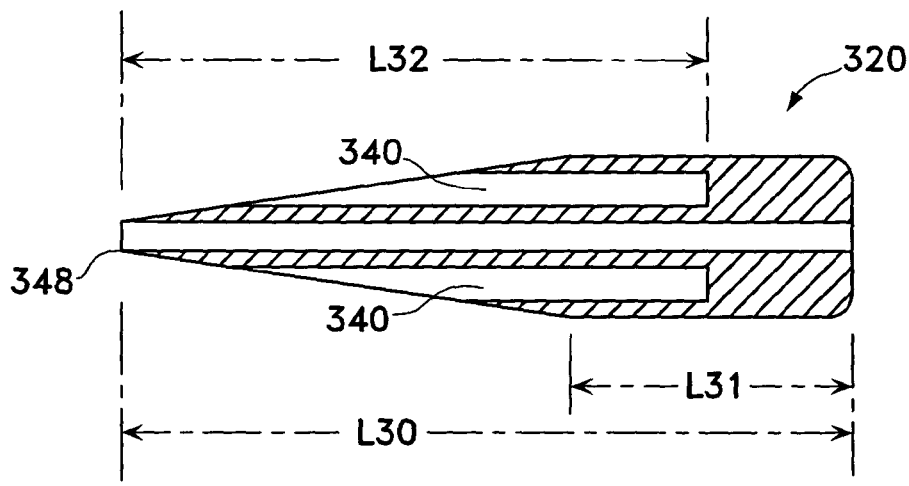
FIG. 15C
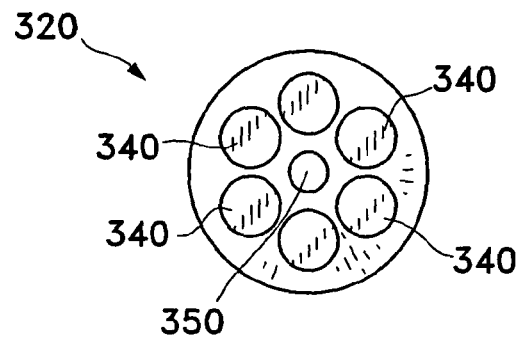
FIG. 15D

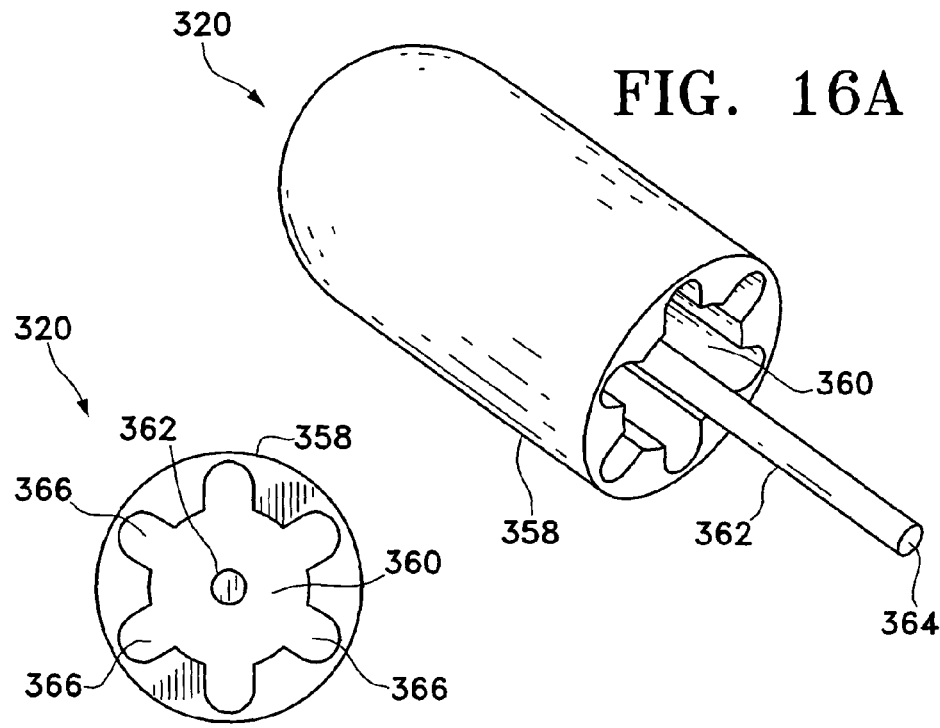
FIG. 16A
FIG. 16B
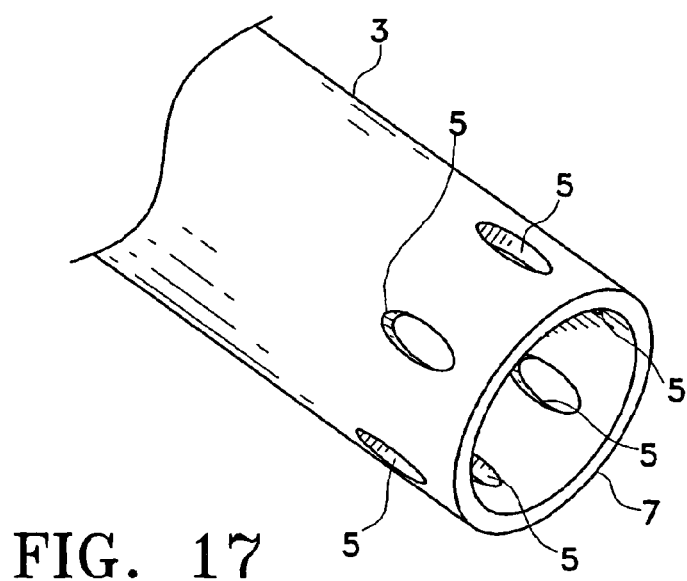
FIG. 17

FILTER DELIVERY SYSTEM

CROSS-REFERENCE TO RELATED APPLICATIONS

This is a continuation of U.S. patent application Ser. No. 10/986,714, filed 12 Nov. 2004, now U.S. Pat. No. 7,794,473, which is incorporated herein by reference.

STATEMENT REGARDING FEDERALLY SPONSORED RESEARCH OR DEVELOPMENT

Not applicable

REFERENCE TO A "MICROFICHE APPENDIX"

Not applicable

BACKGROUND OF THE INVENTION

1. Field of the Invention

The present invention relates to vessel filters and vessel delivery systems. More particularly, the present invention relates to an improved vessel filter and delivery system having a delivery catheter of improved configuration that accepts a filter in a folded condition wherein the filter has specially configured appendages with outwardly directed hooks that engage indentations or recesses in the catheter wall.

2. General Background of the Invention

A vessel filter is a device inserted into a blood vessel to capture particles in the blood flow. Typically the device is inserted into a major vein to prevent a blood clot from reaching the lungs. Patients, who have recently suffered from trauma, have experienced a heart attack (myocardial infarction), or who have undergone major surgical procedure (e.g., surgical repair of a fractured hip, etc.) may have thrombosis in a deep vein. When the thrombus clot loosens from the site of formation and travels to the lung it may cause pulmonary embolism, a life-threatening condition. A vessel filter may be placed in the circulatory system to intercept the thrombi and prevent them from entering the lungs.

Examples of various blood vessel filters and delivery systems are disclosed in the following table:

TABLE

| PATENT NO. | TITLE | ISSUE DATE |
|---|---|---|
| 2001/0000799 A1 | "BODY VESSEL FILTER" | May 3, 2001 |
| 2002/0038097 A1 | "ATRAUMATIC ANCHORING AND DISENGAGEMENT MECHANISM FOR PERMANENT IMPLANT DEVICE" | Sep. 26, 2002 |
| 2002/0193828 A1 | "ENDOVASCULAR FILTER" | Dec. 19, 2002 |
| 2003/0199918 A1 | "CONVERTIBLE BLOOD CLOT FILTER" | Oct. 23, 2003 |
| 2003/0208227 A1 | "TEMPORARY VASCULAR FILTERS AND METHODS" | Nov. 6, 2003 |
| 2003/0208253 A1 | "BLOOD CLOT FILTER" | Nov. 6, 2003 |
| 2004/0082966 A1 | "STAGED RELEASE OF IVC FILTER LEGS" | Apr. 29, 2004 |
| 4,425,908 | "BLOOD CLOT FILTER" | Jan. 17, 1984; |
| 4,643,184 | "EMBOLUS TRAP" | Feb. 17, 1987; |
| 4,817,600 | "IMPLANTABLE FILTER" | Apr. 4, 1989; |
| 5,059,205 | "PERCUTANEOUS ANTI-MIGRATION VENA CAVA FILTER" | Oct. 22, 1991; |
| 5,147,379 | "INSERTION INSTRUMENT FOR VENA CAVA FILTER" | Sep. 15, 1992; |
| 5,626,605 | "THROMBOSIS FILTER" | May 6, 1997; |
| 5,634,942 | "ASSEMBLY COMPRISING A BLOOD FILTER FOR TEMPORARY OR DEFINITIVE USE AND A DEVICE FOR IMPLANTING IT" | Jun. 3, 1997; |
| 5,755,790 | "INTRALUMINAL MEDICAL DEVICE" | May 26, 1998; |
| 5,853,420 | "ASSEMBLY COMPRISING A BLOOD FILTER FOR TEMPORARY OR DEFINITIVE USE AND A DEVICE FOR IMPLANTING IT, CORRESPONDING FILTER AND METHOD OF IMPLANTING SUCH A FILTER" | Dec. 29, 1998; |
| 6,258,026 B1 | "REMOVABLE EMBOLUS BLOOD CLOT FILTER AND FILTER DELIVERY UNIT" | Jul. 10, 2001; |
| 6,342,062 B1 | "RETRIEVAL DEVICES FOR VENA CAVA FILTER" | Jan. 29, 2002; |
| 6,383,193 B1 | "VENA CAVA DELIVERY SYSTEM" | May 7, 2002; |
| 6,497,709 B1 | "METAL MEDICAL DEVICE" | Dec. 24, 2002; |
| 6,506,205 B2 | "BLOOD CLOT FILTERING SYSTEM" | Jan. 14, 2003; |
| 6,517,559 B1 | "BLOOD FILTER AND METHOD FOR TREATING VASCULAR DISEASE" | Feb. 11, 2003; |
| 6,540,767 B1 | "RECOILABLE THROMBOSIS FILTERING DEVICE AND METHOD" | Apr. 1, 2003; |
| 6,620,183 B2 | "THROMBUS FILTER WITH BREAK-AWAY ANCHOR MEMBERS" | Sep. 16, 2003; |

Each of above listed patents is incorporated herein by reference in its entirety.

Typically, the filter comprises a plurality of radially expandable legs that support one or more filter baskets having a conical configuration. The device is configured for compression into a small size to facilitate delivery into a vascular passageway and is subsequently expandable into contact with the inner wall of the vessel. The device may later be retrieved from the deployed site by compressing the radially expanded legs and the associated baskets back into a small size for retrieval. The radially expandable leg may further comprise engagements for anchoring the filter in position within a blood vessel (e.g., vena cava). For example, the expandable legs may have hooks that can penetrate into the vessel wall and positively prevent migration of the filter in either direction along the length of the vessel. The body of the filter may comprise various biocompatible materials including compressible spring metals and shape memory materials to allow easy expansion and compression of the filter within the vessel. The hooks on the radially expandable legs may further comprise materials more elastic than the legs to permit the hooks to straighten in response to withdrawal forces to facilitate withdrawal from the endothelium layer without risk of significant injury to the vessel wall. The hooks may be formed on selected radially expandable legs, but not on others.

Many of the existing vena cava filters routinely encounter problems during deployment due to entanglements of the radially expandable legs. This is especially problematic in designs with hooks implemented on the radially expandable legs. In the compressed/collapsed condition, the various hooks on the legs may interlock with other legs or hooks and render the device useless. Thus, an improved vessel filter delivery device that can prevent entanglement and/or interlocking of the radially expandable legs when the filter is collapsed and placed inside the delivery device is desirable.

BRIEF SUMMARY OF THE INVENTION

Accordingly, described herein is a vessel filter delivery device with a built-in mechanism for preventing the hooks on the radially expandable legs from interlocking when the vessel filter is compressed and inserted into the lumen of a delivery catheter. The improved vessel filter delivery device may also prevent the radially expandable legs from becoming entangled. In one variation, the vessel filter delivery device comprises an elongated catheter configured with a plurality of grooves at the distal opening to separate the hooks on a vessel filter loaded in the lumen of the catheter. Preferably, each of the grooves has one end that opens at the distal tip of the catheter to allow the hooks to slide out without obstruction, and the proximal end of the groove is configured with a ledge to prevent the catheter from migrating toward the proximal end of the catheter, keeping the vessel filter at the proximal end of the catheter lumen. The ledge may be configured with a profile approximating the curvature of the hook to help maintain the shape of the hook while the vessel filter is loaded inside the delivery catheter. The profile on the ledge may also be configured to minimize fatigue of the material comprising the hook. This feature may be particularly useful for hooks comprised of a shape memory material. Furthermore, a pusher-wire with an attachment interface at the distal end for capturing the head or the sleeve of the vessel filter may be utilized for loading and unloading the vessel filter from the catheter.

In another variation, the vessel filter delivery device is configured with a mechanism for centering the delivery catheter prior to deploying the vessel filter. In one example, the delivery catheter is configured with a plurality of flexible elements extending from the distal end of the catheter and flaring outward from the longitudinal axis of the catheter. When the delivery catheter is disposed within an introducer sheath, the wall of the introducer sheath compresses the plurality of wirings and allows the advancement of the catheter within the introducer sheath. As the introducer sheath is retracted from the distal end of the delivery catheter, the flexible elements protrude and expand from the distal opening of the sheath, and as a result, center the distal end of the catheter within the blood vessel. Centering of the delivery catheter may allow smoother deployment of the vessel filter, and also assist the legs of the vessel filter to expand evenly and center itself within the blood vessel. The deployment catheter with a centering mechanism may also be configured with grooves at the distal end of the lumen to prevent the hooks and legs of the vessel filter from entanglement.

In yet another variation, the vessel filter delivery device comprises a pusher-wire with an integrated receptacle for holding and separating the hooks on the legs of the vessel filter. The receptacle may prevent interlocking of the hooks and entanglement of the legs. The preloading of the hooks into the receptacle may also facilitate the loading of the vessel filter into the lumen of the catheter. In one example, the pusher device comprises an elongated wire with a pusher pad attached to the distal end thereof. An extension wiring connects a receptacle to the distal end of the pusher pad. The receptacle may be configured with a plurality of orifices. Each orifice is configured to receive a filter hook and/or its corresponding leg.

The improved vessel filter delivery device may provide one or more of the various advantages listed below: improved placement of the vessel filter in the delivery device; prevent loaded vessel filter from migrating towards the proximal end of the delivery device; minimization of fatigue of the vessel filter hooks while the vessel filter is loaded within the delivery device; improved deployability due to easier release of the radially expandable legs; improved deployment orientation and position of the vessel filter, which may result in improved trapping of significant emboli, good vessel patency, limited thrombogenic response at the implantation site, and a decrease in the risk of the hooks perforating the vessel wall.

These and other embodiments, features and advantages of the present invention will become more apparent to those skilled in the art when taken with reference to the following more detailed description of the invention in conjunction with the accompanying drawings that are first briefly described.

BRIEF DESCRIPTION OF THE SEVERAL VIEWS OF THE DRAWINGS

For a further understanding of the nature, objects, and advantages of the present invention, reference should be had to the following detailed description, read in conjunction with the following drawings, wherein like reference numerals denote like elements and wherein:

FIG. 6A is a perspective view of another variation of a spline cap. In this design, the proximal portion of the spline cap is configured for insertion into the lumen of a catheter.

FIG. 6B is a cross-sectional view of the spline cap of FIG. 6A.

FIG. 6C is a frontal view of the spline cap of FIG. 6A. The spline cap is shown from the distal end down its longitudinal axis.

FIG. 6D illustrates an example of a filter delivery system with the spline cap of FIG. 6A implemented at the distal end of the delivery catheter. A vessel filter and a pusher-wire are positioned within the lumen of the delivery catheter. The delivery catheter is slidably disposed within the lumen of an introducer sheath.

FIG. 6E is an expanded view of the distal portion of the filter delivery system shown in FIG. 6D, illustrating the placement of the vessel filter hooks within the grooves on the inner surface of the spline cap.

FIG. 7C illustrates a vessel filter positioned within the lumen of a delivery catheter with distal end centering wirings. The delivery catheter is shown positioned within the lumen of an introducer sheath.

FIG. 7D illustrates another variation of a centering mechanism comprising a plurality of loops connected to the distal end of the catheter.

FIG. 8A is a perspective view of another variation of a spline cap with six slots for receiving filter hooks, and six holes for the placement of centering wirings.

FIG. 8B is a perspective view of the spline cap of FIG. 8A, shown at a different angle.

FIG. 8C is a frontal view of the spline cap of FIG. 8A. The spline cap is shown from the distal end down its longitudinal axis.

FIG. 9A is a cross-sectional view of the spline cap of FIG. 8A.

FIG. 9B is a cross-sectional view of the spline cap of FIG. 9A, shown with the spline cap rotated 30 degree along its longitudinal axis.

FIG. 14A illustrates the filter delivery system of FIG. 13 with a vessel filter loaded on the pusher device. The delivery catheter and its corresponding pusher device are placed within the lumen of an introducer sheath.

FIG. 14B illustrates the partial release of the vessel filter of FIG. 14A. The arms of the filter are shown in an expanded position, while the legs with their corresponding hooks are still secured by the receptacle on the pusher device.

FIG. 15A is a side view of one variation of a filter hook receptacle.

FIG. 15B is a prospective view of the filter hook receptacle of FIG. 15A.

FIG. 15C is a cross-sectional view of the filter hook receptacle of FIG. 15A.

FIG. 15D is a frontal view of the filter hook receptacle of FIG. 15A. The filter hook receptacle is shown from its proximal end down its longitudinal axis.

FIG. 16A is a prospective view of another variation of a filter hook receptacle.

FIG. 16B is a frontal view of the filter hook receptacle of FIG. 16A. The filter hook receptacle is shown from its proximal end down its longitudinal axis.

FIG. 17 illustrates another variation of a delivery catheter where a plurality of orifices are provided at the distal portion of the catheter for receiving and separating the hooks from a vessel filter inserted into the lumen of the catheter.

As shown in FIG. 18, in this variation, the slots spanned across the thinness of the catheter wall.

DETAILED DESCRIPTION OF THE INVENTION

The following detailed description should be read with reference to the drawings, in which identical reference numbers refer to like elements through out the different figures. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

Before describing the present invention, it is to be understood that unless otherwise indicated, this invention need not be limited to applications in humans. As one of ordinary skill in the art would appreciate, variations of the invention may be applied to other mammals as well. Moreover, it should be understood that embodiments of the present invention may be applied in combination with various vessel filters, guidewires, catheters, tubing introducers or other filter deployment devices for implantation of a filter in a vessel within a patient's body.

A vena cava filter is used herein as an example application of the filter deployment device to illustrate the various aspects of the invention disclosed herein. In light of the disclosure herein, one of ordinary skill in the art would appreciate that variations of the filter deployment device may be applicable for placement of filters in various blood vessels, hollow body organs or elongated cavities in a human body. It is also contemplated that the vessel filter described herein may be implemented for capturing particles other than blood clots.

It must also be noted that, as used in this specification and the appended claims, the singular forms "a," "an" and "the" include plural referents unless the context clearly dictates otherwise. Thus, for example, the term "a hook" is intended to mean a single hook or a combination of hooks, "a fluid" is intended to mean one or more fluids, or a mixture thereof. Furthermore, the words "proximal" and "distal" refer to directions closer to and away from, respectively, a physician operating the delivery catheter with the tip end (i.e., distal end) placed inside the patient's body. Thus, for example, the catheter end placed in the vena cava of the patient would be the distal end of the catheter, while the catheter end outside the patient's body would be the proximal end of the catheter.

Figure 1:
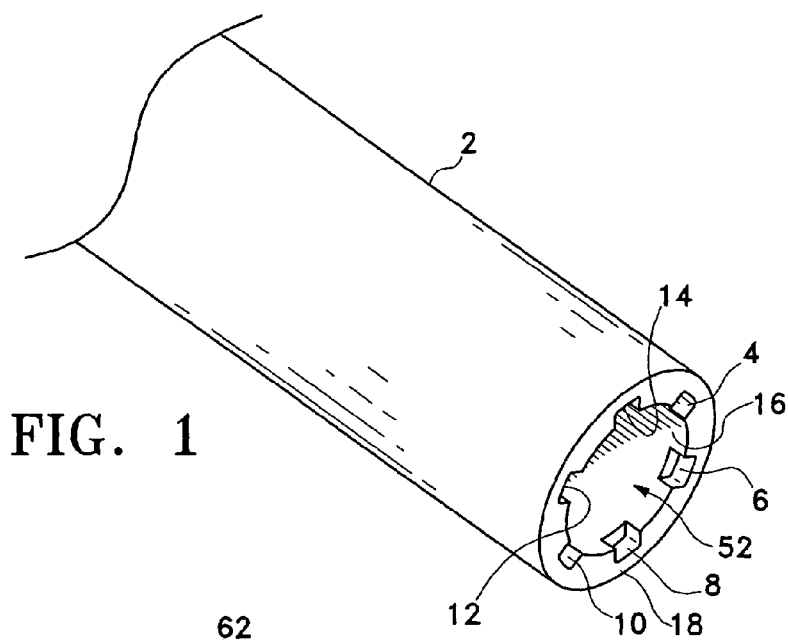
FIG. 1 illustrates one variation of a delivery catheter comprising a catheter with grooves at the distal lumen for receiving the hooks at the distal end of the vessel filter.

Referring to FIG. 1, a delivery catheter 2 configured for securing a vessel filter and placing the vessel filter to a desired location within a patient's vascular system is illustrated. In this variation, the catheter 2 is configured with six grooves 4, 6, 8, 10, 12, 14, (e.g., slots, notches, surface indentations, etc.) positioned on the inner surface 16 of the catheter 2 at the distal end 18 of the catheter. The six grooves 4, 6, 8, 10, 12, 14, are configured to receive six hooks 20, 22, 24, 26, 28, 30 on a corresponding vessel filter 32. The grooves 4, 6, 8, 10, 12, 14 are design to prevent the hooks 20, 22, 24, 26, 28, 30 and their corresponding legs 34, 36, 38, 40, 42, 44 from entangling with each other. In addition, because the grooves allow the hooks to remain in an expanded normal state while loaded in the catheter, the grooves may also minimize stress on the hooks. The delivery catheter may comprise a continuous piece of tubing with grooves etched into the distal end thereof. Alternatively, the delivery catheter may comprise elongated flexible tubing with a spline cap configured with grooves attached to the distal end of the tubing, as will be described in more detail below.

Figure 2:
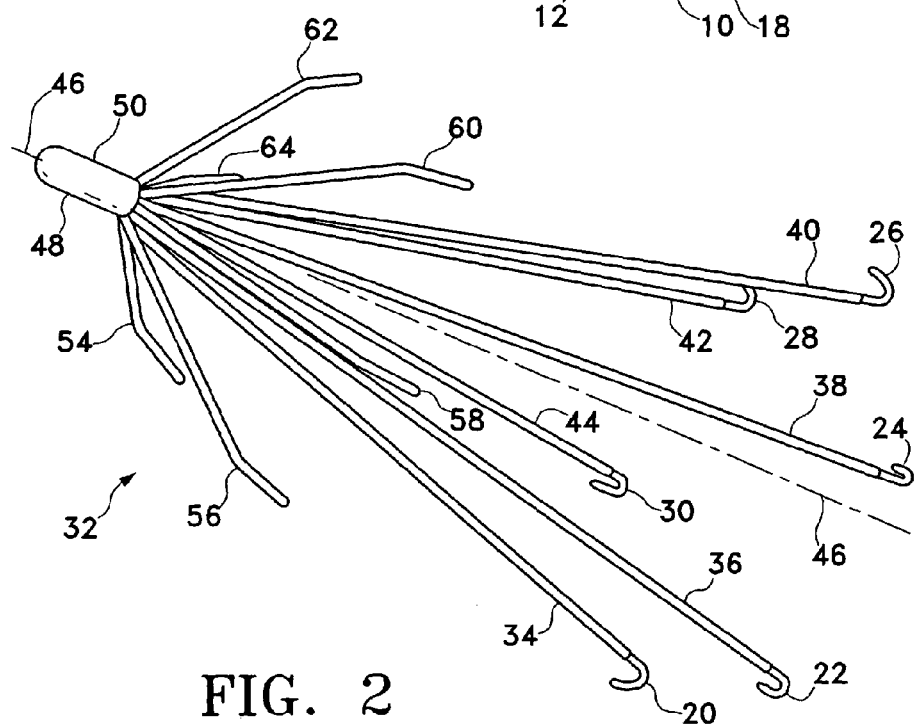
FIG. 2 illustrates one variation of a vessel filter in an expanded position.

A vessel filter 32, such as the one shown in FIG. 2, may be compressed so that the expandable legs 34, 36, 38, 40, 42, 44 on the filter 32 collapse toward a longitudinal axis 46 of the vessel filter 32. The vessel filter 32 in the compressed state may be inserted into the distal end 18 of the delivery catheter 2 with the proximal end 48 (i.e., the end with the sleeve 50) going into the lumen 52 of the catheter 2 first. The legs 34, 36, 38, 40, 42, 44 of the vessel filter 32 may be adjusted such that when the filter 32 is completely inserted into the delivery catheter 2, the hooks 20, 22, 24, 26, 28, 30 on the legs are placed within the corresponding grooves 4, 6, 8, 10, 12, 14 at the distal end 18 of the delivery catheter. Preferably, the grooves are configured to receive the hooks at the distal end of legs only, and not the length of the legs themselves. In an alternative design, the grooves may be configured with longer lengths and/or a deeper profiles such that they may accommodate at least part of the elongated portion of the legs. In addition to separating the hooks and thus their corresponding legs, the grooves may also prevent the filter from rotating within the lumen of the catheter.

In the particular variation of vessel filter shown in FIG. 2, the vessel filter 32 comprises two sets of legs 34, 36, 38, 40, 42, 44, and 54, 56, 58, 60, 62, 64 (e.g., flexible or semi-flexible wiring, etc.) extending from a sleeve 50 in the radial direction towards the distal end 12 of the filter. The legs are configured with materials such that they may be collapsed toward a longitudinal axis 46 of the filter 32 for insertion into a delivery catheter 2. A first set of six legs 54, 56, 58, 60, 62, 64 when expanded, forms a first conical-shaped filter basket centered on the longitudinal axis 46 of the vessel filter 2. A second set of six legs 34, 36, 38, 40, 42, 44, when expanded, forms a second conical-shaped filter basket positioned distal to the first basket, which is also centered on the longitudinal axis 46 of the vessel filter 2. Hooks 20, 22, 24, 26, 28, 30 are provided at the distal ends of the second set of legs 34, 36, 38, 40, 42, 44 for anchoring the distal end of the second set of legs into the walls of the vessel.

Although in the filter example discussed above, the plurality of legs forms two filter baskets along the longitudinal length of the device, one may configure the device with only one filter basket, or alternatively with three or more filter baskets. In addition, the device may be configured with three or more legs forming each basket, and is not limited to the six-legged basket shown in FIG. 2. Also, as discussed above, barb feet (e.g., hooks) may be provided on the distal end of each leg. As one of ordinary skill in the art would appreciate, the precise length and angle of the barb feet may be designed to provide secure attachment to the vessel wall without causing perforation or tearing. Moreover, hooks may be provided on all the distal legs or only on some of the distal legs. Hooks may also be provided on the proximal legs if desired. Furthermore, secondary struts may be provided for interconnecting two or more of the radially expandable legs. The secondary struts may increase wiring density for each filter basket, which may in turn increase the filters capability to capture smaller particles. In addition, the sleeve 50 may be comprised of a biocompatible metal, metal alloy, or polymeric material. The legs 34, 36, 38, 40, 42, 44, 54, 56, 58, 60, 62, 64 may be comprised of a metal (e.g., stainless steel, titanium, etc.), metal alloy (e.g., titanium alloy, Elgiloy, an alloy comprising Cobalt-Nickel-Chromium, etc.), shape memory material (e.g., Nitinol, shape memory alloyed, shape memory polymer, etc.), or polymeric material (e.g., biocompatible plastics, etc.).

Figure 3:
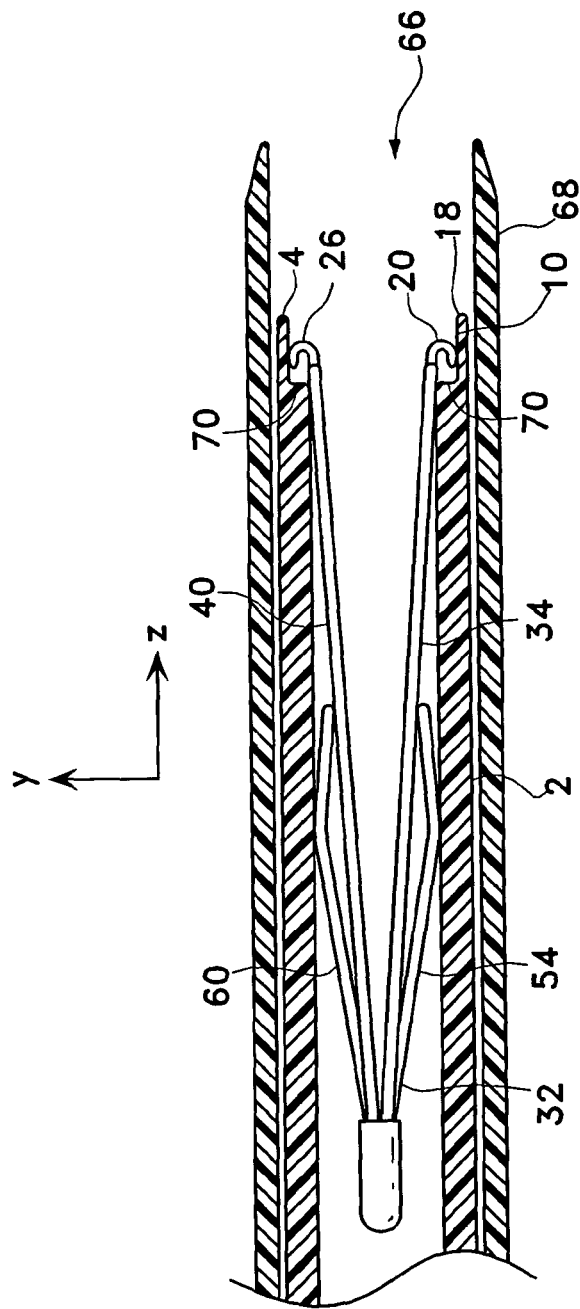
FIG. 3 illustrates an example of a vessel filter positioned within the delivery catheter for deployment. The hooks on the vessel filter are resting within the grooves that are cut into the cross-sectional area at the distal end of the delivery catheter. The delivery catheter is shown positioned within the lumen of an introducer sheath.

Referring to FIG. 3, a vessel filter 32 is placed within a delivery catheter 2, which is slidably disposed in the lumen 66 of an introducer sheath 68. The vessel filter 32 is located within the distal portion of the catheter 2. The wall of the delivery catheter 2 prevents the legs 54, 60, 34, 40 of the vessel filter from expanding. The hooks 20, 26 rest in their corresponding grooves 10, 4 at the distal end 18 of the delivery catheter 2. As shown in FIG. 3, an optional ledge 70 is provided in each of the grooves 10, 4. When the hook rests within the groove, the ledge blocks the hook from moving in the proximal direction. As a result, the vessel filter 32 can not migrate in the proximal direction (−Z) along the length of the catheter 2 lumen.

To deploy the vessel filter, a pusher-wire inserted inside the lumen of the delivery catheter proximal of the vessel filter may be utilized to unload the vessel filter. The pusher-wire may comprise a flexible wiring or a flexible rod with its distal end configured to contact the proximal end of the vessel filter. The pusher-wire may have a pusher pad attached to its distal end. To deploy the vessel filter, one would insert the introducer sheath into the circulatory system through methods well known to one of ordinary skill in the art. The introducer sheath provides a pathway for the physician to advance the delivery catheter loaded with the vessel filter to the desired deployment location. One may then advance the distal tip of the delivery catheter out the distal opening of the introducer sheath. With the distal tip of the pusher-wire positioned just proximal of the proximal end of the vessel filter, the physician may retract both the introducer sheath and the delivery catheter while simultaneously holding the pusher-wire in place to force the vessel filter out of the lumen of the delivery catheter. As the introducer sheath and the delivery catheter are displaced in the proximal direction (−Z) relative to the vessel filter, the filter is deployed into the blood vessel. As the filter slides out of the delivery catheter's lumen, the legs of the vessel filter expand and engage the wall of the blood vessel. Because the hooks are separated by their corresponding grooves, the hooks are prevented from interlocking with one another and a smooth deployment may be achieved.

Figures 4A, 4B:
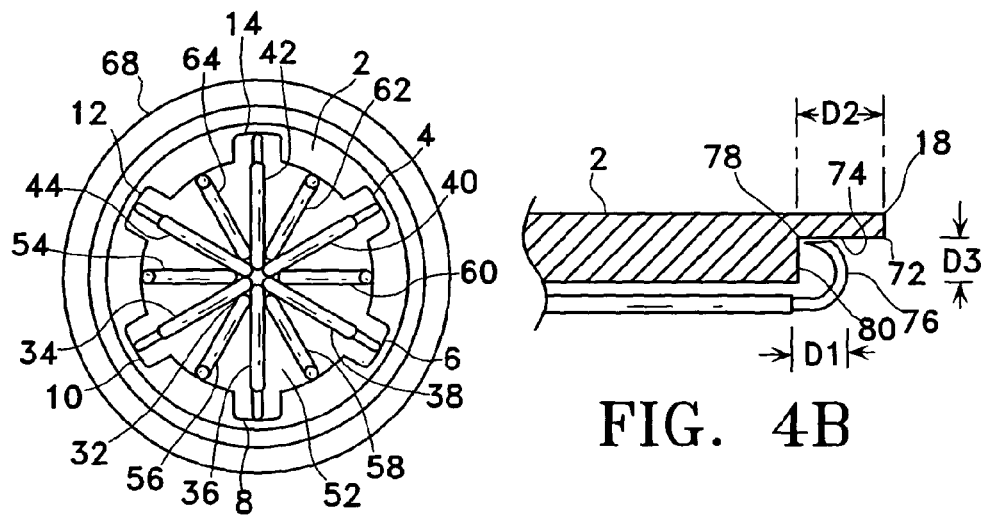
FIG. 4A is the frontal view of the vessel filter delivery system shown in FIG. 3, illustrating the distribution of the vessel filter legs within the lumen of the delivery catheter. The device is shown from the distal end of the delivery catheter down its longitudinal axis.
FIG. 4B is a cross-sectional view illustrating a hook of a vessel filter positioned within a groove in the delivery catheter. The catheter is shown sectioned along the length of the catheter.

In the variation shown in FIG. 4A, the vessel filter 32 is loaded within the lumen 52 of the delivery catheter 2, positioned such that the long legs 34, 36, 38, 40, 42, 44, having hooks at their distal ends aligned with the grooves 10, 8, 6, 4, 14, 12 of the delivery catheter 2, where each of the hooks rest within its corresponding groove. The short legs 54, 56, 58, 60, 62, 64 rest directly on the inner lumen wall of the delivery catheter 2. Although in this example six grooves are provided to support a filter with six hooks, one of ordinary skill in the art having the benefit of this disclosure would appreciate that other combination of grooves (e.g., three, four, five, seven or more) may be implemented to accommodate various filter designs. In addition, one of ordinary skill in the art would appreciate that the grooves may be configured to be various other geometric shapes. The spacing of the groove distribution around the lumen opening may also vary depending on the design of the vessel filter.

Figure 4C:
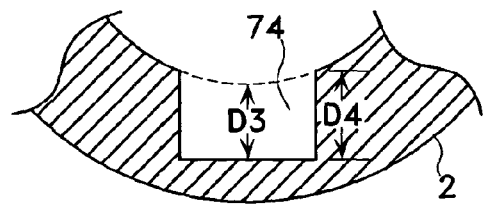
FIG. 4C is a cross-sectional view of a delivery catheter illustrating one variation of a groove on the inner circumferential surface of a delivery catheter.
Figure 4D:
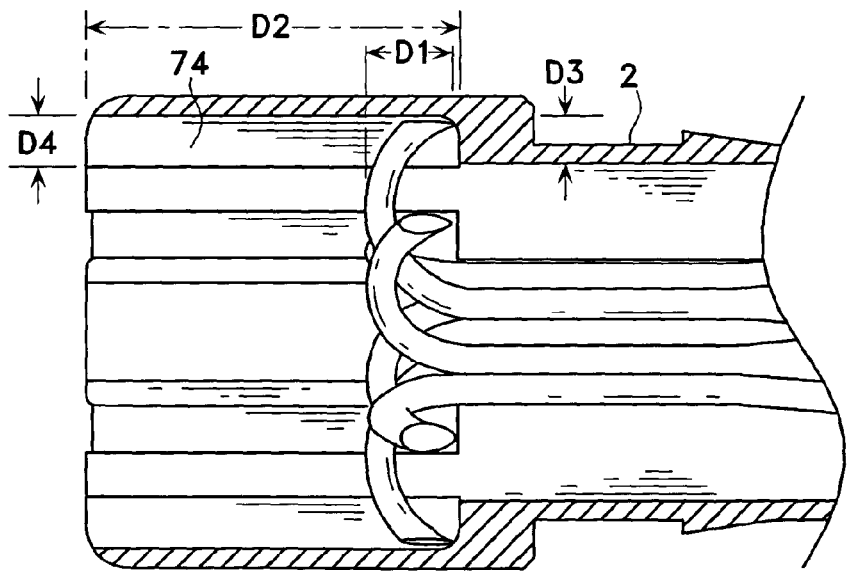
FIG. 4D is a sectional view illustrating the dimension of the grooves on another variation of the delivery catheter. The catheter is shown sectioned along the length of the catheter, with a vessel filter loaded in the lumen of the catheter.

Furthermore, the groove may be configured to extend along the longitudinal axis of the catheter. In the example shown in FIG. 4B, the distal end 72 of the groove 74 is open to allow the hook 76 to easily slide out of the distal end 18 of the delivery catheter 2. The proximal end 78 of the groove 74 is configured with a ledge 80 which may interface with the hook and prevent the vessel filter from migrating in the proximal direction. It is preferable that the length of the groove "D2" along the longitudinal axis of the catheter is one-fourth of an inch or less; more preferably "D2" is one-eighth of an inch or less. Alternatively, one may design the length "D2" of the groove based on the length of the hook "D1" along the longitudinal axis of its corresponding leg. Preferably, "D2" is equal or less than ten times the length of "D1"; more preferably "D2" is equal or less then four times the length of "D1". In addition, it is preferable that the depth "D3" of the grooves is equal or less than 0.06 inches; more preferably, the depth "D3" of the groove is equal to or less than 0.04 inches. The groove may have a constant depth along the circumferential direction. Alternatively, the groove may be designed with varying depths along the circumferential direction. For example, the depth of the groove may be wider at the two edges, and narrower at the center, such that D4>D3, as shown in FIG. 4C. In one particular variation, the groove is designed with a length D2=0.1 inches, the depth of the groove at the two edges D4 are 0.014 inches, while the depth of the groove at the center D3 is 0.013 inches, as shown in FIG. 4D. The particular vessel filter shown in FIG. 4D has a set of six identical hooks with each having a length D1 of about 0.025 inches.

Although in the above examples, each of the delivery catheters has a set of identical grooves, one of ordinary skill in the art having the benefit of this disclosure would appreciate that the delivery catheter may be designed with grooves of varying sizes. For example, the grooves may have varying lengths, widths and depths to accommodate the corresponding vessel filter to be inserted inside the lumen of the delivery catheter. In one variation, the length of the legs on the vessel filter may be varied such that the positions of the hooks are staggered along the longitudinal axis. The delivery catheter may be designed with grooves of varying lengths to accommodate this vessel filter with staggered hooks. In another variation, the vessel filter may have hooks of varying sizes. The delivery catheter may be designed with grooves of varying widths and depths to accommodate the variations in the dimensions of the hooks.

Figure 5A:
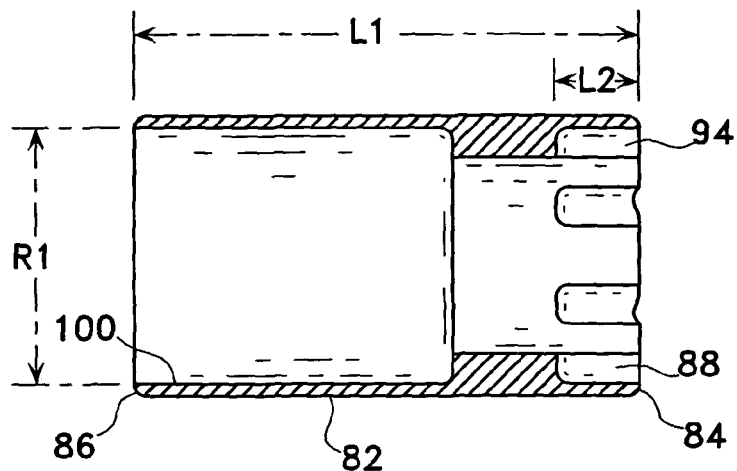
FIG. 5A is a cross-sectional view illustrating one variation of a spline cap. The spline cap is configured for attachment to the distal end of a catheter to provide the hook receiving grooves.
Figure 5B:
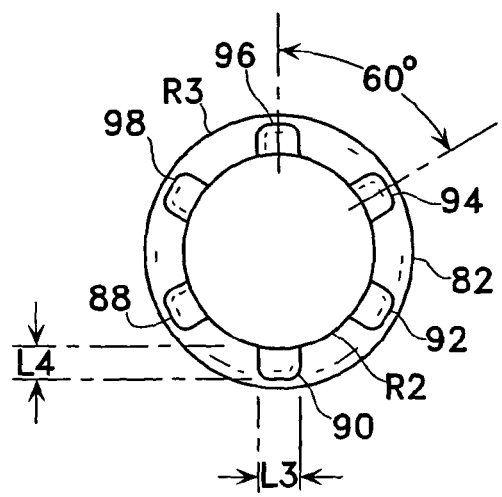
FIG. 5B is a frontal view of the spline cap of FIG. 5A. The spline cap is shown from the distal end down its longitudinal axis.

In another variation, the delivery catheter comprises a spline cap 82 attached to the distal end of a catheter. In one variation, as shown in FIG. 5A, the spline cap 82 comprises a piece of cylindrical metal with a lumen extending from the distal end to the proximal end 86. A plurality of grooves 88, 90, 92, 94, 96, 98 is placed on the inner circumferential surface at the distal end 84 of the spline cap 82 for receiving and separating the hooks on the vessel filter. In this example, the length of the spline cap "L1" is 0.24 inches; the length of the groove "L2" along the longitudinal axis of the spline cap is 0.04 inches. In this variation, a ledge is provided at the proximal end of the groove to prevent proximal migration of the loaded vessel filter. The proximal end of the spline cap is configured with a C-bore 100. The distal end of the catheter may be solvent-bond into the C-Bore 100 of the spline cap 2. The C-Bore has an inner radius "R1" of 0.114 inches. The grooves are evenly distributed in a circumferential manner around the lumen of the spline cap. As shown in FIG. 5B the grooves 88, 90 92, 94, 96, 98 are displaced in 60 degree increments. The width of the groove "L3" is 0.02 inches; the inner diameter "R2" of the spline cap is 0.088 inches, the outer diameter "R3" of the spline cap is 0.124 inches, the depth of the groove "L4" is 0.012 inches. In one particular variation, the delivery catheter is designed to fit within an introducer sheath with a 10 French inner diameter. Such a delivery catheter may be constructed by attaching a spline cap having a low profile design, as described above, to the tip of a catheter of corresponding size.

In addition, in this example, the dimensions of the grooves are configured to accommodate the hooks but not the length of the elongated legs. However, one of ordinary skill in the art having the benefit of the disclosure herein would appreciate the dimension of the grooves may be modified to accommodate both the hooks and the corresponding legs that connects to the hooks. For example, the length of the grooves may be extended and the width widened to accommodate the legs. In addition, one may modify the depth of the grooves to accommodate the length of the legs. In one variation, each groove may be configured with two sections, a proximal section configured to accommodate at least part of the leg, and a distal section configured to receive the corresponding hook (e.g., the distal section may be deeper than the proximal section). Although in the above example, the spline cap comprises a metallic material, one of ordinary skill in the art having the benefit of this disclosure would appreciate that the spline cap may comprise a polymeric material.

72 FIG. 6A illustrates another variation of a spline cap 102. In this variation, the proximal portion 104 of the spline cap 102 is configured for insertion into the lumen of a catheter to form a delivery catheter. Barbs 106, 108, 110, 112, 114, 116 and/or ribs may be provided on the circumferential surface of the spline cap to improve contact between the spline cap 102 and the inner surface of the catheter. Adhesive may also be utilized to secure the spline cap in distal lumen of the catheter. In this example, as shown in FIG. 6B, the overall length "L5" of the spline cap is 0.4 inches; the length "L7" of each of the groove is 0.1 inches; the length "L8" of each of the barb is 0.04 inches; the outer diameter "R4" at the proximal end is 0.98 inches; the diameter "R5" at the edge of each of the barb is 0.104 inches. FIG. 6C is a frontal view of the spline cap 102 showing the six grooves 118, 120, 122, 124, 126, 128 evenly distributed around the lumen 130 in 60 degree increments. The outer diameter "R6" at the distal end 132 of the spline cap is 0.1235 inches, and the inner diameter "R7" is 0.088 inches. The spline cap 102 may be manufacture with sharp edges 134 on the barbs, such that the spline cap 102 may be embedded into the catheter and be securely maintained within the distal end of the catheter.

FIG. 6D illustrates a vessel filter 136 positioned within the lumen 138 of a delivery catheter 140 for deployment. As shown, both the legs 142 and the arms 144 of the vessel filter 136 are in a contracted position. In this example, the delivery catheter 140 comprises a catheter 146 with the spline cap 102 shown in FIG. 6A, inserted within the distal end 148 of the catheter 146. A pusher-wire 150 is also placed within the lumen 138 of the delivery catheter 140 immediately proximal to the sleeve 152 (i.e. head-end) of the vessel filter 136. The distal end of the pusher-wire has a pusher pad 154 to improve contact between the pusher-wire 150 and the vessel filter 136. The delivery catheter 140 is shown slidably positioned within the lumen of an introducer sheath 156. FIG. 6E is an expanded view illustrating the placement of the hooks 158 within the corresponding grooves 160 on the inner wall 162 of the spline cap 102. Each hook 158 is placed within one of the six grooves 160 that are distributed around the distal lumen opening 164.

Figure 6F:
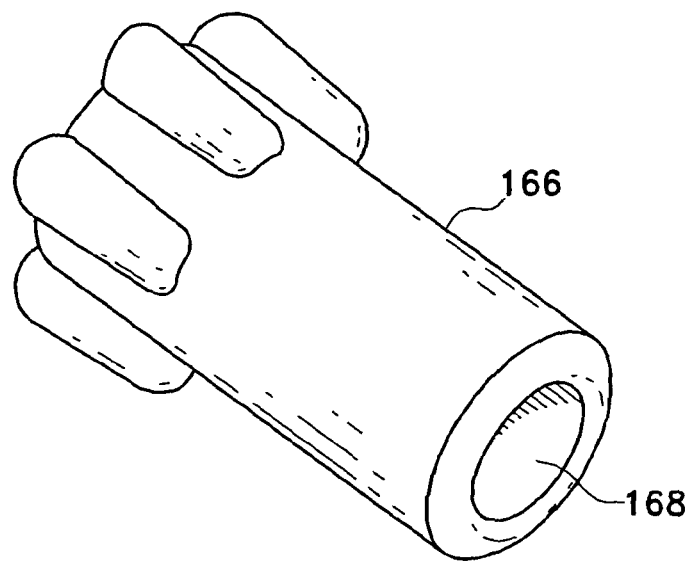
FIG. 6F is a perspective view of one variation of a safety cap. The safety cap is designed for placement over the distal end of a delivery catheter for securing the vessel filter loaded within the distal lumen of the delivery catheter during transport.
Figure 6G:
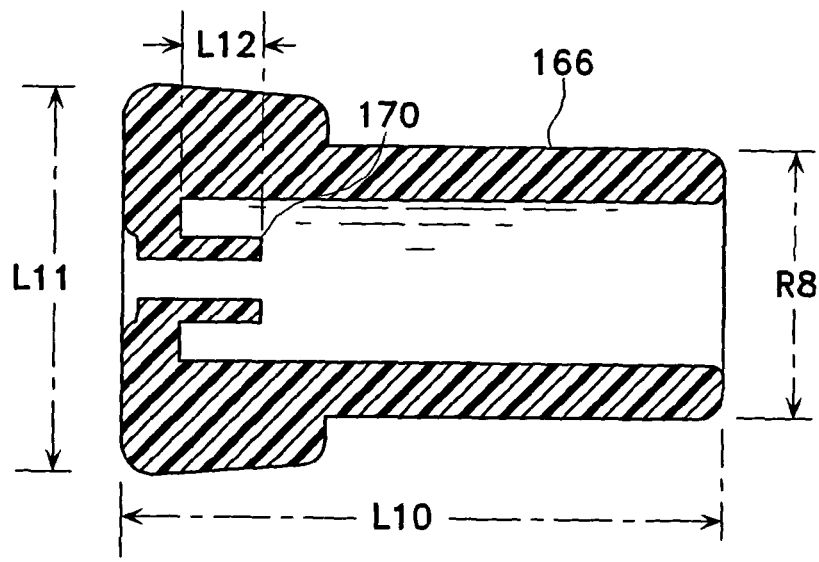
FIG. 6G is a cross-sectional view of the safety cap of FIG. 6F.

FIG. 6F illustrates an optional cap 166 or cover for securing the vessel filter after the vessel filter has been loaded within the lumen of the delivery catheter. The cap is configured for placement over the distal end of the delivery catheter after the vessel filter has been inserted into the distal end of the delivery catheter. The lumen 168 of the cap 166 is wide enough to receive the distal portion of a delivery catheter. The inner base of the cap 166 may be configured with a protrusion 170 such that when the cap 166 is placed over the delivery catheter, the protrusion 170 may advance into the distal lumen of the delivery catheter. The protrusion 170 may engage the hooks to prevent the vessel filter from sliding and may also keep the hooks in their corresponding slot. In this example, the length "L10" of the cap" is 0.44 inches; the length "L12" of the inner protrusion is 0.06 inches; the width "L11" is 0.28 inches; and the diameter "R8" at the proximal end is 0.19 inches. In one application, the vessel filter is loaded into the delivery catheter at the manufacturing site before it is delivered to the hospital for implantation into a patient. A safety cap 166, such as one shown in FIG. 6F may be placed over the distal end of the delivery catheter to keep the filter in place and prevent movement of the vessel filter during transport. When the surgeon is ready to implant the vessel filter, the surgeon may then remove the safety cap and insert the delivery catheter along with the loaded vessel filter into an introducer sheath that has been inserted into the patient's blood vessel.

The vessel filter delivery device disclosed above may be utilized for implantation of a vessel filter into various hollow body organs throughout the human body. In a common application, the vessel filter delivery device is inserted into the jugular vein at the patient's neck or the subclavian vein under the clavicle, for placement of a vessel filter at the inferior vena cava. For example, the implantable vessel filter is prepared by collapsing the legs of the filter and inserting the proximal end (i.e., sleeve or head-end) of the filter into the distal opening of the delivery device, and making sure that the each of the hooks are aligned with its corresponding grooves/cavities on the inner lumen surface at the distal end of the catheter. The compressed vessel filter is positioned with the filter hooks next to the distal opening of the delivery catheter and the proximal end of the vessel filter aligned towards the proximal end of the delivery catheter. The surgeon first locates a suitable jugular or subclavian vein. An incision is made to access the vein. A guidewire is inserted into the vein and advanced towards the inferior vena cava. An introducer sheath together with its tapered dilator is advanced over the guidewire, and the distal portion of the introducer sheath is advanced into the inferior vena cava. The guidewire and the dilator are then removed, leaving the introducer sheath with its tip in the inferior vena cava. Venacavavogram or other imaging techniques may be used to position the introducer sheath for optimal placement of the vessel filter. The filter delivery device loaded with the vessel filter is then inserted into the introducer sheath and advanced toward the inferior vena cava. Once the delivery assembly is positioned for desired placement of the vessel filter, the surgeon holds the pusher-wire in place while simultaneously pulling the introducer sheath and the delivery catheter in a proximal direction. The introducer sheath and the delivery catheter are retracted over the pusher-wire, exposing the vessel filter. The pusher pad at the distal end of the pusher-wire forces the vessel filter to exit the filter delivery device and allows the vessel filter's legs to expand and engage the vessel wall. The delivery assembly and the introducer sheath may then be removed.

Figure 6H:
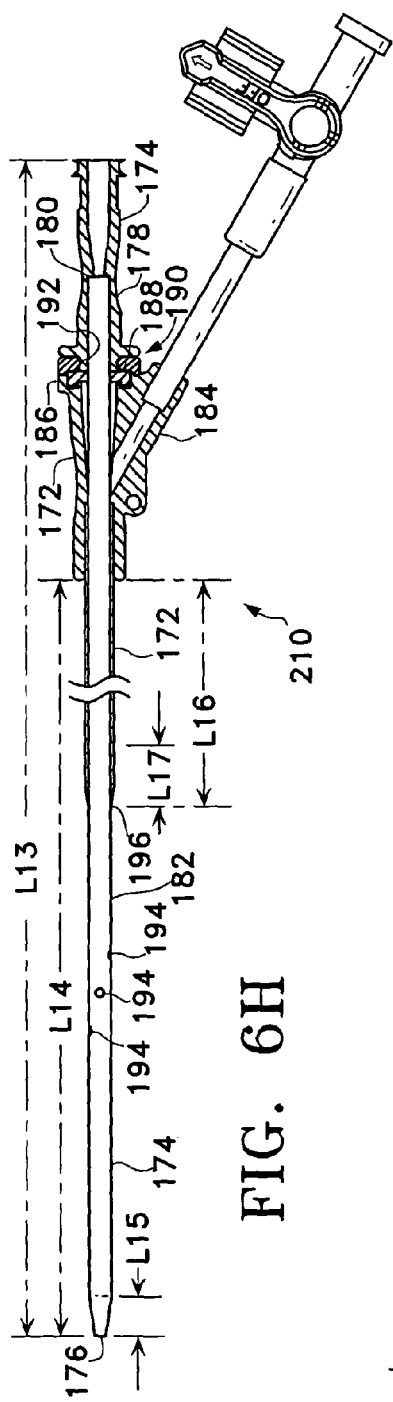
FIG. 6H illustrates one variation of an introducer sheath with its corresponding dilator position within its lumen. The introducer sheath and the dilator are interlocked as a unit for placement over a guidewire.

FIG. 6H illustrates one variation of an introducer sheath 172 and dilator 174 combination. The dilator 174 is slid into the introducer sheath 172 by inserting the distal end 176 of the dilator 174 into the proximal opening of the introducer sheath 172. Once the dilator 174 is advanced all the way into the introducer sheath 172, the dilator hub 178 at the proximal end 180 of the dilator 182 tubing will engage the fluid infusion hub 184 at the proximal end 186 of the introducer sheath 172. An optional interlocking mechanism 188 may be provided to connect the dilator hub 178 to the fluid infusion hub 184 on the introducer sheath 172. The interlocking mechanism 188 may comprise a snap-on interface 190. For example, the fluid infusion hub 184 on the introducer sheath 172 may be configured with a groove/profile for receiving a corresponding protrusion 192 or raised profile on the dilator hub 178, such that the dilator hub 178 may be snapped onto the fluid infusion hub 184 on the introducer sheath 172.

As shown in FIG. 6H, the dilator 174 and the introducer sheath 172 are interlocked together and may be operated as a single unit. In this example, the overall length "L13" of the combined unit is 26.63 inches; the length "L14" of the dilator 174 measured from the base of the fluid infusion hub to the tip 176 of the dilator is 24.43 inches; the length "L15" of the tapered tip portion of the dilator 174 is 0.26 inches; the length "L16" of the introducer sheath 172 measured from the base of the fluid infusion hub to the tip 196 of the sheath is 21.66 inches; and the length "L17" of the tapered distal portion of the introducer sheath is 0.25 inches. Side ports 194 are provided along the length of the distal portion of the dilator such that fluid infused through the dilator 174 may exit the side ports 194 and dilate the blood vessel. The dilator/introducer sheath unit 210 may then be inserted over a guidewire into the patient's circulatory system. Once the distal end 196 of the introducer sheath 172 is placed at the desired location in the blood vessel, the surgeon may disengage the dilator 174 from the introducer sheath 172 and withdrawal the dilator 174 and the guidewire from the lumen of the introducer sheath 172.

With the lumen of the introducer sheath 172 freed of obstructions, the surgeon may then insert a deliver catheter 198 loaded with a vessel filter into the proximal opening on the introducer sheath 172, and advance the delivery catheter 198 along the length of the introducer sheath 172. Once the delivery catheter 198 is inserted all the way into the introducer sheath 172, the fluid infusion hub 202 on the proximal end of the delivery catheter will abut the fluid infusion hub 184 on the proximal end 186 of the introducer sheath 192. An optional interlocking mechanism 180 may be provided to connect the two fluid infusion hubs 184, 202 together, and thereby linking the delivery catheter 198 and the introducer sheath 172 into a single operating unit. The delivery catheter tubing 204 and the introducer sheath 172 may then be displaced over the pusher-wire 206 as a signal unit. The interlocking mechanism 188 may comprise a snap-on interface. For example, the introducer sheath 172 may be configured with a groove/profile for receiving a corresponding protrusion 208 or raised profile on the delivery catheter 198, such that the fluid infusion hub 202 on the delivery catheter 198 may be snapped onto the fluid infusion hub 184 on the introducer sheath 172, as shown in FIG. 6I.

Figure 6I:
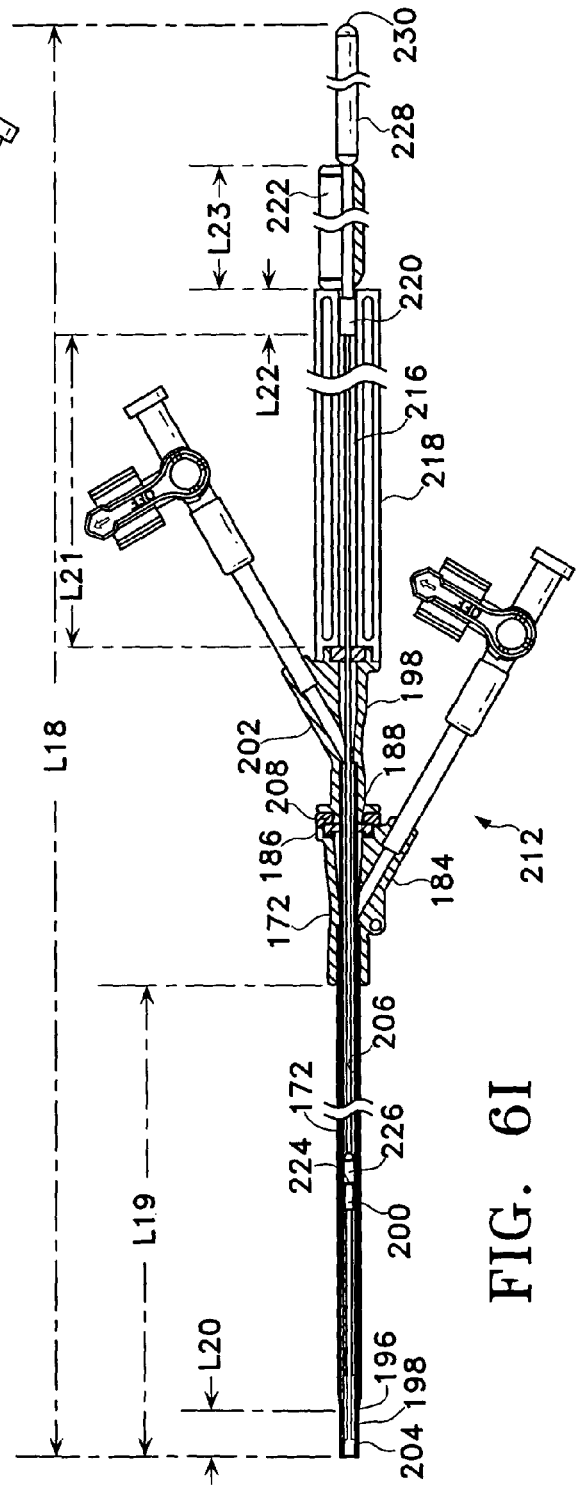
FIG. 6I illustrates the introducer sheath of FIG. 6H with the dilator removed, and a delivery catheter loaded with a vessel filter is inserted in the lumen of the introducer sheath. The distal portion of the delivery catheter is shown interlocked to the introducer sheath such that the dilator and the delivery catheter may be displaced within a blood vessel as a single unit when they are interlocked to each other.

FIG. 6I illustrates a delivery catheter 198 inserted inside the lumen of the introducer sheath 172, and the proximal end of the introducer sheath 186 engages the fluid infusion hub 202 on the delivery catheter 198 and interlocks the two devices together. Also shown in FIG. 6I, a vessel filter 200 is loaded within the distal lumen of the delivery catheter 198 and a pusher-wire 206 is positioned within the proximal lumen of the delivery catheter 198. In this example, the overall length "L18" of the delivery catheter/introducer sheath assembly 212 is 35.32 inches; the length "L19" of the delivery catheter tubing 204 measured from the base of the fluid infusion hub to the tip of the delivery catheter is 21.96 inches; the length "L20" of the portion of the delivery catheter 198 that protrudes from the distal end 196 of the introducer sheath 172 is 0.29 inches; the length "L21" of the channel 216 in the delivery hub extension 218 that accommodates the sliding of the block-stop 220 is 3 inches; the length "L22" measured form the distal end of the block-stop 220 to the proximal end of the delivery hub extension is 0.3 inches; and length "L23" of the safety clip 222, which is also the maximum displacement distance for the pusher-wire 206, is 2.95 inches.

In this example, a delivery hub extension 218 is provided to guide the displacement of the pusher-wire 206. A block-stop 220 which is fixedly connected to the pusher-wire 206 is positioned within a channel 216 in the delivery hub extension housing 218. The block-stop 220 prevents the user from over withdrawal of the pusher-wire 206. As shown in FIG. 6I, when the pusher-wire 206 is fully displaced in the proximal direction, the block-stop 220 abuts the proximal wall of the delivery hub extension 218 and prevents further withdrawal of the pusher-wire 206. Optionally, the block-stop 220 may be configured with a cross-sectional profile, such as square, that matches the inner surface of the delivery hub extension housing 218 to prevent the pusher-wire 206 from rotating. This anti-rotational mechanism may be particularly useful when a deployment jig is implemented at the distal end 224 of the pusher-wire 206, since the rotation of the jig, which engages the vessel filter, may cause the legs of the vessel filter 200 to become entangled with each other. However, in a design utilizing a pusher pad 226, such as the one shown in FIG. 6I, an anti-rotational mechanism is not necessary.

The safety clip 222 prevents the surgeon from prematurely deploying the delivery filter 200 by preventing the pusher-wire 206 from displacing in the distal direction. When the delivery catheter 198 is fully inserted into the introducer sheath and successfully engages the introducer sheath's interlocking mechanism 188, as shown in FIG. 6I, the surgeon may then remove the safety clip 222. Holding the handle 228 at the proximal end 230 of the pusher-wire 206 in place, the surgeon may then retract the delivery catheter/introducer sheath assembly 212, causing the delivery catheter tubing 204 and the introducer sheath 172 to simultaneously displace in the proximal direction and allowing the vessel filter 200 to deploy. Once the vessel filter 200 is successfully deployed, the surgeon may then withdrawal the delivery catheter/introducer sheath assembly 212 from the patient's circulatory system. In the example shown in FIG. 6I, the safety clip 222 comprises a tab such that the surgeon may easily push the safety clip off 222 the pusher-wire 206. Alternatively, a loop may be provided on the safety clip 222 so that the surgeon can easily pull the safety clip 222 off the pusher-wire 206. Instruction for removal of the safety clip 222 may be provided on the safety clip in the form of lettering and/or graphic icon.

Figure 7B:
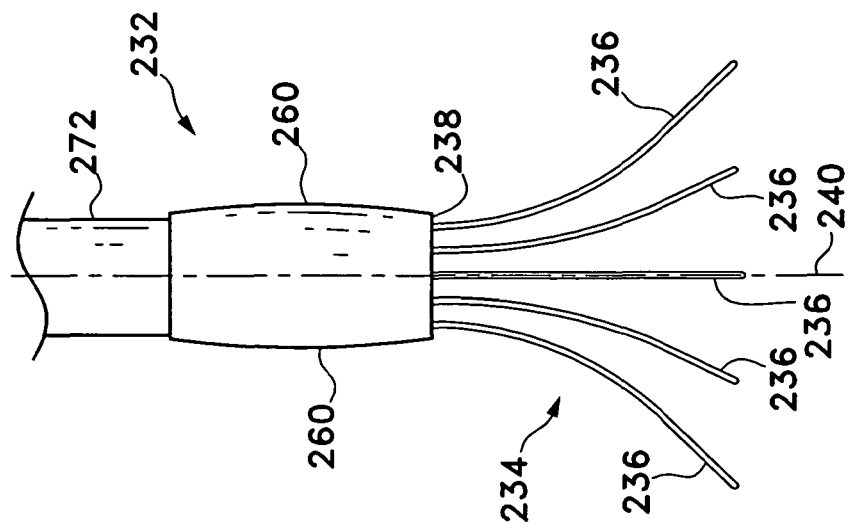
FIG. 7B is a side view of the delivery catheter of FIG. 6A.
Figure 7A:
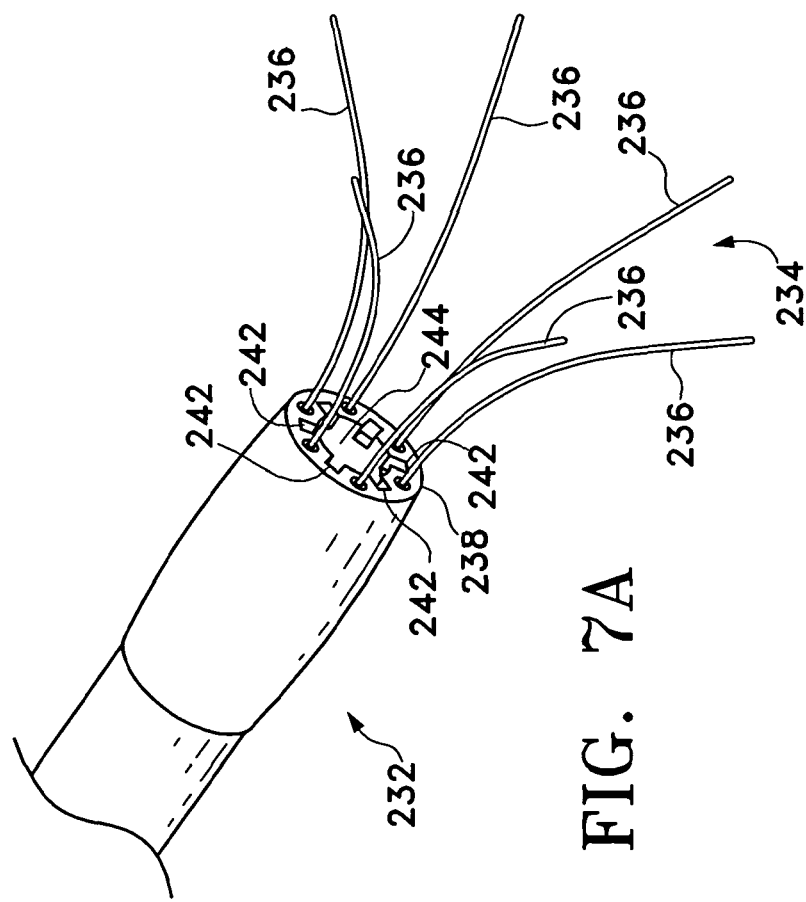
FIG. 7A is a perspective view of another variation of a delivery catheter. In this variation, six wirings are provided at the distal end of the catheter to center the delivery catheter within a vessel.

Referring to FIG. 7A, a delivery catheter 232 with a centering mechanism 234 is illustrated. The centering mechanism 234 comprises a plurality of flexible elements 236 (e.g. wires, rods, etc.) configured around the distal end 238 of the delivery catheter 232 such that the flexible elements 236 flare outward from a longitudinal axis 240 of the catheter 232, as shown in FIG. 7B. The flexible elements may comprise a biocompatible metal, metal alloyed, polymer, or a combination thereof. When the delivery catheter is deployed inside a blood vessel, the flexible elements 236 push against the wall of the blood vessel and center the distal tip 238 of the catheter 232 within the blood vessel. In the example shown in FIG. 7A, the delivery catheter 232 is also configured with an optional feature for separating the hooks of a vessel filter to be loaded into the distal 238 end of the delivery catheter. As shown, grooves 242 are provided at the distal end of the inner lumen for receiving and separating the hooks.

FIG. 7C illustrates a vessel filter 246 loaded in the distal end 238 of a delivery catheter 232. The delivery catheter 232 is slidably disposed within an introducer sheath 248. The wall of the introducer sheath compresses the flexible elements 236 at the distal end of the delivery catheter and allows the physician to advance the delivery catheter 232 within the lumen 250 of the introducer sheath 248. When the introducer sheath 248 is retracted from the distal end 238 of the delivery catheter 232 and exposes the flexible elements 236, the flexible elements 236 will flare outward. The distal end 252 of each of the flexible elements 236 may then contact the vessel wall and pushed against the vessel wall. The collective action of all flexible elements 236 will center the tip of the delivery catheter 232 within the blood vessel. The physician may then deploy the vessel filter 246 by either retracting the delivery catheter 232 and the introducer sheath 248, thereby exposing the vessel filter 246, or by pushing the vessel filter 246 out of the distal end 238 of the delivery catheter 232 with a pusher-wire 254.

Referring to FIG. 7D, another variation of a centering mechanism is illustrated. In this variation, a plurality of loops 231, 233, 235, 237 are connected to the distal end of a catheter 239. The loops may comprise of metallic material, polymeric material, or a combination thereof. In the expended state the loops 231, 233, 235, 237 expand outwardly away from the longitudinal axis of the catheter 239. The catheter may be placed inside of an introducer sheath for deployment. The wall of the sheath forces the loops to collapse inward toward the longitudinal axis. Optional grooves may be provided on the inner wall of the catheter 239 to separate the hooks on a vessel filter loaded within the catheter 239.

In one variation, the flexible elements 236 for centering the catheter 232 is attached to the distal end 238 of a catheter 232 through a spline cap 260 serving as the interface. An example of a spline cap 260 with holes 262 for receiving the flexible elements 236 is shown in FIG. 8A-8C. In this design, the spline cap 260 is configured with a lumen 264 running from the distal end 266 of the spline cap 260 to the proximal end 268 of the spline cap 260, as shown in FIG. 8A. The proximal end 268 of the spline cap is configured with a bore 270 to receive a catheter 272, as shown in FIG. 8B. Six holes 262 are provided on the distal end 266 of the spline cap 260 to receive six flexible elements 236, as shown in FIG. 8C. The flexible elements may comprise of six flexible metal wires, or six flexible polymeric rods, or a combination thereof. Six optional slots 274 are also built into the inner wall 276 of the spline cap 260 for receiving six corresponding hooks on a vessel filter 246. FIGS. 9A and 9B shows the cross-sectional view of the spline cap 260. In this variation, each of the holes 262 for receiving the flexible elements 236 has a length "L24" of 0.138 inches, as shown in FIG. 9A. The diameter of the spline cap 260 at the distal end "R9" is 0.17 inches; the diameter at the proximal end "R10" is 0.14 inches; the diameter of the lumen "R11" is 0.088 inches. The length "L25" of each of the grooves is 0.04. As shown in FIG. 9B, in this example, the ledge 278 at the proximal end of each of the groove 274 is configured with a profile configured to match the curvature of the hook. The curved profile at on the ledge 278 of the groove 274 may help maintain the shape of the distal portion of the hook and/or prevent fatigue of the material comprising the hook.

Figure 10A:
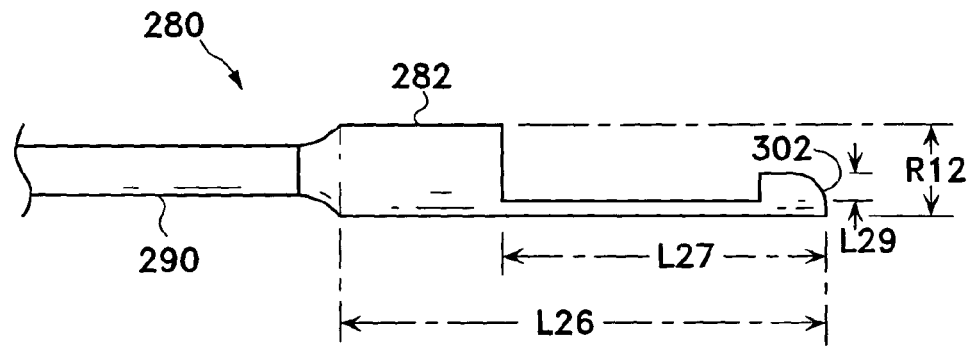
FIG. 10A is a side view illustrating one variation of a pusher-wire having a deployment jig attached to the distal end of the pusher-wire. The deployment jig is configured for loading and unloading the vessel filter into the lumen of a deployment catheter.
Figure 10B:
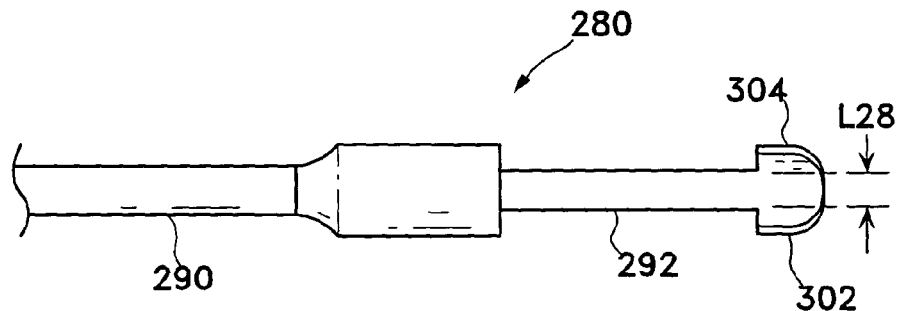
FIG. 10B is a top view of the pusher-wire of FIG. 10A.
Figure 10C:
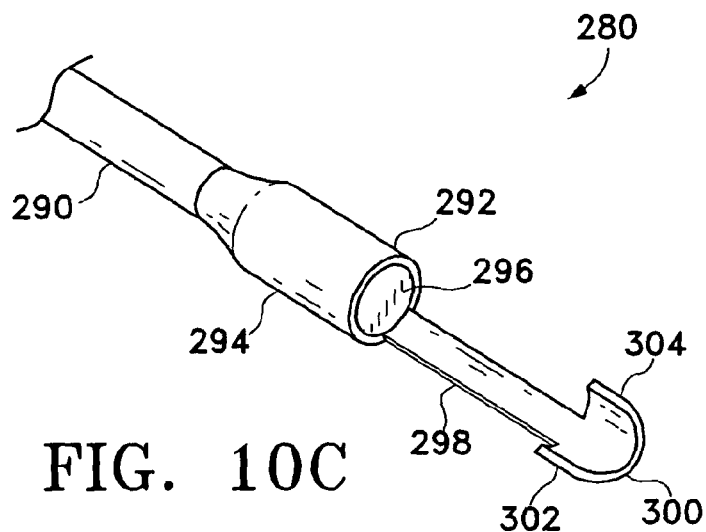
FIG. 10C is a perspective view of the pusher-wire of FIG. 10A.

In another aspect of the invention, a pusher device 280 with an attachment 282 for interfacing with the proximal end 284 of a vessel filter 286 is implemented for loading and unloading of the vessel filter 286 from the delivery catheter 288. The pusher device 280 may comprise a flexible elongated body 290 (e.g., wire, rod, etc.) with a jig 292 attached to the distal end of the flexible elongated body 290, as shown in FIG. 10A. In this example, the jig 292 comprises a base 294 wrapping around the distal tip 296 of the pusher-wire 290, as shown in FIG. 10C. An elongated member 298 extends from the distal end 296 of the pusher-wire in the distal direction. At the distal end 300 of the elongated member, two prongs 302, 304 extend laterally and curve upward for engaging the neck 306 of a vessel filter 286. Referring back to FIGS. 10A and 10B, in this variation, the jig 292 has an overall length "L26" of 0.4 inches and an overall diameter "R12" of 0.072 inches; the elongated member 298 has a length "L27" of 0.25 inches and width "L28" of 0.03 inches; the height "L29" of each of the two prongs 302, 304 is 0.023 inches. The two prongs 302, 304 may have a tapered or rounded atraumatic configuration to prevent the jig 292 form causing damages to the inner wall of a blood vessel during deployment.

Figure 11:
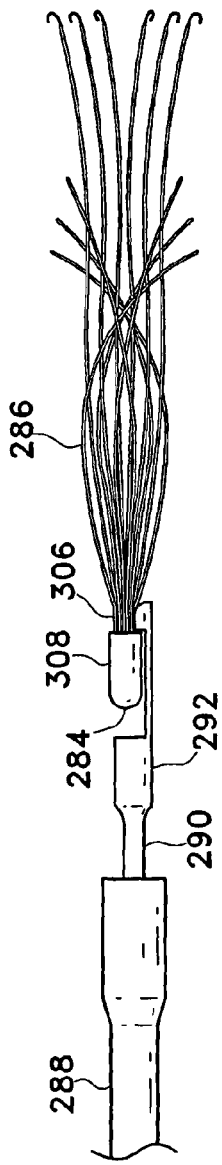
FIG. 11 illustrates a pusher-wire extending from the lumen of a delivery catheter. The deployment jig located at the distal end of the pusher-wires captured the filter sleeve of a vessel filter. The vessel filter is shown in a compressed position.

FIG. 11 illustrates a pusher-wire 290 with a deployment jig 292 at the distal end, extending out the distal lumen of a delivery catheter 288 to engage a vessel filter 286. In this variation, the deployment jig 292 is designed with two lateral prongs 302, 304 which can be placed around the neck 306 of the vessel filter 286 and engages the sleeve 308 or the head of the vessel filter 286. The deployment jig 292 allows the user to pull on the vessel filter 286 and facilitate the loading of the vessel filter 286 into the lumen of the delivery catheter 288. The deployment jig 292 is also designed to release the vessel filter upon deployment by minimizing the surface contact between the vessel filter 286 and the deployment jig 292. One of ordinary skill in the art having the benefit of the disclosure herein would appreciate that other gripping or interlocking mechanism may also be implemented at the distal end of the pusher-wire as the deployment jig for engaging the proximal portion of the vessel filter.

Figure 12:
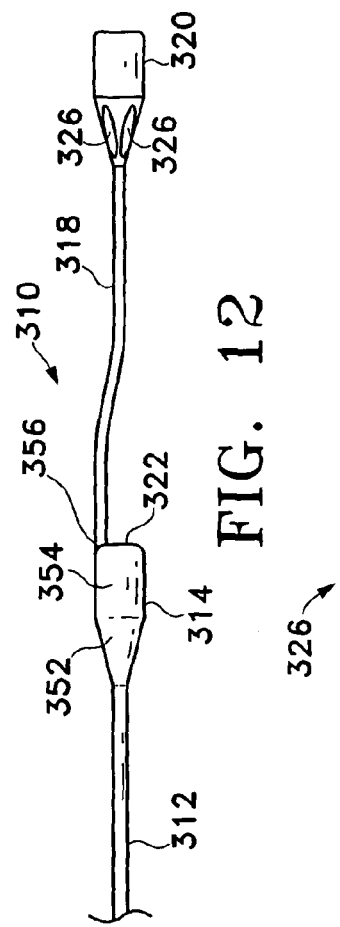
FIG. 12 illustrates another variation of a pusher device. The pusher device comprises a receptacle attached to the pusher pad through a wire. The receptacle is configured with chambers to receive the hooks on the vessel filter.

Referring now to FIG. 12, another variation of a pusher-wire 310 is illustrated. In this design the pusher-wire comprises an elongated flexible body 312 (e.g., wire, rod, etc.), a pusher pad 314 attached to the distal end of the elongated flexible body 312 for applying a force onto the proximal end 314 of the vessel filter 316, and an extension wiring 318 connecting a receptacle 320 to the pusher pad 314. The receptacle 320 is configured to receive the hooks on the legs of the vessel filter 316 and to keep the hooks separated from each other, such that the legs of the filter will not be entangled with each other. Preferably, the connection between the extension wiring 318 and the pusher pad 314 is offset from the longitudinal axis of the pusher-wire 310 such that it does not interfere with the placement of the vessel filter 316 immediately distal 322 of the pusher pad 314. The extension wire may comprise Nitinol.

Figure 13:
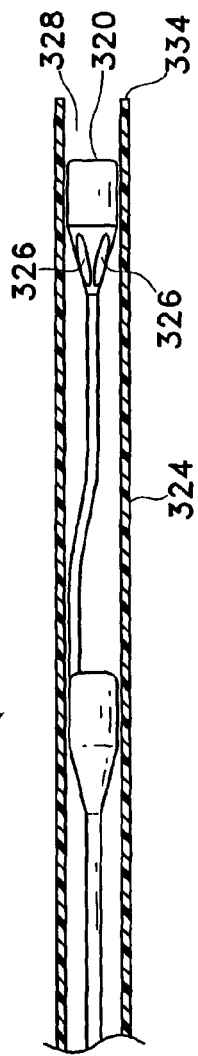
FIG. 13 illustrates the pusher device of FIG. 12 placed within the lumen of a delivery catheter.

The pusher-wire 310 may be placed inside of a catheter 324 to form a vessel filter delivery device 326 as shown in FIG. 13. In this example, the receptacle 320 is configured with a plurality of holes 326, each of which is designed to receive the distal end of a filter leg. The distal end of each of the legs may have a hook. The holes 326 may be large enough to accommodate the hooks in their expanded normal state (i.e., curved). However, it is preferable that the hooks comprise of shape memory alloy and are straightened before they are inserted into their corresponding holes 326 in the receptacle 320. To load a vessel filter 316 into the delivery device 326, the user may advance the distal portion of the pusher-wire 310 out of the distal lumen opening 328 of the delivery catheter 324. The vessel filter 316 is placed between the pusher pad 314 and the receptacle 320, and the legs 330 of the vessel filter 316 are inserted into the corresponding holes 326 on the receptacle 320. The user may pull on the proximal end of the pusher-wire 310, which extends from the proximal end of the delivery catheter 324, and drawn the distal portion of the pusher-wire 310 and the loaded vessel filter 316 into the lumen of the catheter 324.

The vessel filter delivery device 326 loaded with the vessel filter 316 may be inserted into an introducer sheath 332 that has been positioned within the circulatory system of a patient through methods that are well known to one of ordinary skill in the art. The vessel delivery device 326 is advanced along the length of the introducer sheath 332 until the distal end 334 of the delivery catheter 324 protrudes from the introducer sheath's 332 proximal lumen opening. FIG. 14A illustrates a delivery catheter 324 with a pusher-wire 310 having a vessel filter 316 loaded on the receptacle 320; the delivery catheter 324 being slidably disposed within the lumen of the introducer sheath 332.

To deploy the vessel filter 316 the user may retract the delivery catheter 324 and the introducer sheath 322 at the same time to expose the distal portion of the pusher-wire 310 and the vessel filter 316. The arms 336 on the vessel filter 316 expand and engage the wall of the blood vessel, as shown in FIG. 14B. The user may then advance the pusher-wire 310 in the distal direction and allow the legs 330 of the vessel filter 316 to slide out of the receptacle 320 at the distal end of the pusher-wire 310. The legs 330 expand and the hooks at the distal end of the legs 330 are embedded into the wall of the blood vessel. With the arms 336 and the legs 330 of the vessel filter 316 in the expanded positions, the receptacle 320 at the distal end of the pusher-wire 310 may be retrieved by pulling on the pusher-wire 310 and allowing the receptacle 320 to slide through one of the gaps between the expanded legs 330 and arms 336. The distal portion of the pusher-wire 310 along with its receptacle 320 can then be retracted into the lumen of the delivery catheter 324. The delivery catheter 324 and its introducer sheath 332 may then be removed from the body of the patient.

Alternatively, the compressed vessel legs 330 may have enough tension such that once the delivery catheter and the introducer sheath are retraced, as shown in FIG. 14B, the legs 14 will pop out of the receptacle. The holes on the receptacle and/or the hooks on the legs may be configured to facilitate the legs from exiting the receptacle when they are not compressed by the delivery catheter. In another variation, the hooks may comprise of Nitinol wires that are straightened before they are inserted into the holes on the receptacle. These straightened hooks may allow the legs of the vessel filter to disengage from the receptacle more easily. Once the legs are deployed, the patient's inner body temperature will force the straitened hooks to convert back into its original hook-shape and engage the inner wall of the blood vessel.

In another design, a second wiring having a jig or attachment mechanism at the distal end of the wiring may be placed within the delivery catheter along with the pusher-wire. The pusher pad 314 may have a side channel to allow the second wiring to pass-through. The jig at the distal end of the second wiring may engage the vessel filter sleeve. The delivery catheter and the introducer sheath are first partially withdrawn to expose the receptacle. Holding the second wiring in place to secure the filter in position, the pusher pad may then be advanced to push the receptacle forward through the extension wiring. As the consequence, the hooks at the distal end of the legs disengage from the receptacle and expand outward. The delivery catheter and the introducer sheath may then be completely retracted to expose the entire vessel filter. The jig on the second wiring is then detached from the vessel filter, and the second wiring along with the pusher-wire are retraced into the lumen of the delivery catheter. With the vessel filter deployed, the delivery catheter and the introducer sheath, along with the pusher-wire and the second wiring, may then be removed from the patient's body.

Alternatively, the second wiring, which engages the sleeve of the vessel filter, along with the pusher pad may be hold in place while the operator completely retracts the delivery catheter and the introducer sheath to expose the entire vessel filter.

The second wiring may then be utilized to pull vessel filter proximally and slide the hooks out of the receptacle. Once the vessel filter is deployed, the second wiring and the pusher-wire with the receptacle may then be retraced into the lumen of the delivery catheter. The operator may then remove the delivery catheter and the introducer sheath, along with the pusher-wire and the second wiring, from the patient's body. One of ordinary skill in the art having the benefit of this disclosure would appreciate that other variations of mechanisms may also be configured to disengage the legs of the vessel filter from the receptacle.

FIG. 15A illustrates one variation of a filter hook/leg receptacle 320. In this variation, the receptacle comprises a spline 338 with a plurality of orifices 340 for receiving the hooks. The proximal portion 342 of the receptacle 320 is configured with a cone-shaped profile 344. The cone-shaped profile may facilitate the retrieval of the receptacle 320 after the filter has been deployed by allowing the receptacle 320 to pass between the legs of the deployed filter with limited obstruction. A plurality of orifices 340 is provided on the cone-shaped profile 344 to receive the hooks and/or legs of the vessel filter. The cone-shaped profile 344 may also minimize obstruction and allow for easy insertion and smooth deployment of the legs. Preferably, the receptacle 320 has a circumferential outer surface 346 that matches or approximates the inner lumen of the delivery catheter, as shown in FIG. 15B, which may prevent kinking of the catheter and facilitate smooth advancement of the pusher-wire within the lumen of the catheter.

FIG. 15C is a cross-sectional view of this particular receptacle 320. In this example, the outer diameter of the receptacle 320 is 0.08 inches; the length of the receptacle "L30" is 0.380 inches; the base of the receptacle has a length "L31" of 0.147 inches; the depth "L32" of each of the holes 340 measure from the proximal end 348 of the receptacle 320 is 0.305 inches. To accommodate a filter with six hooks, six holes 340 are evenly distributed around a center opening 350, as shown in FIG. 15D. The center opening 350 is configured for receiving the distal end of the extension wire. The extension wire may be bonded into the center opening 350 of the receptacle 320. The spline 338 may comprise a metal, a metal alloy, or a polymeric material. The extension wire 318 may be a Nitinol wire that is 0.013 inches in diameter. As shown in FIG. 12, the pusher pad 314 may also be configured with a cone-shaped proximal profile 352, and a circumferential surface 354 matching or approximating the inner lumen of the delivery catheter 324. This may allow the pusher pad 314 to keep the extension wire connection 356 away from the center of the catheter to allow smoother deployment of the vessel filter 316. The pusher pad 314 may be of various shapes and comprise various materials (e.g., electrometric materials, metal, metal alloys, polymers, etc.) that are well know to one of ordinary skill in the art. One of ordinary skill in the art having the benefit of this disclosure would also appreciate that the receptacle 320 may adapt various other geometric shapes and still serve essentially the same function of keeping hooks on the legs separated from each other.

In another example, the receptacle is made of a spline 358 with an orifice 360 surrounding a post 362, as shown in FIG. 16A. The proximal end 364 of the post 362 can be connected to an extension wire on the pusher device. The inner circumferential surface of the spline 358 is embedded with a series of grooves 366 for separating the hooks at the distal ends of the legs, as shown in FIG. 16B.

In FIG. 17, another variation of a delivery catheter 3 is illustrated. In this configuration, a plurality of orifices 5 are provided at the distal portion of the delivery catheter for receiving and separating hooks on a vessel filter loaded within the lumen of the delivery catheter. The orifices 5 may be placed close to the distal end 7 of the catheter 3. In one example, the orifices 5 are placed within 2 mm from the distal end 7 of the catheter 3.

In one exemplary application, the vessel filter in inserted into the catheter by compressing its legs and corresponding arms, if any. The delivery catheter may be configured with six orifices for receiving hooks from a six legged filter with a hook located at the distal end of each of the legs. The vessel filter may be loaded from either distal or proximal end of the delivery catheter depending on the particular catheter design. For example, one may load the vessel filter from the distal end of the catheter by first inserting the proximal end (i.e., the sleeve of the vessel filter) into the distal lumen of the catheter. As the filter is completely advanced into the lumen of the catheter, the hooks on each of the legs will pop into the corresponding orifice on the delivery catheter. If the hooks are long enough, the hooks may pass through the orifices and protrude from the orifices' outer openings on the outer circumferential surface of the delivery catheter. As the delivery catheter with the loaded vessel filter is inserted into the proximal end of an introducer sheath, the protruding portion of the hooks will be forced back into the orifices. As the delivery catheter, along with the loaded vessel filter, is advanced towards the distal end of the introducer sheath, the hooks stays in their corresponding orifices and glides along the inner lumen wall of the introducer sheath. A pusher-wire with a pusher pad may be positioned within the lumen of the delivery catheter to keep the load vessel filter at the distal portion of the delivery catheter, as the delivery catheter is being displaced within the introducer sheath.

Once the delivery catheter and the corresponding introducer sheath is properly positioned within the blood vessel, the operator may then deploy the vessel filter by holding the pusher-wire in place, while simultaneously withdraw the delivery catheter and the corresponding introducer sheath. As the delivery catheter is withdrawn, the hooks on the vessel filter legs will be forced out of their corresponding orifices in the delivery catheter. The inner edge of each of the orifices maybe tapered on the distal side, which is closer to the distal end of the catheter, to facilitate the filter hooks from sliding out of the orifices when the delivery catheter is retracted. Once the delivery catheter and the corresponding introducer sheath are fully retracted, the legs and/or arms on the exposed delivery catheter may then expand and engage the inner wall of the blood vessel.

Figure 18:
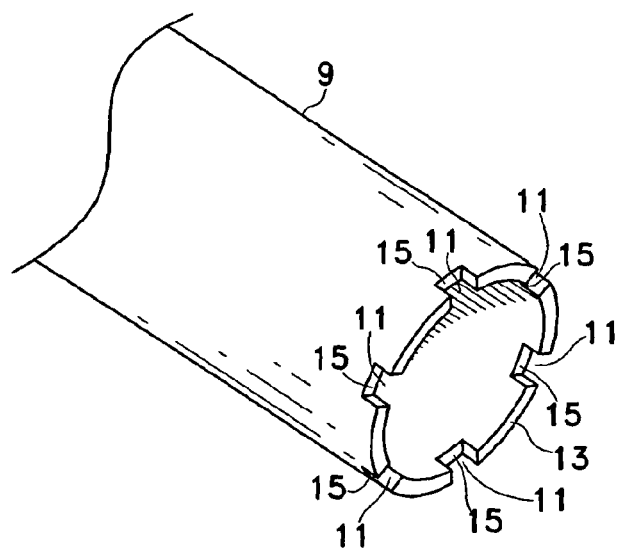
FIG. 18 illustrates another variation of a delivery catheter where a plurality of slots are provided at the distal end of the catheter for receiving and separating the hooks from a vessel filter inserted into the lumen of the catheter.

In FIG. 18, another variation of a delivery catheter 9 is shown. In this configuration, a plurality of slots 11 are provided at the distal end 13 of a catheter 9 for receiving and separating hooks on a vessel filter loaded within the lumen of the delivery catheter. As shown in FIG. 18, each of the slots spans across the thickness of the catheter wall, and opens toward the distal end 13 of the catheter. In one variation, the base 15 of each of the slots comprises a flat surface, as shown in FIG. 18. In another variation the base each of the slots has a rounded or otherwise curved profile. In the variation shown in FIG. 18, the slots are configured to receive a vessel filter with six equal length legs. However, if the legs of the vessel filter have varying lengths, the length of the slots along the longitudinal axis of the catheter may also be varied accordingly to accommodate the various vessel filter legs.

Figure 19:
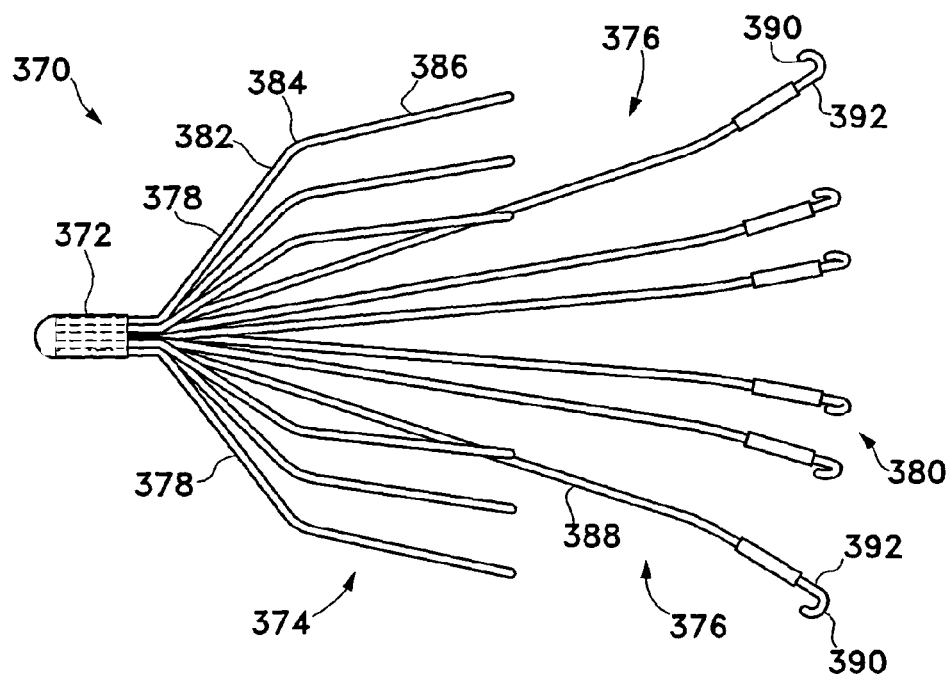
FIG. 19 illustrates another variation of a vessel filter.

Referring now to FIG. 19, another example of an implantable vessel filter 370, which may be deployed by the filter delivery device described above, is illustrated. In this variation, the vessel filter is made of elongated wires, and the wires are held together at the filter's proximal end by a hub 372 (e.g., sleeve) where they are plasma welded together to the hub or otherwise joined. In the low temperature martensitic phase of wires made of thermal shape memory material (e.g., Nitinol alloy), the sets of wires can be straightened and held in a straight form that can pass through a length of fine plastic tubing with an internal diameter of approximately 2 mm (e.g., 8 French catheter). In its high temperature austenitic form, the vessel filter 370 recovers a preformed filtering shape as illustrated by FIG. 19. Similarly, wires of spring metal can be straightened and compressed within a catheter or tube and will diverge into the filter shape of FIG. 19 when the tube is removed. In its normal expanded configuration or preformed filtering shape, the vessel filter 370 comprises a double filter, having a first proximally positioned basket section 374 and a second distally disposed filter basket section 376. The two filter basket sections provide peripheral portions which can both engage the inner wall of a body vessel at two longitudinally spaced locations, and the two filter basket sections are generally symmetrical about a longitudinal axis passing through the hub 372. On the other hand, the first filter basket section 374, which may act as a centering unit, may not always touch the vessel wall on all sides.

The first filter basket section 374 is formed from short lengths of wire, which form legs 378 extending angularly, outwardly and then downwardly away from the hub 372 and toward the distal end 380 of the vessel filter 370. Each leg 378 has a first leg section 382, which extends angularly outwardly from the hub 372 to a transition section 384, and an outer leg section 386, which extends angularly from the transition section 384 toward the distal direction of the filter. The outer leg sections 386 are substantially straight lengths with ends that lie on a circle at their maximum divergence and engage the wall of a vessel at a slight angle (preferably within a range of from ten to forty-five degrees) to center the hub 372 within the vessel. For a filter which is to be removed by grasping the hub 372, it may be important for the hub to be centered. The filter may be configured with six wires 378 of equal length extending radially outward from the hub 372 and circumferentially spaced, such as, for example, by sixty degrees of arc.

The second filter basket section 376 is the primary filter and can include up to twelve circumferentially spaced straight wires 388 forming downwardly extending legs which tilt outwardly of the longitudinal axis of the filter 370 from the hub 372. A filter with a six wire configuration is discussed in this example, and the wires are of equal length. Alternatively, the length of the wiring may be staggered. The wires 388 are preferably much longer than the wires 378, and have distal tip sections which are uniquely formed, outwardly oriented hooks 390 which lie on a circle at the maximum divergence of the wires 388. There may be from three to twelve wires 388 formed with hooks 390, and in some instances, the wire legs 378 may include similarly formed hooks at the free ends thereof. The wires 388, in their expanded configuration of FIG. 17, are at a slight angle to the vessel wall, preferably within a range of from ten to forty-five degrees, while the hooks 390 penetrate the vessel wall to anchor the filter against movement. The wires 388 are radially offset relative to the wires 90 and may be positioned halfway between the wires 378 and also may be circumferentially spaced by sixty degrees of arc. Thus, the combined filter basket sections 374 and 376 can provide a wire positioned at every thirty degrees of arc at the maximum divergence of the filter sections. The filter section 376 forms a concave filter basket opening toward the distal end of the filter 370, while the filter section 374 forms a concave filter proximal of the filter section 376.

Furthermore, the hooks 390 on the distal legs may be further configured such that withdrawal force to which the hook is subjected will cause flexure in the juncture sections 392 so that the hook extends in the distal direction of the filter to a position parallel or semi-parallel with the axis of the leg 388. For example, the juncture section 392 may have considerably reduced cross-section relative to the cross-section of the leg 388 and the remainder of the hook 390 so that the stress exerted by the withdrawal tension may force it to bend outward. With the hook so straightened, it can be withdrawn without tearing the vessel wall, leaving only a small puncture. In an alternative design, the entire hook 390 can be formed with a cross-section throughout its length, which is less than that of the leg 388. This may result in straightening of the hook over its entire length in response to a withdrawal force. Such elasticity in the hook structure may prevent the hook from tearing the vessel wall during withdrawal.

In addition, a hook or attachment interface may be provided at the proximal end of the hub to allow the operator to manipulate the vessel filter through an elongated wire with a matching interface for engaging the hook or the attachment interface. For example, a hook positioned at the proximal end of the hub 372 may facilitate the removal of the vessel filter. The operator may engage the hook with and elongated wire and hold the vessel in place while simultaneously advance a catheter over the implanted vessel filter. The catheter forces the legs on the vessel filter to collapse and slide into the lumen of the catheter. Once the vessel filter is inside the catheter the catheter, along with the retracted vessel filter, may then be removed from the patient's body.

This invention has been described and specific examples of the invention have been portrayed. While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well. Finally, all publications and patent applications cited in this specification are herein incorporated by reference in their entirety as if each individual publication or patent application were specifically and individually put forth herein.

All measurements disclosed herein are at standard temperature and pressure, at sea level on Earth, unless indicated otherwise. All materials used or intended to be used in a human being are biocompatible, unless indicated otherwise.

The foregoing embodiments are presented by way of example only; the scope of the present invention is to be limited only by the following claims.

The invention claimed is:

1. A vessel filter delivery system, comprising:
a) an elongated flexible tube having a central, longitudinal axis, proximal and distal ends, and a tube wall with an outer surface and an inner surface surrounding a tube lumen that extends from the proximal end to the distal end;
b) an expandable vessel filter stored within the tube lumen in a compressed state, the filter including a head and multiple legs extending distally of the head, at least some legs having a distal hook, each distal hook having a hook free end;
c) wherein the filter is movable between the compressed state wherein the filter is contained in the tube lumen and an expanded state wherein the filter is positioned distally of the distal end of the elongated flexible tube;
d) the tube wall including a plurality of slots that each communicate with the distal end of the flexible tube, wherein the slots are circumferentially spaced apart about the tube wall inner surface and lumen, the slots extending longitudinally along the tube wall inner surface, each slot terminating proximally at a radially extending ledge;
e) wherein in said compressed state each of the slots receiving at least a portion of a hook of a vessel filter leg, wherein the hook free end of each leg engages the ledge to prevent the vessel filter from migrating beyond the ledge in a proximal direction; and
f) a pusher that engages the filter head proximally and opposite the hooks, wherein the pusher is movable within the tube lumen from a proximal position to a distal position which proximal to distal movement of the pusher enables discharge of the filter from the tube and to the expanded state, wherein the hooks exit the tube before the head exits the tube.

2. The vessel filter delivery system according to claim 1, wherein the radially extending ledge is generally perpendicular to the central, longitudinal tube axis.

3. A vessel filter assembly, comprising:
a) a vessel filter including a head and a plurality of elongated legs extending distally from said head;
b) said plurality of elongated legs being configured to expand radially from an initial stored position to an expanded position;
c) each of said plurality of legs having a hook located at a distal end thereof such that when said legs are moved to the expanded position the hooks engage an inner wall of the vessel, each hook having a hook free end;
d) an elongated catheter having a central, longitudinal axis and including an inner surface surrounding a lumen that extends from a proximal catheter end to a distal catheter end, the lumen being configured to receive said vessel filter and maintain said vessel filter in a first compressed configuration that defines said stored position;
e) a plurality of grooves being provided on the distal end of the catheter and communicating with the inner surface, said grooves being circumferentially spaced apart and configured for receiving said hooks;
f) a transverse surface that transversely intersects each groove proximally of said groove;
g) wherein in the first compressed, stored position, the hooks engage the catheter wall at said grooves to prevent said plurality of legs from entangling with each other; and
h) wherein in the first compressed, stored position, each hook free end engages a said transverse surface;
j) a filter delivery portion that comprises a rod slidably positioned within said elongated catheter for applying pressure when said vessel filter is to be moved from the stored position to a deployed position exiting from the distal end of said elongated catheter.

4. The vessel filter assembly according to claim 3, wherein said vessel filter further comprises a plurality of arms extending distally from said head, wherein said plurality of arms are configured to expand radially from a longitudinal axis to form a second filter portion in an expanded position.

5. The vessel filter assembly according to claim 4, wherein said arms are compressed by an inner wall of said catheter, and wherein said arms do not engage said plurality of grooves when said vessel filter is positioned within the lumen of said catheter.

6. The vessel filter assembly according to claim 3, wherein said vessel filter is conically shaped.

7. The vessel filter assembly according to claim 3, wherein a length along the longitudinal axis of said catheter for each of said grooves is approximately the length of said hooks along the longitudinal axis of each of said hook's corresponding leg.

8. The vessel filter assembly according to claim 3, wherein said grooves are configured to prevent the vessel filter from sliding proximally along the lumen of the catheter once said hooks are placed within said grooves.

9. The vessel filter assembly according to claim 8, wherein each of said grooves is configured with a distal end opening at a distal tip of said elongated catheter to allow said hooks to slide out of said grooves, and wherein a proximal end of each of said grooves includes said transverse surface for blocking said hooks and preventing said vessel filter from migrating in the proximal direction along the length of the catheter.

10. The vessel filter assembly according to claim 3, wherein each of said grooves is configured with a distal end opening at a distal tip of said elongated catheter to allow said hooks to slide out of said grooves, and wherein a proximal end of each of said grooves includes said transverse surface for blocking said hooks and preventing said vessel filter from migrating in the proximal direction along the length of the catheter.

11. The vessel filter assembly according to claim 3, wherein said grooves are configured such that said grooves prevent said vessel filter from sliding proximally along the lumen of the catheter once said hooks are placed within said grooves.

12. The vessel filter assembly according to claim 3, wherein said elongated catheter comprises a flexible tubing and a spline cap attached to a distal end of said tubing, said spline cap being configured with said plurality of grooves at the distal end thereof, said grooves being positioned on an inner wall surrounding a lumen of said spline cap, and said grooves being configured to receive said hooks and to prevent said plurality of legs from entangling with each other.

13. The vessel filter assembly according to claim 12, wherein said grooves are configured to prevent said vessel filter from sliding proximally along the lumen of the catheter once said hooks are placed within said grooves.

14. The vessel filter assembly according to claim 12, wherein each of said grooves is configured with a distal end opening at the distal end of said spline cap to allow said hook to slide out of said groove, and wherein a proximal end of each of said grooves includes said transverse surface for blocking said hook and preventing said vessel filter from migrating in the proximal direction along a length of said flexible tubing.

15. The vessel filter assembly according to claim 3, further comprising a filter delivery portion that comprises a sheath slidably disposed around said elongated catheter.

16. The vessel filter assembly according to claim 3, wherein the radially extending transverse surface is generally perpendicular to the central, longitudinal tube axis.

17. A vessel filter delivery device for implanting an expandable vessel filter in a hollow body organ in a human, comprising:
a) an elongated flexible tube having proximal and distal tube ends, an outer surface, an inner circumferential surface, a tube lumen extending from the proximal tube end to the distal tube end;
b) an expandable filter contained within said tube lumen in a first, stored position, said filter including a plurality of filter legs, each leg having a distal hook with a hook free end;
c) a plurality of slots positioned at said distal end of the tube and each slot communicating with the inner circumferential surface thereof and tube lumen;
d) wherein in said stored position, each of said slots being configured to receive one of a plurality of said hooks on said expandable vessel filter;
e) a distal end of said slots opening at the tube distal end to allow said hooks to move distally of the tube lumen; and
f) a proximal end of each said slot including a radially extending ledge to prevent the vessel filter from migrating towards said proximal end of said tube, wherein each hook free end engages a said radially extending ledge in the stored position;
g) an elongated flexible wire slidably disposed within the lumen of said elongated flexible tube, wherein a distal end of said elongated flexible wire is configured to apply a force on said vessel filter to deploy said vessel filter from the lumen of said tube.

18. The vessel filter delivery device according to claim 17, wherein said expandable filter forms a conical shape in an expanded state, and wherein said hooks are discharged from and spaced from the distal end of said tube.

19. The vessel filter delivery device according to claim 17, further comprising a plurality of flexible elements including first and second ends, each of said flexible elements being attached to the distal end of said elongated flexible tube at the first end of said flexible element, the second end of said flexible element extending distally away from the distal end of said elongated flexible tube and outwardly away from a longitudinal axis of said elongated flexible tube.

20. The vessel filter delivery device according to claim 17, further comprising an introducer sheath, wherein a lumen in said introducer sheath is configured to slidably receive said elongated flexible tube, the introducer sheath comprising an interlocking mechanism for temporarily securing said elongated flexible tube within the lumen of said introducer sheath such that the introducer sheath and the elongated tube can be displaced inside a blood vessel as a single unit.

* * * * *